US007122694B2

(12) United States Patent
Marcuccio et al.

(10) Patent No.: US 7,122,694 B2
(45) Date of Patent: Oct. 17, 2006

(54) HYDROBORONATION PROCESS

(75) Inventors: Sebastian Mario Marcuccio, Endeavour Hills (AU); Mary Rodopoulos, Blackburn South (AU); Helmut Weigold, Mount Waverely (AU)

(73) Assignee: Boron Molecular Pty Limited, Noble Park (AU)

( * ) Notice: Subject to any disclaimer, the term of this patent is extended or adjusted under 35 U.S.C. 154(b) by 96 days.

(21) Appl. No.: 10/740,674

(22) Filed: Dec. 22, 2003

(65) Prior Publication Data

US 2004/0133028 A1   Jul. 8, 2004

Related U.S. Application Data

(62) Division of application No. 09/807,955, filed as application No. PCT/AU99/00967 on Nov. 5, 1999, now Pat. No. 6,680,401.

(30) Foreign Application Priority Data

Nov. 6, 1998  (AU) ................. PP6977/98
Dec. 24, 1998 (AU) ................. PP7935/98
Aug. 11, 1999 (AU) ................. PQ2158/99

(51) Int. Cl.
     C07F 5/04   (2006.01)
(52) U.S. Cl. ..................................... 558/286
(58) Field of Classification Search ................. 558/286
     See application file for complete search history.

(56) References Cited

U.S. PATENT DOCUMENTS 3,383,401 A   5/1968   Woods et al.

FOREIGN PATENT DOCUMENTS

| FR | 1536699 A | 8/1968 |
| WO | WO 98 45265 A | 9/1998 |
| WO | WO 98/45265 A | 10/1998 |
| WO | WO 98/58935 | 12/1998 |
| WO | WO 99/12940 A | 3/1999 |

OTHER PUBLICATIONS

CA:129:216422 abs of WO 9837068 Aug. 27, 1998.*
CA:102:76929 abs of Chemiker-Zeitung by Dallacker et al 108(9) pp. 287-288 1984.*
CA:92:226117 abs of journal of Chromatography 186 pp. 307-316 1979.*
CA:129:149097 abs of WO 9831688 Jul. 1998.*
CA:116:234731 abs of Tetrahedron: Asymmetry by Kawate et al 3(2) pp. 227-230 1992.*
Juliette et al., Transition Metal Catalysis in Fluorous Media: Practical Application of a New Immobilization Principle to Rhodium-Catalyzed Hydroborations of Alkenes and Alkynes, J. Am. Chem. Soc.; (Article); 1999; 121(12); 2696-2704.*

Westcott et al., New homogeneous rhodium catalysts for the regioselective hydroboration of alkenes, J. Am. Chem. Soc.; 1992; 114(23); 8863-8869.*
Murata M. et al., Novel palladium (O)-catalyzed coupling reaction of dialkoxyborane with aryl halides; convenient synthetic route to arylboronates, J. Org. Chem., 1997, 62(19), 6458-6459.
Bello-Ramirez MA et al., Dioxaborolanes and borates derived from 2,3-butanediol, mandelic acid and quinic acid [1], Heteroat Chem, 1993, 4(6), 613-620 & Chemical Abstract 120:323631.
Gamble MP et al., Design, synthesis and applications of a ketone reduction catalyst containing a phosphinamide combined with a dioxaborolidine unit, Tetrahedron Asymmetry, 1996, 7(11), 3071-3076 & Chemical Abstract 126:60028.
Matteson DS et al., synthesis and properites of pinanediol α-amido boronic esters, Organometallics, 1984, 3(8), 3(8), 1284-1288 & Chemical Abstract 101:111361.
Burgess K et al., Ruthenium-catalyzed hydroboration of alkenes, Organometallics, 1993, 12(10), 4197-4200 & Chemical Abstract 119:249249.
Fish RH, The addition of 4,4,6-trimethyl-1,3,2-dioxaborinane to allenes, J. Am. Chem. Soc., 1968, 90(16), 4435-4439 & chemical Abstract 69:85901.
Chemical Abstract 129:216633 (JP 102112279A2) Aug. 11, 1998.
Chemical Abstract 116:128127 & Arase A et al., Lithium triethylborohydride-promoted hydroboration of alkenes with dialkoxyboranes, J. Chem. Soc. Chem. Comm., 1992, (1), 51-52.
Database CA 'Online! Chemical Abstracts Service, Columbus, Ohio, US; Dallacker, Franz et al., "Preparation of 1,3-benzodioxole boron compounds" retrieved from STN Database accession No. 102:78929 CA, XP002202094, Abstract, & Chem.-ZTG. (1984), 108(9), 287-8 1984.
Database Crossfire Beilstein 'Online! Beilstein Institut zur Forderung der Chemischen Wissenschaften, Frankfurt am Main, DE; Database accession No. Reaction ID 7840619, XP002202095, Abstract, & Bamford: Forham: Sci Monogr., vol. 13, 1961, pp. 320-322.

(Continued)

Primary Examiner—Johann Richter
Assistant Examiner—Chukwuma Nwaonicha
(74) Attorney, Agent, or Firm—Bacon & Thomas, PLLC

(57) ABSTRACT

The invention relates to processes for the synthesis of aryl or alkene borates which comprises reacting: (i) an olefinic compound having a halogen or halogen-like substituent in a vinylic substitution position, or (ii) an aromatic ring having a halogen or halogen-like substituent in a ring substitution position, with a disubstituted monohydroborane in the presence of a Group 8–11 metal catalyst. The invention also relates to the use of these borates in coupling reactions. The invention further relates to certain disubstituted monohydroboranes and aryl or alkene borates.

41 Claims, No Drawings

OTHER PUBLICATIONS

Ishiyama T. et al., "Synthesis of Arylboronates via the Palladium(0)-Catalyzed Cross- Coupling Reaction of Tetra(Alkoxo)Diborons with Aryl Triflates", Tetrahedron Letters, Elsevier Science Publishers, Amsterdam, NL., vol. 38, No. 19, May 12, 1997, pp. 3447-3450, XP000686267.

CA:102:78929 abs of Chemiker-Zeitung by Dallacker et al. 108(9) pp. 287-288 1984.

CA:116:234731 abs of Tetrahedron: asymmetry by Kawate et al. 3(2) pp. 227-230 1992.

Database CA, 'Online! Chemical Abstracts Service, Columbus, Ohio, US; Dallacker, Franz et al., "Preparation of 1,3-benzodioxole boron compounds" retrieved from STN Database accession No. 102:78929 CA XP002202094, Abstract, & Chem.-ZTG. (1984), 108(9), 287-8, 1984.

Database Crossfire Beilstein 'Online! Beilstein Institut zur Forderung der Chemischen Wissenschaften, Frankfurt am Main, DE; Database accession No. Reaction ID 7840619, XP002202095, Abstract, & Bambord; Forham: SCI Monogr., vol. 13, 1961, pp. 320-322.

Ishiyama T. et al., "Synthesis of Arylboronates via the Palladium(0)-Catalyzed Cross-Coupling Reaction of Tetra(Alkoxo)Diborons with Aryl Triflates", Tetrahedron Letters, Elsevier Science Publishers, Amsterdam, NL., vol. 38, No. 19, May 12, 1997, pp. 3447-3450 ISSN 0040-4039, Table 1.

* cited by examiner

HYDROBORONATION PROCESS

This application is a divisional application of U.S. application Ser. No. 09/807,955, filed Aug. 13, 2001 now U.S. Pat. No. 6,680,401 (of which the entire disclosure of the prior application is hereby incorporated by reference), for which the Issue Fee has been paid on Nov. 14, 2003, which is a 371 of PCT/AU99/00967, filed Nov. 5, 1999.

This invention relates to a process for preparing organoboron compounds which involves reacting an appropriately substituted organic compound with a substituted borane. In particular the invention relates to the synthesis of aryl or vinyl borates using disubstituted monohydroboranes and related species. These organoborates, and their corresponding boronic acids, are useful reactants in organic coupling reactions. They are particularly useful in the synthesis of new and known organic molecules and have application in the synthesis of pharmaceuticals, pesticides and other useful organic compounds. The compounds represent useful intermediates and building blocks for organic synthesis and are useful in combinatorial chemistry.

Processes for forming covalent bonds between organic compounds, both inter- and intra-molecular, are of particular importance to the synthetic organic chemist. Many such reactions are known, each requiring its own special reaction conditions, solvents, catalysts, activating groups etc. Some known types of coupling reactions involving olefinic moieties include the Michael reaction and reactions described in the following references: Transition Metals in the Synthesis of Complex Organic Molecules (L. S. Hegedus, University Science Books, 1994, ISBN 0-935702-28-8); Handbook of Palladium Catalysed Organic Reactions (J. Malleron, J. Fiaud and J. Legros, Academic Press, 1997, ISBN 0-12-466615-9); Palladium Reagents and Catalysts (Innovations in Organic Synthesis by J. Tsuji, John Wiley & Sons, 1995, ISBN 0-471-95483-7); and N. Miyuara and A. Suzuki, Chem Rev. 1995, 95, 2457–2483.

Catalysts of palladium, its complexes and its salts are well recognised for activation of C—H bonds towards coupling reactions. In this regard the Heck reaction of an alkene with an aryl or vinyl halide in the presence of palladium derivatives has been the subject of intensive study. Other Group VIII metal catalysts, such as platinum, have also been used to activate such carbon bonds.

The success of the Heck reaction depends to a large extent on the substrates and the reaction conditions. When two β-hydrogens are present in the alkene the reaction generally leads to the formation of the (E)-alkenes which are often contaminated with the corresponding (Z)-alkenes.

Although alkene borates (alkenylborates) can be reacted with a variety of organic molecules to give coupled products via the formation of new carbon-carbon bonds (See for example the references above) the process for the preparation of the alkenylborates by the commonly used hydroboration reaction of alkynes is limited because of the difficulties that are encountered through the lack of regiochemistry and/or chemoselectivity (such as the reduction of a number of different functional groups) (See N. Miyuara and A. Suzuki, Chem Rev. 1995, 95, 2457–2483). Improved methodologies are thus required for the synthesis of alkene borates.

Substituted bi- and tri-aryl compounds are of great interest to the pharmaceutical and agrochemical industries. A great number of these compounds have been found to possess pharmaceutical activity, while others have been found to be useful pesticides. There is also interest from the polymer industry in polymers prepared by the linking together of aromatic ring compounds.

Conventional methods for covalently linking aromatic rings, such as by reaction of an appropriate Grignard reagent, involve harsh conditions and are not suitable for aromatic rings with active hydrogen containing substituents. Substituents with active hydrogen atoms also can become involved in unwanted side reactions leading to undesirable products. Such substituents need to be protected prior to reaction. Boronic acid derivatives required for the Suzuki reaction are traditionally synthesized through highly reactive organometallic intermediates.

In view of the severity of the reaction conditions the range of substituents which could be present during the formation of the boronic acid derivatives was considerably limited, and the range of useful reaction media (solvents) was restricted.

It has now been found that aryl and alkene borates can be synthesised from particular substituted olefinic or aromatic ring compounds under mild conditions and in the presence of a range of substituents. This process overcomes or at least alleviates one or more of the limitations encountered in the use of the conventional hydroboration methodology and is fundamentally different, in the case of the preparation of alkene borates, in that the starting material is an alkene and not an alkyne.

Accordingly the invention provides a process for the synthesis of an alkene or aryl borate which comprises reacting:

(i) an olefinic compound having a halogen or halogen-like substituent in a vinylic substitution position, or (ii) an aromatic ring compound having a halogen or halogen-like substituent in a ring substitution position, said aromatic ring compound also having at least one substituent selected from the group consisting of hydroxy, amino, imino, acetyleno, carboxy (including carboxylato), carboximidyl, sulfo, sulfinyl, sulfinimidyl, sulfinohydroximyl, sulfonimidyl, sulfondiimidyl, sulfonohydroximyl, sultamyl, phosphinyl, phosphinimidyl, phosphonyl, dihydroxyphosphanyl, hydroxyphosphanyl, phosphono (including phosphonato), hydrohydroxyphosphoryl, allophanyl, guanidino, hydantoyl, ureido, and ureylene with a disubstituted monohydroborane, in the presence of a Group 8–11 metal catalyst and a suitable base, such that a borane residue is introduced at the substitution position.

For convenience, the reaction described above will be referred to as the "boronation reaction".

The term "disubstituted monohydroborane" refers to a monoboron compound having two non-hydrogen substituents and one hydrogen substituent.

The term "borane residue" refers to a disubstituted monohydroborane moiety after breakage of the B—H bond. An example of a borane residue is the moiety $(RO)_2B-$ where R is as defined below.

This process is fundamentally different from the conventional hydroboration processes in that substitution occurs rather than addition. Accordingly a completely different mechanism is involved.

According to conventional hydroboration processes, alkyl 3 and alkeneboronic esters 5 are prepared from the corresponding alkenes 2 and alkynes 4 as shown below with pinacol borane:

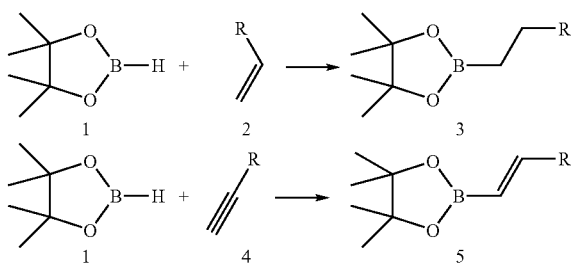

These reactions formally add one hydrogen and a boronic acid ester across the respective substrates. No base is required and although the reactions may be catalysed by transition metal species these are not essential. With monoalkyl alkynes the reactions yield the (E)-pinacol (1-alkenyl)boronates 5 as the major stereoisomer. The other two isomers 5a and 5b are difficult to obtain using this methodology.

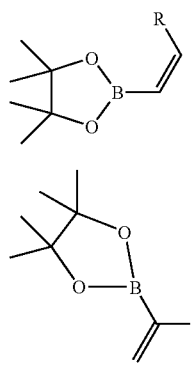

However the present invention provides a convenient route to these difficult to obtain isomers. Instead of addition across a double bond as described above the present invention results in the replacement of a halide or halogen-like substituent in the vinylic position with a borane residue. Accordingly the location of the borane residue in the product is governed by the location of the halide.

Aromatic compounds do not hydroboronate with the use of the reagent 1.

The process according to the present invention also provides advantages over other processes for activating carbon atoms towards coupling reactions. According to the present process it is possible to synthesise a wide range of substituted aryl and alkene borates, without the need for the prior protection of a wide variety of functional groups, including active hydrogen functionalities.

It is possible to generate the disubstituted monohydroborane in situ by reaction of a borane with an appropriate alcohol or amine. In a particularly preferred embodiment the borane ester so prepared can be used without isolation in the boronation reaction. This process can be used to generate esters, as well as ester/amides or diamides. This process surprisingly allows the generation and reaction of disubstituted monohydroboranes which cannot be isolated in their pure form or which readily disproportionate. Some amine species may give adducts of borane that are not sufficiently reactive to give the desired $H_2$ elimination and these reactions may require more vigorous conditions.

Preferably the borane used to generate the disubstituted monohydroborane is a polyhydroborane. Examples of polyhydroboranes which may be useful according to this aspect of the invention include sulphide and ether adducts of $BH_3$. Examples of such adducts include dialkylsulphide adducts, such as $BH_3.S(CH_3)_2$, ether adducts, such as $BH_3.THF$, and cyclic sulphide adducts such as $BH_3.1,4$-oxathiane. Preferably the adduct is $BH_3.S(CH_3)_2$.

As mentioned above the aryl and alkene borates so produced may be coupled to other organic compounds having a halogen or halogen-like substituent by reacting the borate with the organic compound in the presence of a Group 8–11 metal catalyst and a suitable base.

Accordingly the invention provides a process for covalently coupling organic compounds which comprises:
(A) preparing an alkene or aryl borate by reacting
  (i) an olefinic compound having a halogen or halogen-like substituent in a vinylic coupling position, or
  (ii) an aromatic ring compound having a halogen or halogen-like substituent in a ring coupling position, said aromatic ring compound also having at least one substituent selected from the group consisting of hydroxy, amino, imino, acetyleno, carboxy (including carboxylato), carboximidyl, sulfo, sulfinyl, sulfinimidyl, sulfinohydroximyl, sulfonimidyl, sulfondiimidyl, sulfonohydroximyl, sultamyl, phosphinyl, phosphinimidyl, phosphonyl, dihydroxyphosphanyl, hydroxyphosphanyl, phosphono (including phosphonato), hydrohydroxyphosphoryl, allophanyl, guanidino, hydantoyl, ureido, and ureylene, with a disubstituted monohydroborane, in the presence of a Group 8–11 metal catalyst and a suitable base, such that borane residue is introduced at said coupling position; and
(B) reacting the alkene or aryl borate with an organic compound having a halogen or halogen-like substituent at a coupling position in the presence of a Group 8–11 metal catalyst and a suitable base, whereby the olefinic or aromatic ring compound is coupled to the organic compound via a direct bond between the respective coupling positions.

This process allows for the preparation of symmetrical and asymmetrical products by selection of appropriate reactants.

It is especially convenient to conduct this process in a single pot without isolating the aryl or alkene borate, however it has been found that the presence of unreacted disubstituted monohydroborane can interfere with the coupling step, resulting in the formation of unwanted by-products.

Accordingly, after preparation of the aryl or alkene borate, excess disubstituted monohydroborane may be decomposed by adding a suitable proton donor compound such as water, alcohols, acids or mixtures thereof. The ease with which the excess disubstituted monohydroborane can be destroyed is of specific advantage in the formation of asymmetrically coupled products by the 'one pot' method. In particular, the formation of asymmetrically coupled compounds, to the exclusion of symmetrically coupled compounds, requires that there is no excess disubstituted monohydroborane present in the reaction solution when organic compound having a halogen or halogen-like substituent in a coupling position is added to the preformed boronic acid ester.

In the case of olefinic and aromatic ring compounds having halogen or halogen substituents in vinylic or ring coupling positions respectively it is possible to prepare symmetrical products in a number of ways.

In one embodiment the disubstituted monoborane is contacted with two equivalents of olefinic or aromatic ring compound to form an alkene or aryl borate, which borate reacts with the remaining halogenated compound to form the coupled product. According to this embodiment the covalent coupling comprises a covalent bond between the respective coupling positions of two molecules of the halogenated compound. A second base may be added and/or the reaction mixture may be heated after the formation of the aryl or alkene borate to catalyse or promote the coupling reaction. Alternatively oxidative coupling may be used, such as described in Katharine H. Smith, Eva M. Campi, W Roy Jackson, Sebastian Marcuccio, Charlotta G. M. Naeslund and Glen B. Deacon *Synlett* January 1997, 131–132.

The symmetrical product may also be prepared by first preparing the aryl or alkene borate and then adding further halogenated compound to the reaction medium. As with the previous method it may be necessary to add base and/or heat to the reaction to promote the coupling reaction. If, instead of adding the same halogenated compound to the reaction medium, a different halogenated compound is added, then unsymmetrical products can be obtained. Destruction of the excess monohydroborane before addition of the organic compound is advantageous. Adding a second solvent in which the base is soluble is also of advantage when the base is not soluble in the solvent used for the borate synthesis.

The terms "olefinic" and "olefinic compound" as used herein refer to any organic compound having at least one carbon to carbon double bond which is not part of an aromatic or pseudo aromatic system. The olefinic compounds may be selected from optionally substituted straight chain, branched or cyclic alkenes; and molecules, monomers and macromolecules such as polymers and dendrimers, which include at least one carbon to carbon double bond. Examples of suitable olefinic compounds include but are not limited to ethylene, propylene, but-1-ene, but-2-ene, pent-1-ene, pent-2-ene, cyclopentene, 1-methylpent-2-ene, hex-1-ene, hex-2-ene, hex-3-ene, cyclohexene, hept-1-ene, hept-2-ene, hept-3-ene, oct-1-ene, oct-2-ene, cyclooctene, non-1-ene, non-4-ene, dec-1-ene, dec-3-ene, buta-1,3-diene, penta-1,4-diene, cyclopenta-1,4-diene, hex-1,diene, cyclohexa-1,3-diene, cyclohexa-1,4-diene, cyclohepta-1,3,5-triene and cycloocta-1,3,5,7-tetraene, each of which may be optionally substituted. Preferably the straight chain branched or cyclic alkene contains between 2 and 20 carbon atoms. The olefinic compounds may be α,β-unsaturated carbonyl compounds, or conjugated dienes. The term "conjugated dienes" as used herein refers to any compound capable of acting as a diene in a Diels-Alder reaction.

In one embodiment the olefinic compound (i) is a compound of formula I

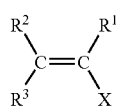

where $R^1$, $R^2$ and $R^3$ are each independently selected from hydrogen, alkyl, alkenyl, alkynyl, aryl, heteroaryl, acyl, arylalkyl and heteroarylalkyl (each of which may be optionally substituted), cyano, isocyano, formyl, carboxyl, nitro, halo, alkoxy, alkenoxy, aryloxy, benzyloxy, haloalkoxy, haloalkenyloxy, haloaryloxy, nitroalkyl, nitroalkenyl, nitroalkynyl, arylamino, diarylamino, dibenzylamino, alkenylacyl, alknylacyl, arylacyl, acylamino, diacylamino, acyloxy, alkylsulphonyloxy, arylsulphenyloxy, heterocycloxy, arylsulphenyl, carboalkoxy, carboaryloxy, alkylthio, benzylthio, acylthio, sulphonamide, sulfanyl, sulfo, carboxy (including carboxylato), carbamoyl, carboximidyl, sulfinyl, sulfinidyl, sulfinohydroximyl, sulfonimidyl, sulfondiimidyl, sulfonohydroximyl, sulfamyl, phosphorous containing groups (including phosphinyl, phosphinimidyl, phosphonyl, dihydroxyphosphanyl, hydroxyphosphanyl, phosphone (including phosphonato) and hydrohydroxyphosphoryl), alkoxysilyl, silyl, alkylsilyl, alkylalkoxysilyl, phenoxysilyl, alkylphenoxysilyl, alkoxyphenoxy silyl and arylphenoxy silyl.

The term "aromatic ring compound(s)" as used herein refers to any compound which includes or consists of one or more aromatic or pseudoaromatic rings. The rings may be carbocyclic or heterocyclic, and may be mono or polycyclic ring systems. Examples of suitable rings include but are not limited to benzene, biphenyl, terphenyl, quaterphenyl, naphthalene, tetrahydronaphthalene, 1-benzylnaphthalene, anthracene, dihydroanracene, benzanthracene, dibenzantacene, phenanthracene, perylene, pyridine, 4-phenylpyridine, 3-phenylpyridine, thiophene, benzothiophene, naphthothiophene, thianthrene, furan, pyrene, isobenzofuram, chromene, xanthene, phenoxathiin, pyrrole, imidazole, pyrazole, pyrazine, pyrimidine, pyridazine, indole, indolizine, isoindole, purine, quinoline, isoquinoline, phthalazine, quinoxaline, quinazoline, pteridine, carbazole, carboline, phenanthridine, acridine, phenanthroline, phenazine, isothiazole, isooxazole, phenoxazine and the like, each of which may be optionally substituted. The term "aromatic ring compound(s)" includes molecules, and macromolecules, such as polymers, copolymers and dendrimers which include or consist of one or more aromatic or pseudoaromatic rings. The term "pseudoaromatic" refers to a ring system which is not strictly aromatic, but which is stablized by means of delocalization of π electrons and behaves in a similar manner to aromatic rings. Examples of pseudoaromatic rings include but are not limited to furan, thiophene, pyrrole and the like.

As used herein the term "organic compound having a halogen or halogen-like substituent at a coupling position" refers to any organic compound having a carbon to halogen or carbon to halogen-like substituent bond at a position where coupling to the olefinic or aromatic compound is desired. The organic compound may be aliphatic, olefinic, allylic, acetylenic, aromatic, polymeric or dendritic. The organic compound may be an olefinic compound as defined above or part of such an olefinic compound. The organic compound may have one or more, preferably between 1 and 6, halogen or halogen-like substituents at coupling positions.

The term "coupling position" as used herein refers to a position on an organic compound at which coupling to another organic compound is desired. A coupling position on a carbon atom which is part of an olefinic carbon to carbon bond is also referred to as a "vinylic coupling position". Each olefinic compound or organic compound may have one or more, preferably between 1 and 6, coupling positions.

The term "substitution position" as used herein refers to a position on an olefinic or aromatic ring compound at which substitution with a borane residue is desired. Each organic compound may have one or more, preferably between 1 and 6, substitution positions. In an aromatic compound it is preferred that the substitution position is directly on the ring and with an olefinic compound it is preferred that the substitution position is at a vinylic position. If the organic compound is a polymer or a dendrimer it may have many substitution positions.

As used herein, the term "leaving group" refers to a chemical group which is capable of being displaced by a boronic acid residue. Suitable leaving groups are apparent to those skilled in the art and include halogen and halogen-like substituents, as well as ester groups.

In this specification "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, isocyano, cyano, formyl, carboxyl, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, imino, alkylimine, alkenylimine, alkynylimino, arylimino, benzylimino, dibenzylamino, acyl, alkenylacyl, alkynylacyl, arylacyl, acylamino, diacylamino, acyloxy, alkylsulphonyloxy, arysulphenyloxy, heterocyclyl, heterocycloxy, heterocyclamino, haloheterocyclyl, alkylsulphenyl, arylsulphenyl, carboalkoxy, carboaryloxy mercapto, alkylthio, benzylthio, acylthio, sulphonamido, sulfanyl, sulfo and phosphorus-containing groups, alkoxysilyl, silyl, alkylsilyl, alkylalkoxysilyl, phenoxysilyl, alkylphenoxysilyl, alkoxyphenoxy silyl and arylphenoxy silyl.

The olefinic compound (i) must include at least one halogen or halogen-like substituent at a vinylic coupling position to enable reaction with the disubstituted monohydroborane.

Similarly the organic compound must have at least one halogen or halogen-like substituent at a coupling position to enable reaction with the alkene borate intermediate. Preferred halogen substituents include I, Br and Cl. The reactivity of chloro substituted compounds can be increased by selection of appropriate ligands on the Group 8–11 metal catalyst. The terms "halogen-like substituent" and "pseudohalide" refer to any substituent which, if present, may undergo substitution with a disubstituted monohydroborane in the presence of a Group 8–11 metal catalyst and base to give an aryl or alkene borate, or if present on an organic compound may undergo substitution with an aryl or alkene borate to give a coupled product. Examples of halogen-like substituents include triflates and mesylates, diazonium salts, phosphates and those described in Palladium Reagents & Catalysts (Innovations in Organic Synthesis by J. Tsuji, John Wiley & Sons, 1995, ISBN 0-471-95483-7).

The process according to the present invention is especially suitable for the formation of aryl and alkene borates from aromatic or olefinic compounds containing active hydrogen containing substituents. The term "active hydrogen containing substituent" as used herein refers to a substituent which contains a reactive hydrogen atom. Examples of such substituents include but are not limited to hydroxy, amino, imino, acetyleno, carboxy (including carboxylato), carboximidyl, sulfo, sulfinyl, sulfinimidyl, sulfinohydroximyl, sulfonimidyl, sulfondiimidyl, sulfonohydroximyl, sultamyl, phosphinyl, phosphinimidyl, phosphonyl, dihydroxyphosphanyl, hydroxyphosphanyl, phosphono (including phosphonato), hydrohydroxyphosphoryl, allophanyl, guanidino, hydantoyl, ureido, and ureylene. Of these substituents it is particularly surprising that the reaction can be conducted with hydroxy and amino substituents. Additional disubstituted monohydroboranes may be required for those compounds containing substituents with active hydrogens. An additional advantage of the process of this invention is its ability to solubilise starting material in situ.

While the present invention allows the reaction of compounds with active hydrogen containing substituents without prior protection, it is also possible, and sometimes advantageous, to do so. The use of protecting groups can reduce the amount of disubstituted monohydroborane required to perform the boronation reaction. Examples of suitable hydroxy protecting groups are described in Protective Group in Org Synthesis, T. W. Green & P Wuts J Wiley & Son 2nd Edition 1991. In a particularly preferred embodiment the active hydrogen compound is reacted with a borane compound, such as one of the polyhydroboranes described above, for example with a phenolic compound having halogen or halogen-like substituent. The triester of the phenol can be formed using a borane compound, such as borane methylsulphide adduct, which ester can be used as the reactant in a subsequent boronation reaction. If the pinacol or other ester of the arylboronic acid species is not sought in the first instance (these can be made by subsequent esterification/transesterification) the diester of the borane with the phenol can be made and then used as the boronation reagent. As an alternative, a borate ester can be partially or completely transesterified with, for example, a phenolic aryl halide and this species can be used as a reactant in the subsequent boronation reaction. Boric acid can also be used to remove the active hydrogen by formation of the triester, with for example, an aryl halide containing an hydroxy (phenolic) group.

This concept can be extended to other reactants containing active hydrogen substituents, although it should be noted that borane reactants generally do not react with the active hydrogen groups of primary or secondary amides.

One method for preparing olefinic compounds having a halogen-like substituent in a vinylic substitution position is by the conversion of a carbonyl group with a β-hydrogen into a trapped enol form, this enol being useful in the process of the present invention. This is achieved by trapping the enol with a mesylate or triflate group or the like. This enol is then reacted with the disubstituted monohydroborane in the presence of a Group 8–11 metal catalyst and a suitable base to form the vinylic boronate.

It has also been unexpectedly found that the induction time required for the reaction of the olefinic or aromatic ring compound with the disubstituted monohydroborane can be substantially reduced by the addition of a promoter.

Accordingly in a further aspect of the present invention there is provided a process for the synthesis of an alkene or aryl borate which comprises reacting:
(i) an olefinic compound having a halogen or halogen-like substituent in a vinylic substitution position, or
(ii) an aromatic ring compound having a halogen or halogen-like substituent in a ring substitution position, with a disubstituted monohydroborane, in the presence of a Group 8–11 metal catalyst, a suitable base and a promoter such that a borane residue is introduced at the substitution position.

The promoter may be any suitable compound or reagent which is capable of increasing the rate of reaction between an olefinic or aromatic ring compound and a disubstituted monohydroborane in the presence of a Group 8–11 metal catalyst and a suitable base. The promoter may be an amide. Examples of suitable amide promoters include p-iodoacetanilide, acetanlide, acetamide and N-methylacetamide.

The use of a promoter is particularly advantageous in the reaction of aromatic ring compounds having electron withdrawing groups, or in the reaction of olefinic compounds.

It has also been found that the catalyst activity can be increased, prior to its use in the reaction, by treatment with a suitable base or mixture of bases. Organic amines are suitable bases for this treatment. Besides the enhancement of the reaction rate this catalyst treatment has the further advantage that side product formation is reduced. In particular, this catalyst treatment reduces the extent of substrate dehalogenation, increases the yield of the required organic boronic acid derivative and reduces the amount of the arylboronic acid derivative in which the aryl group is derived from a ligand on the catalyst.

It is of advantage to carry out the activation of the catalyst with base(s) before the contacting of the disubstituted monohydroborane with the catalyst. This activation may be achieved by heating the catalyst with base(s). The base may be the amine used to promote the boronation reaction. The temperature and reaction time required for activation will vary with catalyst composition, the nature of the base and also the solvent. The catalyst should be treated to such an extent that there is little or no induction time in the subsequent boronation reaction. For some catalysts there is a colour change as activation occurs. The activated catalyst may be stored for subsequent use in the boronation reaction or can be used immediately following activation, without isolation from the base with which it is heated.

According to this aspect of the invention there is provided a process for the synthesis of an alkene or aryl borate which comprises reacting (i) an olefinic compound having a halogen or halogen-like substituent in a vinylic substitution position, or (ii) an aromatic ring compound having a halogen or halogen-like substituent in a ring substitution position, with a disubstituted monohydroborane, in the presence of a Group 8–11 metal catalyst and a suitable base such that a borane residue is introduced at the substitution position, wherein the Group 8–11 metal catalyst is activated by treatment with an organic amine prior to contacting of the disubstituted monohydroborane with the catalyst.

In the above definitions, the term "alkyl", used either alone or in compound words such as "alkenyloxyalkyl", "alkylthio", "alkylamino" and "dialkylamino" denotes straight chain, branched or cyclic alkyl, preferably $C_{1-20}$ alkyl or cycloallyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

The term "alkoxy" denotes straight chain or branched alkoxy, preferably $C_{1-20}$ alkoxy. Examples of alkoxy include methoxy, ethoxy, n-propoxy, isopropoxy and the different butoxy isomers.

The term "alkenyl" denotes groups formed from straight chain, branched or cyclic alkenes including ethylenically mono-, di- or poly-unsaturated alkyl or cycloalkyl groups as previously defined, preferably $C_{2-20}$ alkenyl. Examples of alkenyl include vinyl, allyl, 1-methylvinyl, butenyl, isobutenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

The term "alkynyl" denotes groups formed from straight chain, branched or cyclic alkyne including those structurally similar to the alkyl and cycloalkyl groups as previously defined, preferably $C_{2-20}$ alkynyl. Examples of alkynyl include ethynyl, 2-propynyl and 2- or 3-butynyl.

The term "acyl" either alone or in compound words such as "acyloxy", "acylthio", "acylamino" or "diacylamino" denotes carbamoyl, aliphatic acyl group and acyl group containing an aromatic ring, which is referred to as aromatic acyl or a heterocyclic ring which is referred to as heterocyclic acyl, preferably $C_{1-20}$ acyl. Examples of acyl include carbamoyl; straight chain or branched alkoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl, cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

The terms "heterocyclic", "heterocyclyl" and "heterocycl" as used herein on their own or as part of a term such as "heterocyclicalkenoyl", "heterocycloxy" or "haloheterо- cyclyl" refer to aromatic, pseudo-aromatic and non-aromatic rings or ring systems which contain one or more heteroatoms selected from N, S, and O and which may be optionally substituted. Preferably the rings or ring systems have 3 to 20 carbon atoms. The rings or ring systems may be selected from those described above in relation to the definition of "aromatic ring compound(s)".

The term "aryl" as used herein on its own or as part of a group such as "haloaryl" and "aryloxycarbonyl" refers to aromatic and pseudo-aromatic rings or ring systems composed of carbon atoms, optionally together with one or more heteroatoms. Preferably the rings or ring systems have between 3 and 20 carbon atoms. The rings or ring systems may be optionally substituted and may be selected from those described above in relation to the definition of "aromatic ring compound(s)".

Examples of suitable monohydroboranes include those of the formula $(RX)_2B$—H where each X is independently selected from O, S and NR" where R" is H, an optionally substituted alkyl or optionally substituted aryl and each R is independently selected from optionally substituted alkyl and optionally substituted aryl or where —$B(XR)_2$ represents a cyclic group of formula II

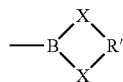

where R' is optionally substituted alkylene, arylene or other divalent group comprising linked aliphatic or aromatic moieties and X is as defined above. Preferred disubstituted monohydroboranes are dialkoxy hydroboranes including 4,4-dimethyl-1,3,2-dioxaborinane, 4,4,6-trimethyl-1,3,2-dioxaborinane, 4,4,6,6-tetramethyl-1,3,2-dioxaborinane, 4,4-dimethyl-1,3,2-dioxaborolane, 4,4,5-trimethyl-1,3,2-dioxaborolane, 4,4,5,5-tetramethyl-1,3,2-dioxaborolane, 4-phenyl-1,3,2-dioxaborinane, n-propanediolborane (1,3,2-dioxaborinane), 5,5-dimethyl-1,3,2-dioxaborinane, (4R,5R)-4,5-bis(1-methoxy-1-methylethyl)-1,3,2-dioxaborolane, (4S,5S)-4,5-bis(1-methoxy-1-methylethyl)-1,3,2-dioxaborolane, dinaphtho[2,1-d:1,2-f][1,3,2]dioxaborepine, (4R,5R)-3,4-dimethyl-5-phenyl-1,3,2-oxazaborolidine, (4S,5S)-3,4-dimethyl-5-phenyl-1,3,2-oxazaborolidine, (4R,5R)-3-isopropyl-4-methyl-5-phenyl-1,3,2-oxazaborolidine and (4S,5S)-3-isopropyl-4-methyl-5-phenyl-1,3,2-oxazaborolidine. Some preferred disubstituted monohydroboranes which are novel and represent a further aspect of the invention are (4R,5R)-4,5-dimethyl-1,3,2-dioxaborolane, (4S,5S)-4,5-dimethyl-1,3,2-dioxaborolane, (4R,5R)-4,5-diphenyl-1,3,2-dioxaborolane, (4S,5S)-4,5-diphenyl-1,3,2-dioxaborolane, (4S)-4-(methoxymethyl)-1,3,2-dioxaborolane, (4R)-4-(methoxymethyl)-1,3,2-dioxaborolane, tetrahydro-3aH-cyclopenta[d][1,3,2]dioxaborole, 3-methyl-1,3,2-oxazaborolidine, (6R)-4,4,6-trimethyl-1,3,2-dioxaborinane, (6S)-4,4,6-trimethyl-1,3,2-dioxaborinane, hexahydro-1,3,2-benzodioxaborole, (4R,5R)-4,5-bis(methoxymethyl)-1,3,2-dioxaborolane, (4S,5S)-4,5-bis(methoxymethyl)-1,3,2-dioxaborolane, (4R,5R)-4,5-dicyclohexyl-1,3,2-dioxaborolane, (4S,5S)-4,5-dicyclohexyl-1,3,2-dioxaborolane, (5R)-4,4-dimethyl-5-phenyl-1,3,2-dioxaborolane, (5S)-4,4-dimethyl-5-phenyl-1,3,2-dioxaborolane, (4R)-4-phenyl-1,3-dioxa-2-boraspiro[4.4]nonane, (4S)-4-phenyl-1,3-dioxa-2-boraspiro[4.4]nonane, (4S,5S)-4,5-bis(1-methoxycyclopentyl)-1,3,2-dioxaborolane, (4R,5R)-4,5-bis(1-methoxycyclopentyl)-1,3,2-dioxaborolane, diisopropyl (4S,5S)-1,3,2-dioxaborolane-4,5-dicarboxylate, diisopropyl (4R,5R)-1,3,2-dioxaborolane-4,5-dicarboxylate, (1R,2S,6S,7S)-1,10,10-trimethyl-6-phenyl-3,5-dioxa-4-boratricyclo[5.2.1.0$^{2,6}$]decane, (1S,2R,6R,7R)-1,10,10-trimethyl-6-phenyl-3,5-dioxa-4-boratricyclo[5.2.1.0$^{2,6}$]decane, (3aR)-3a-methyl-3,3-di(2-naphthyl)tetrahydro-3H-pyrrolo[1,2-c][1,3,2]oxazaborole, (3aS)-3a-methyl-3,3-di(2-naphthyl)tetrahydro-3H-pyrrolo[1,2-c][1,3,2]oxazaborole, (3aR)-3,3-di(2-naphthyl)tetrahydro-3H-pyrrolo[1,2-c][1,3,2]oxazaborole (3aS)-3,3-di(2-naphthyl)tetrahydro-3H-pyrrolo[1,2-c][1,3,2]oxazaborole, (4S,5S)-4,5-bis[(4R)-2,2-dimethyl-1,3-dioxolan-4-yl]-1,3,2-dioxaborolane, (4R,5R)-4,5-bis[(4S)-2,2-dimethyl-1,3-dioxolan-4-yl]-1,3,2-dioxaborolane, (2R)-2-{(4S,5S)-5-[(2R)-1,4-dioxaspiro[4.5]dec-2-yl]-1,3,2-dioxaborolan-4-yl}-1,4-dioxaspiro[4.5]decane, (2S)-2-{(4R,5R)-5-[(2S)-1,4-dioxaspiro[4.5]dec-2-yl]-1,3,2-dioxaborolan-4-yl}-1,4-dioxaspiro[4.5]decane, (4S,5S)-N$^4$,N$^4$,N$^5$,N$^5$-tetramethyl-1,3,2-dioxaborolane-4,5-dicarboxamide, (4R,5R)-N$^4$,N$^4$,N$^5$,N$^5$-tetramethyl-1,3,2-dioxaborolane-4,5-dicarboxamide, (1R,2R,6S,8R)-2,9,9-trimethyl-3,5-dioxa-4-boratricyclo[6.1.1.0$^{2,6}$]decane and (1S,2S,6R,8S)-2,9,9-trimethyl-3,5-dioxa-4-boratricyclo[6.1.1.0$^{2,6}$]decane.

Some of the hydroborane derivatives will be more readily amenable to subsequent hydrolysis than others and may allow for the use of milder reaction conditions. Furthermore, judicious choice of the hydroborane derivative used may facilitate control over the reaction products formed. The dioxyhydroborane derivatives may be made following the method of Tucker, C. E. et al, J. Org Chem, 1992, 57, 3482–3485, Contreras, R. et al, Spectrochimica Acta 1984 40A 855 or Bello-Ramírez, M. A., Rodríguez Martínez, M. E., and Flores-Parra, A., Heteroatom Chem., 1993, 4, 613. Other methods for the preparation of the hydroborane derivatives will be known to those in the art.

The present invention also provides a route to some chiral compounds. Chiral aryl and alkene borates may be prepared using chiral disubstituted monohydroboranes. If the chiral monohydroborane has an enantiomeric excess of one enantiomer over another, this can produce chiral aryl and alkene borates having a corresponding enantiomeric excess. The chirality of an aryl or alkene borate may also be transferred to a coupled product. Chiral products may also be achieved using chiral catalysts.

The term "Group 8–11 metal catalyst" as used herein refers to a catalyst comprising a metal of Groups 8–11 of the periodic table described in Chemical and Engineering News, 63(5), 27, 1985. Examples of such metals include Ni, Pt and Pd. Preferably the catalyst is a palladium catalyst, although analogous catalysts of other Group 8–11 metals may also be used.

Examples of suitable palladium catalysts include but are not limited to $Pd_3(dba)_3$, $PdCl_2$, $Pd(OAc)_2$, $PdCl_2(dppf)$ $CH_2Cl_2$, $Pd(PPh_3)_4$ and related catalysts which are complexes of phosphine ligands, (such as $(Ph_2P(CH_2)_nPPh_2)$ where n is 2 to 5, $P(o-tolyl)_3$, $P(i-Pr)_3$, $P(cyclohexyl)_3$, $P(o-MeOPh)_3$, $P(p-MeOPh)_3$, dppp, dppb, TDMPP, TTMPP, TMPP, TMSPP, 2-(di-t-butylphosphino)biphenyl, (R,R)-Me-DUPHOS, (S,S)-Me-DUPHOS, (R)-BINAP, (S)-BINAP, and related water soluble phosphines), related ligands (such as triarylarsine, triarylantimony, triarylbismuth), phosphite ligands (such as $P(OEt)_3$, $P(O-p-tolyl)_3$, $P(O-o-tolyl)_3$, $P(O-iPr)_3$, tris(2,4-di-t-butylphenyl)phosphite and other examples described in the STREM Catalogue No. 18 (Chemicals for Research: metals, inorganics and organometallics 1999–2001)) and other suitable ligands including those containing P and/or N atoms for coordinating to the palladium atoms, (such as for example pyridine, alkyl and aryl substituted pyridines, 2,2'-bipyridyl, alkyl substituted 2,2'-bipyridyl and bulky secondary or tertiary amines), and other simple palladium salts either in the presence or absence of ligands. The palladium catalysts include palladium and palladium complexes supported or tethered on solid supports, such as palladium on carbon, as well as palladium black, palladium clusters and palladium clusters containing other metals and palladium in porous glass as described in J. Li, A. W-H. Mau and C. R. Strauss, Chemical Communications, 1997, p 1275. The same or different Group 8–11 metal catalysts may be used to catalyse different steps in the process. It can be an advantage to select a catalyst with ligands that cannot exchange aryl groups with the aromatic ring compound or that minimise this exchange.

The Group 8–11 metal catalyst may be a platinum complex. Examples of suitable platinum catalysts include but are not limited to $Pt(dba)_2$, $Pt(PPh_3)_2Cl_2$, $PtCl_2$, $Pt(OAc)_2$, $PtCl_2(dppf)CH_2Cl_2$, $Pt(PPh_3)_4$ and related catalysts which are complexes of phosphine ligands, (such as $(Ph_2P(CH_2)_nPPh_2)$ where n is 2 to 5, $P(o\text{-tolyl})_3$, $P(i\text{-Pr})_3$, $P(cyclohexyl)_3$, $P(o\text{-MeOPh})_3$, $P(p\text{-MeOPh})_3$, dppp, dppb, TDMPP, TTMPP, TMPP, TMSPP, 2-(di-t-butylphosphino)biphenyl, (R,R)-Me-DUPHOS, (S,S)-Me-DUPHOS, (R)-BINAP, (S)-BINAP and related water soluble phosphines), related ligands (such as triarylarsine, triarylantimony, triarylbismuth), phosphite ligands (such as $P(OEt)_3$, $P(O\text{-p-tolyl})_3$, $P(O\text{-o-tolyl})_3$, $P(O\text{-iPr})_3$, tris(2,4-di-t-butylphenyl)phosphite and other examples described in the STREM Catalogue No. 18 (Chemicals for Research: metals, inorganics and organometallics 1999–2001)) and other suitable ligands including those containing P and/or N atoms for coordinating to the platinum atoms, (such as for example pyridine, alkyl and aryl substituted pyridines, 2,2'-bipyridyl, alkyl substituted 2,2'-bipyridyl and bulky secondary or tertiary amines), and other simple platinum salts either in the presence or absence of ligands. The platinum catalysts include platinum and platinum complexes supported or tethered on solid supports, such as platinum on carbon, as well as platinum black, platinum clusters and platinum clusters containing other metals.

The Group 8–11 metal catalyst may also be selected from those described in U.S. Pat. No. 5,686,608. In certain reactions there are advantages in using ligands with altered basicity and/or steric bulk. Examples of suitable Ni catalysts include nickel complex, Raney nickel, nickel on carbon and nickel clusters or a nickel black. Preferred catalysts are those that readily undergo oxidative addition and reductive elimination. One skilled in the art would be able to select a suitable catalyst on this basis. Catalysts of palladium are preferred. The Group 8–11 metal catalyst may contain other metals.

Suitable catalysts also include metallocyclic compounds and compounds that can form metallocyclic species in situ in the reaction medium.

The catalysts according to the present invention may be prepared in situ. For example catalysts consisting of phosphine complexes of palladium can be prepared in situ by addition of a palladium (II) salt such as the acetate and the desired mono- or di-phosphine in a ratio such that the Pd/P atom ratio is approximately 1:2. Arsines, such as for example bis(diphenylarsino) ethane and the like can also be used in conjunction with Pd to make active catalysts for the boronation of aryl halide type species.

The process for preparing the boronates may be performed in any suitable solvent or solvent mixture. Examples of such solvents include lower alkyl esters of the lower aliphatic carboxylic acids, cyclic and the lower secondary and tertiary amines, amides of the lower aliphatic carboxylic acids and lower aliphatic secondary amines, aromatic or aliphatic hydrocarbons, acetonitrile, benzonitrile, ethers, polyethers, cyclic ethers, lower aromatic ethers, and mixtures thereof, including mixtures with other solvents.

Preferred solvents include n-heptane, DMA, DMSO, 1,2-dichlorethane, toluene, acetonirile, dioxane, DME, diethyl ether, THF or mixtures thereof with other solvents. The addition of further disubstituted monoborane derivative may be useful when the solvents are not anhydrous.

The temperature at which each step of the process according to the invention is conducted will depend on a number of factors including the desired rate of reaction, solubility and reactivity of the reactants in the selected solvent, boiling point of the solvent, etc. The temperature of the reaction will generally be in the range of −100 to 250° C. In a preferred embodiment the process is performed at a temperature between 0 and 120° C., more preferably between 15 and 80° C.

The term "suitable base" as used herein refers to a basic compound which, when present in the reaction mixture, is capable of catalysing, promoting or assisting reaction between reactants. The base may be suitable for promoting a single step, or more than one step, depending on the desired outcome of the reaction. For example a base may be chosen which promotes reaction between the olefinic or aromatic compound and the disubstituted monohydroborane, but which is not strong enough under the conditions used in the reaction to promote further reaction of the aryl or alkene borate with additional aryl or olefinic compound, or other organic compound. It is also preferable that a base is chosen which is soluble in the solvent to which it is added. Examples of bases which are suitable for promoting the reaction of the olefinic or aromatic compound with the disubstituted monohydroborane include secondary amines, tertiary amines, aliphatic cyclic amines and amines bearing a second or more hetero atom. Some of these bases may be used in conjunction with a phase transfer reagent, such as for example tetraalkylammonium salts or the crown ethers.

Examples of bases suitable for catalysing reaction of the olefinic or aromatic compounds with the disubstituted monoborane, without generally catalysing the further reaction of the aryl or alkene intermediate include triethylamine, and other N-bases.

Bases that can be used to activate the catalyst prior to use in the reaction are preferably chosen from secondary amines, tertiary amines, aromatic amines, aliphatic cyclic amines and amines bearing a second or more hetero atom.

Examples of bases that can be used to promote the catalytic activity of the catalyst by treatment with the base(s) prior to use in the reaction include but are not limited to triethylamine, 2,6-dimethylpiperidine and N-methylpiperidine.

Examples of compounds suitable for decomposing excess disubstituted monohydroborane include water, alcohols and acids.

As used herein the terms "alkene borate" and "aryl borate" refer to the products of the Group 8–11 metal base catalysed reaction between an olefinic or aromatic compound respectively and the disubstituted monoborane, the product including a carbon-to-boron bond at the substitution position.

In a further aspect of the invention there is provided a process for the preparation of an aromatic or olefinic boronic acid by hydrolysing the aryl or alkene borate as hereinbefore described using established procedures. The ease of hydrolysis is a function of the disubstituted monoborane used. Some aryl and alkene borates are more amenable to hydrolysis than those derived from pinacolborane.

Some of the aryl and alkene borates and boronic acids are novel and represent a further aspect of the present invention. Some of these novel compounds are as follows:

4-methoxy-3-(4,4,5,5-tetramethyl-1,3,2-dioxaborolan-2-yl) benzoic acid,
4-Hydroxy-3-(4,4,5,5-tetramethyl-1,3,2-dioxaborolan-2-yl) phenylalanine,
3-(4,4,5,5-Tetramethyl-1,3,2-dioxaborolan-2-yl)benzoic acid,
3-Methyl-4-(4,4,5,5-tetramethyl-1,3,2-dioxaborolan-2-yl) benzoic acid,
5-(4-Phenyl-1,3,2-dioxaborolan-2-yl)-1,3-benzodioxole,
5-(4,5-Dimethyl-1,3,2-dioxaborolan-2-yl)-1,3-benzodioxole,
5-(4,5-Diphenyl-1,3,2-dioxaborolan-2-yl)-1,3-benzodioxole,
5-[4-(Methoxymethyl)-1,3,2-dioxaborolan-2-yl]-1,3-benzodioxole,
5-Tetrahydro-3aH-cyclopenta[d][1,3,2]dioxaborol-2-yl-1,3-benzodioxole,
5-(4,4,6-Trimethyl-1,3,2-dioxaborinan-2-yl)-1,3-benzodioxole,
5-(4,4,6,6-Tetramethyl-1,3,2-dioxaborinan-2-yl)-1,3-benzodioxole,
2-(1,3-Benzodioxol-5-yl)-3-methyl-1,3,2-oxazaborolidine,
2-[(1S,2S,6R,8S)-2,9,9-Trimethyl-3,5-dioxa-4-boratricyclo[6.1.1.0$^{2,6}$]dec-4-yl]benzonitrile,
(1S,2S,6R,8S)-4-(4-Methoxy-2-methylphenyl)-2,9,9-trimethyl-3,5-dioxa-4-boratricyclo[6.1.1.0.0$^{2,6}$]decane,
2,6-Dimethoxy-3-[(1S,2S,6R,8S)-2,9,9-trimethyl-3,5-dioxa-4-boratricyclo[6.1.1.0$^{2,6}$]dec-4-yl]pyridine,
(1S,2S,6R,8S)-2,9,9-Trimethyl-4-(2,3,4-trimethoxyphenyl)-3,5-dioxa-4-boratricyclo[6.1.1.0$^{2,6}$]decane,
(1S,2S,6R,8S)-4-(2-Methoxyphenyl)-2,9,9-trimethyl-3,5-dioxa-4-boratricyclo[6.1.1.0$^{2,6}$]decane,
(1S,2S,6R,8S)-2,9,9-Trimethyl-4-[2-(trifluoromethyl)phenyl]3,5-dioxa-4-boratricyclo[6.1.1.0$^{2,6}$]decane,
(1S,2S,6R,8S)-2,9,9-Trimethyl-4-(2-methylphenyl)-3,5-dioxa-4-boratricyclo[6.1.1.0$^{2,6}$]decane,
2-[(1R,2R,6S,8R)-2,9,9-Trimethyl-3,5-dioxa-4-boratricyclo[6.1.1.0$^{2,6}$]dec-4-yl]benzonitrile,
(1R,2R,6S,8R)-4-(4-Methoxy-2-methylphenyl)-2,9,9-trimethyl-3,5-dioxa-4-boratricyclo[6.1.1.0$^{2,6}$]decane,
2,6-Dimethoxy-3-[(1R,2R,6S,8R)-2,9,9-trimethyl-3,5-dioxa-4-boratricyclo[6.1.1.0$^{2,6}$]dec-4-yl]pyridine,
(1R,2R,6S,8R)-2,9,9-Trimethyl-4-(2,3,4-trimethoxyphenyl)-3,5-dioxa-4-boratricyclo[6.1.1.0$^{2,6}$]decane,
(1R,2R,6S,8R)-4-(2-Methoxyphenyl)-2,9,9-trimethyl-3,5-dioxa-4-boratricyclo[6.1.1.0$^{2,6}$]decane,
(1R,2R,6S,8R)-2,9,9-Trimethyl-4-[2-(trifluoromethyl)phenyl]-3,5-dioxa-4-boratricyclo[6.1.1.0$^{2,6}$]decane,
(1R,2R,6S,8R)-2,9,9-Trimethyl-4-(2-methylphenyl)-3,5-dioxa-4-boratricyclo[6.1.1.0$^{2,6}$]decane,
2-(4,4,5,5-Tetramethyl-1,3,2-dioxaborolan-2-yl)phenol,
4-(4,4,5,5-Tetramethyl-1,3,2-dioxaborolan-2-yl)phenol,
3,4-Dimethoxy-5-(4,4,5,5-tetramethyl-1,3,2-dioxaborolan-2-yl)benzaldehyde,
Ethyl 2-(4,4,5,5-tetramethyl-1,3,2-dioxaborolan-2-yl)benzoate,
Ethyl 3-(4,4,5,5-tetramethyl-1,3,2-dioxaborolan-2-yl)benzoate,
1,3-Dimethyl-5-(4,4,5,5-tetramethyl-1,3,2-dioxaborolan-2-yl)-2,4(1H,3H)-pyrimidinedione,
Ethyl 4-methoxy-3-(4,4,5,5-tetramethyl-1,3,2-dioxaborolan-2-yl)benzoate,
4,4,5,5-Tetramethyl-2-(2,4,6-trichlorophenyl)-1,3,2-dioxaborolane,
Methyl 2-(acetylamino)-5-(4,4,5,5-tetramethyl-1,3,2-dioxaborolan-2-yl)benzoate,
Phenyl[4-(4,4,5,5-tetramethyl-1,3,2-dioxaborolan-2-yl)phenyl]methanone,
4,4,5,5-Tetramethyl-2-(2,4,6-trimethoxyphenyl)-1,3,2-dioxaborolane,
2-(2-Methoxy-1-naphthyl)-4,4,5,5-tetramethyl-1,3,2-dioxaborolane,
2-(2-Bromophenyl)-4,4,5,5-tetramethyl-1,3,2-dioxaborolane,
4,4,5,5-Tetramethyl-2-[2-(4,4,5,5-tetramethyl-1,3,2-dioxaborolan-2-yl)phenyl]-1,3,2-dioxaborolane,
3-(4,4,5,5-Tetramethyl-1,3,2-dioxaborolan-2-yl)benzylamine,
4,4,5,5-Tetramethyl-2-(2,3,4,6-tetramethoxyphenyl)-1,3,2-dioxaborolane,
N-[2-Methyl-4-(4,4,5,5-tetramethyl-1,3,2-dioxaborolan-2-yl)phenyl]acetamide,
2-(6-Methoxy-2-naphthyl)-4,4,5,5-tetramethyl-1,3,2-dioxaborolane,
2,4-Dimethoxy-5-(4,4,5,5-tetramethyl-1,3,2-dioxaborolan-2-yl)pyrimidine,
2-(2-Fluoro[1,1'-biphenyl]-4-yl)-4,4,5,5-tetramethyl-1,3,2-dioxaborolane,
2-(4-Methoxy-1-naphthyl)-4,4,5,5-tetramethyl-1,3,2-dioxaborolane,
4-[4-(4,4,5,5-Tetramethyl-1,3,2-dioxaborolan-2-yl)phenyl]-1,3-thiazol-2-amine,
4,4,5,5-Tetramethyl-2-(4-{[(E)-3-methyl-1-butenyl]oxy}phenyl)-1,3,2-dioxaborolane,
1-[4'-(4,4,5,5-Tetramethyl-1,3,2-dioxaborolan-2-yl)[1,1'-biphenyl]4-yl]-1-ethanone,
3-Bromo-6-(4,4,5,5-tetramethyl-1,3,2-dioxaborolan-2-yl)-9H-carbazole,
6-(4,4,5,5-Tetramethyl-1,3,2-dioxaborolan-2-yl)-2-naphthol,
2-Methoxy-4-(4,4,5,5-tetramethyl-1,3,2-dioxaborolan-2-yl)-phenol,
2-Methoxy-5-(4,4,5,5-tetramethyl-1,3,2-dioxaborolan-2-yl)-phenol,
2-(4,4,5,5-Tetramethyl-1,3,2-dioxaborolan-2-yl)aniline,
5-(4,4,5,5-Tetramethyl-1,3,2-dioxaborolan-2-yl)-1H-indole,
2,6-Dimethyl-4-(4,4,5,5-tetramethyl-1,3,2-dioxaborolan-2-yl)phenol,
5-(4,4,5,5-Tetramethyl-1,3,2-dioxaborolan-2-yl)-1H-indole,
4,4,5,5-Tetramethyl-2-(4-phenoxyphenyl)-1,3,2-dioxaborolane,
N-[2-Fluoro-4-(4,4,5,5-tetramethyl-1,3,2-dioxaborolan-2-yl)phenyl]acetamide,
Ethyl 2-[4-(4,4,5,5-tetramethyl-1,3,2-dioxaborolan-2-yl)phenoxy]acetate,
4-Hydroxy-3-(4,4,5,5-tetramethyl-1,3,2-dioxaborolan-2-yl) phenylalanine and
3-(4,4,5,5-Tetramethyl-1,3,2-dioxaborolan-2-yl)aniline.

The process according to the present invention is applicable to chemistry on solid polymer support or resin bead in the same manner as conventional chemistry is used in combinatorial chemistry and in the preparation of chemical libraries. Thus a suitably substituted olefinic or aromatic ring compound linked to a polymer surface is reacted with a disubstituted monohydroborane in the presence of a Group 8–11 metal catalyst and a suitable base to form an alkene or aryl borate chemically linked to the polymer surface. This borate may then be reacted with an organic compound having a halogen or halogen-like substituent at a coupling position in the presence of a Group 8–11 metal catalyst and a suitable base to prepare the coupled product chemically linked to the polymer. Excess reactants and by-products may be removed by suitable washing and the coupled product may be isolated by chemically cleaving the link to the polymer. The process is also possible using the alternative strategy where an organic compound having a halogen or halogen-like substituent at a coupling position which is chemically linked to a polymer surface is reacted with an aryl or alkene borate prepared in accordance with the present invention in the presence of a Group 8–11 metal catalyst and a suitable base to form a coupled product linked to the surface of the polymer. Excess reagents and by-products may then be washed away from the surface leaving only the reaction product on the surface. The coupled product may then be isolated by appropriate cleavage of the chemical link from the polymer surface.

It is also possible to prepare polymers by reaction of olefinic or aromatic compounds having more than one boron reactive substituent. Such compounds may be reacted with a disubstituted monohydroborane in the presence of a Group 8–11 metal catalyst and a suitable base to form an aryl or alkene borate having more than one boron functionality. These intermediates may be reacted with organic compounds having more than one halogen or halogen-like substituent to form a polymer. If the olefinic or aromatic ring compound has three or more halogen or halogen-like substituents which react with the disubstituted monohydroborane then it is possible to prepare dendritic molecules in accordance with the process of the present invention.

The olefinic or aromatic ring compound and the organic compound may be separate molecules, or may be linked together such that the aryl or alkene borate formed after reaction with the disubstituted monohydroborane is able to react at a coupling position located elsewhere in the molecule so as to provide for an intramolecular reaction, such as a ring closure reaction.

The process according to the invention is also useful for the preparation of reactive intermediates which, after coupling, take part in further reactions or rearrangements. An example of such an intermediate is one formed by reaction of an ether containing vinylic halide with one of $R^1$, $R^2$ or $R^3$ (formula I) being —OR with a disubstituted monohydroborane. The subsequent coupling of the resulting alkene borate intermediate with an organic compound gives a ketone on hydrolysis of the enol ether.

The following examples are provided to illustrate preferred embodiments of the invention. However it is to be understood that the following description is not to supersede the generality of the invention previously described.

EXAMPLES

Example 1

Formation of 4-(4,4,5,5-tetramethyl-1,3,2-dioxaborolan-2-yl)phenol

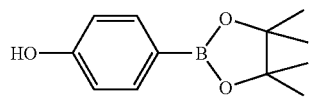

To 24.5 mg $PdCl_2(dppf).CH_2Cl_2$ in a reaction tube under nitrogen were added 4 ml dioxane, 0.42 ml (3 mmol) triethylamine, 0.35 ml (2.4 mmol) pinacolborane and 221 mg (1.0 mmol) p-iodophenol. The reaction solution was stirred at room temp. to ensure that all the phenolic groups had reacted with pinacolborane and the hydrogen evolved was flushed out of the reaction tube with argon. The crimson coloured reaction solution was warmed to 80° C. with stirring in an oil bath. The colour of the solution changed to a pale orange and after 2 h the reaction solution had darkened. After 8 h an aliquot was removed, extracted into ethyl acetate, washed several times with water and analysed by gc (fid detector, SGE HT5 capillary column). No p-iodophenol was found in the solution analysed indicating that the reaction had gone to completion. Only 3 peaks were observed in the gc, other than the solvent, and these were shown by gc/ms to be due to phenol and the pinacol esters of phenylboronic acid and the desired hydroxyphenylboronic acid and their concentrations, based on the gc peak areas, uncorrected for fid response, were 14%, 7% and 78% respectively. The phenylboronic acid ester is thought to have formed through aryl exchange on the phosphorus atoms of the catalyst ligand.

Example 2

Formation of 4-methoxy-3-(4,4,5,5-tetramethyl-1,3,2-dioxaborolan-2-yl)benzoic acid

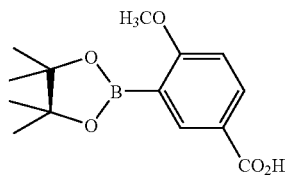

To 26.9 mg $PdCl_2(dppf).CH_2Cl_2$ in a reaction tube under nitrogen were added 4 ml dioxane, 0.43 ml (3 mmol) triethylamine, 0.35 ml (2.4 mmol) pinacolborane and 277 mg (1.0 mmol) 3-iodo-4-methoxybenzoic acid. The reaction solution was stirred at room temp. to ensure that all the phenolic groups had reacted with pinacolborane and the hydrogen evolved was flushed out of the reaction tube with argon. The reaction solution was warmed to 80° C. with stirring in an oil bath for 8 h. An aliquot (0.3 ml) was removed from the reaction solution, extracted into ethyl acetate, washed with dilute sulphuric acid and then several times with water and analysed by gc (fid detector, SGE HT5 capillary column). There was only one peak in the gc at retention time longer than that for 3-iodo-4-methoxybenzoic acid and that was confirmed by gc/ms to be due to the desired arylboronic acid pinacol ester.

Example 3

Formation of 4-(4,4,5,5-Tetramethyl-1,3,2-dioxaborolan-2-yl)aniline

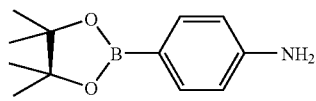

To 25.8 mg $PdCl_2(dppf).CH_2Cl_2$ in a reaction tube under nitrogen were added 4 ml dioxane, 0.43 ml (3 mmol) triethylamine, 0.46 ml (3.2 mmol) pinacolborane and 219 mg (1.0 mmol) p-iodoaniline. The reaction solution was stirred at room temp. to ensure that all the phenolic groups had reacted with pinacolborane and the hydrogen evolved was flushed out of the reaction tube with argon. The reaction solution was warmed to 80° C. with stirring in an oil bath.

After about 2 h the solution had turned green and heating was continued for a total of 8 h. An aliquot (0.3 ml) was removed from the reaction solution, extracted into ethyl acetate, washed several times with water and analysed by gc (fid detector, SGE HT5 capillary column). There was only one strong peak (area was 75% of total peak areas, uncorrected for response factors) in the gc and that was shown by gc/ms to be due to the desired arylboronic acid pinacol ester. The other peaks, both weak but of near equal area were shown by gc/ms to be due to aniline and the phenylboronic acid pinacol ester. There was no indication of the presence of unreacted p-iodoaniline in the reaction mixture.

Example 4

Formation of N-[4-(4,4,5,5-Tetramethyl-1,3,2-dioxaborolan-2-yl)phenyl]acetamide

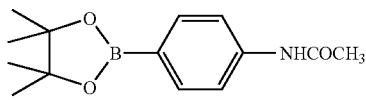

To 25 mg $PdCl_2(dppf).CH_2Cl_2$ in a reaction tube under nitrogen were added 4 ml dioxane, 0.43 ml (3 mmol) triethylamine, 0.47 ml (3.2 mmol) pinacolborane and 262 mg (1.0 mmol) p-iodoacetanilide. The p-iodoacetanilide did not react with the pinacolborane to liberate hydrogen. The reaction solution was warmed to 80° C. with stirring in an oil bath. After 1 h the solution had darkened and an aliquot (0.3 ml) was removed from the reaction solution, extracted into diethyl ether, washed several times with water and analysed by gc (fid detector, SGE HT5 capillary column). There was only one strong peak (of area 74% of total peak areas, uncorrected for response factors) in the gc and that was shown by gc/ms to be due to the desired arylboronic acid pinacol ester. On heating the reaction mixture for a further 4 h at 80° C., the apparent yield of the required boronic acid ester increased to 81% while that of the acetanilide and phenylboronic acid pinacol ester peak areas were 14% and 3.4% respectively.

The employment of a large excess of pinacolborane is not essential. The reaction has been carried out, and goes to completion (no p-iodoacetanilide remaining unreacted), using 1.1 mmol of pinacolborane.

Example 5

Formation of 4-(4,4,5,5-Tetramethyl-1,3,2-dioxaborolan-2-yl)benzamide

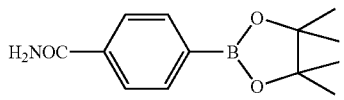

To 24.9 mg $PdCl_2(dppf).CH_2Cl_2$ in a reaction tube under nitrogen were added 4 ml dioxane, 0.43 ml (3 mmol) triethylamine, 0.6 ml (4.1 mmol) pinacolborane and 243 mg (0.98 mmol) p-iodobenzamide. After flushing the reaction tube with argon, the mixture was warmed to 80° C. with stirring for 5 h in an oil bath. An aliquot (0.3 ml) was removed from the reaction solution, extracted into ethylacetate, washed several times with water and analysed by gc (fid detector, SGE HT5 capillary column). The desired arylboronic acid pinacol ester was formed; confirmed by gc/ms. The major side product was benzamide.

Example 6

Solublising of a compound that has low solubility in common organic solvents through reaction of the functional groups that are able to form intermolecular hydrogen bonds, with a borane ester.

Formation of 4-Hydroxy-3-(4,4,5,5-tetramethyl-1,3,2-dioxaborolan-2-yl)phenylalanine

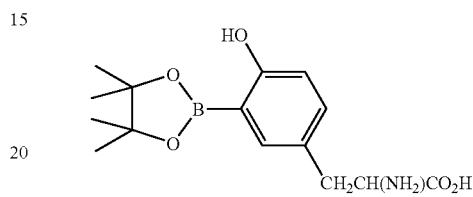

To 24.8 mg $PdCl_2(dppf).CH_2Cl_2$ in a reaction tube under nitrogen were added 4 ml dioxane, 0.43 ml (3 mmol) triethylamine, 0.51 ml (3.5 mmol) pinacolborane and 284 mg (0.92 mmol) 3-iodo-L-tyrosine. The reaction solution was stirred at room temperature to ensure that all the acidic protons had reacted with pinacolborane and the substrate dissolved. The hydrogen evolved was then flushed out of the reaction tube with argon and the mixture was warmed to 80° C. with stirring for 19 h in an oil bath. An aliquot (0.3 ml) was removed from the reaction solution, extracted into ethyl acetate, washed several times with acidified ($H_2SO_4$) water and neat water The ethyl acetate solution was analysed, after dilution in 1:1 water/acetonitrile, by hplc/ms. The formation of the desired arylboronic acid pinacol ester was confirmed by hplc/ms and on the basis of the negative ion mass spectrum, in which the I ion was not observed, (unlike in the case for the substrate 3-iodo-L-tyrosine), it is unlikely that the analysis sample contained any 3-iodo-L-tyrosine.

Example 7

Formation of 3-(4,4,5,5-Tetramethyl-1,3,2-dioxaborolan-2-yl)benzoic acid

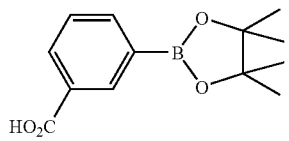

To 26.1 mg $PdCl_2(dppf).CH_2Cl_2$ in a reaction tube under nitrogen were added 4 ml dioxane, 0.43 ml (3 mmol) triethylamine, 0.37 ml (2.6 mmol) pinacolborane and 250 mg (1.0 mmol) 3-iodobenzoic acid. The reaction solution was stirred at room temperature to ensure that the carboxylic acid group had reacted with pinacolborane. The hydrogen evolved was flushed out of the reaction tube with argon. Over this period, the initial crimson coloured reaction solution turned to an orange colour. After warning to 80° C. with stirring for 73 h in an oil bath, an aliquot (0.3 ml) was removed from the reaction solution, extracted into ethyl acetate and washed with dilute sulphuric acid and then several times with water before analysing by gc (fid detector, SGE HT5 capillary column). No 3-iodobenzoic acid was found in the solution indicating that the reaction had gone to completion. Only 3 peaks were observed in the gc, other than the solvent, and these were shown by gc/ms to be due to benzoic acid and the pinacol esters of phenylboronic acid and the desired carboxylated phenylboronic acid which was present in highest concentration.

Example 8

Formation of 4-(4,4,5,5-Tetramethyl-1,3,2-dioxaborolan-2-yl)benzoic acid

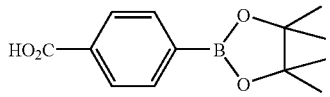

To 25.4 mg PdCl$_2$(dppf).CH$_2$Cl$_2$ in a reaction tube under nitrogen were added 4 ml dioxane, 0.43 ml (3 mmol) triethylamine, 0.37 ml (2.6 mmol) pinacolborane and 249 mg (1.0 mmol) 4-iodobenzoic acid. The reaction solution was stirred at room temp. to ensure that the carboxylic acid group had reacted with pinacolborane, the colour of the solution changing over ca. 20 min. from crimson to a pale orange-brown colour. The hydrogen evolved was flushed out of the reaction tube with argon. After warming to 80° C. with stirring for 73 h in an oil bath, an aliquot (0.3 ml) was removed from the reaction solution, extracted into ethyl acetate and washed with dilute sulphuric acid and then several times with water before analysing by gc (fid detector, SGE HT5 capillary column). No 4-iodobenzoic acid was found in the solution indicating that the reaction had gone to completion. Only 3 peaks were observed in the gc, other than the solvent, and these were shown by gc/ms to be due to benzoic acid and the pinacol esters of phenylboronic acid and the desired carboxylated phenylboronic acid which was present in highest concentration.

Example 9

Formation of 3-Methyl-4-(4,4,5,5-tetramethyl-1,3,2-dioxaborolan-2-yl)benzoic acid

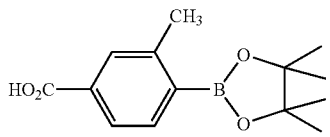

To 26 mg PdCl$_2$(dppf).CH$_2$Cl$_2$ in a reaction tube under nitrogen were added 4 ml dioxane, 0.43 ml (3 mmol) triethylamine, 0.37 ml (2.6 mmol) pinacolborane and 259 mg (0.99 mmol) 4-iodo-3-methylbenzoic acid. The reaction solution was stirred at room temp. to ensure that the carboxylic acid group had reacted with pinacolborane, the colour of the solution changing over ca. 20 min. from crimson to an orange-brown colour. The hydrogen evolved was flushed out of the reaction tube with argon. After warming to 80° C. with stirring for 73 h in an oil bath, an aliquot (0.3 ml) was removed from the reaction solution, extracted into ethyl acetate and washed with dilute sulphuric acid and then several times with water before analysing by gc (fid detector, SGE HT5 capillary column). No 4-iodo-3-methylbenzoic acid was found in the solution indicating that the reaction had gone to completion. Only 2 peaks of peak area greater than ca. 1% were observed in the gc, other than the solvent, and these were shown by gc/ms to be due to 3-methylbenzoic acid and the pinacol ester of the desired carboxylated phenylboronic acid which was present at highest concentration (peak area was 85% of total peak areas).

Example 10

This example demonstrates the effect of a promoter on the rate of reaction of a aryl bromide with pinacolborane.

Formation of 4-(4,4,5,5-Tetramethyl-1,3,2-dioxaborolan-2-yl)aniline

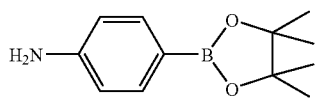

To 25 mg PdCl$_2$(dppf).CH$_2$Cl$_2$ in a reaction tube under nitrogen were added 4 ml dioxane, 0.43 ml (3 mmol) triethylamine, 0.46 ml (3.2 mmol) pinacolborane and 177 mg (1.03 mmol) p-bromoaniline. The reaction solution was stirred at room temp. for a short time and then flushed with argon and warmed to 80° C. with stirring in an oil bath. An aliquot of the pale yellow solution was removed after 5 h, extracted into ethyl acetate, washed several times with water and analysed by gc (fid detector, SGE HT5 capillary column). The amount of the desired product, identified by gc/ms, was 1.2% based on peak area (uncorrected for response factors). After 20.5 h reaction time, the amount of product had increased to 16%.

When the reaction was carried out in the presence of 28 mg of p-iodoacetanilide, product formation was appreciably faster. After 2.75 h reaction time, a sample was taken from the yellow-brown reaction solution and prepared for gc analysis as above. The amount of product in the sample, again uncorrected for response factors was, based on peak area, 26%. After 19 h reaction time the amount of this species had increased to 63% of the total peak areas and no p-bromoaniline was detected in the reaction solution. Aniline was the major side product.

Example 11

This example demonstrates the effect of a promoter on the rate of reaction of an aryl iodide with pinacolborane.

Formation of 4,4,5,5-Tetramethyl-2-(4-methylphenyl)-1,3,2-dioxaborolane

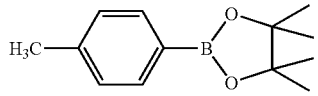

To 25.6 mg PdCl$_2$(dppf).CH$_2$Cl$_2$ in a reaction tube under nitrogen were added 4 ml dioxane, 0.43 ml (3 mmol) triethylamine, 0.22 ml (1.5 mmol) pinacolborane (crimson solution) and 219 mg (1.0 mmol) p-iodotoluene. The reaction solution was warmed to 80° C. with stirring in an oil bath. An aliquot of the pale yellow reaction solution was removed after 1 h and 2 h and a third sample after 5 h reaction time by which time the solution had turned a darkish green colour. The aliquots were extracted into ethyl acetate, washed several times with water and analysed by gc (fid detector, SGE HT5 capillary column). The amount of the tolylboronic acid pinacol ester was 5.6% after 1 h reaction time, 66% after 3 h and the reaction was finished after 5 h (based on peak area uncorrected for response factors). When the parallel reaction was carried out in the presence of 35 mg (0.13 mmol) p-iodoacetanilide, after 1 h the amount of tolylboronic acid pinacol ester formed was 34%. When the reaction solution was analysed after 3 h reaction time, the reaction had already gone to completion, indicated by the absence of p-iodotoluene in the reaction solution.

Example 12

This example demonstrates that the rate of reaction of an aryl iodide with pinacolborane can be enhanced by compounds other than an aryl iodide such as p-iodoacetanilide.

Formation of 4,4,5,5-Tetramethyl-2-phenyl-1,3,2-dioxaborolane

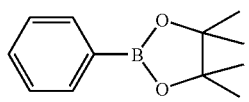

Three parallel reactions were carried out.

Reaction 1. To 26.5 mg PdCl$_2$(dppf).CH$_2$Cl$_2$ in a reaction tube under nitrogen were added 4 ml dioxane, 0.43 ml (3 mmol) triethylamine, 0.23 ml (1.5 mmol) pinacolborane (crimson solution) and 215 mg (1.05 mmol) p-iodobenzene. The reaction solution was warmed to 80° C. with stirring in an oil bath. Seven aliquots of ca. 0.3 ml were removed from the reaction solution at hourly intervals. The reaction solution remained a pale yellow colour for the first 6 aliquots and was green in colour when the seventh aliquot was taken. A final aliquot was taken after 25 h reaction time. The aliquots were extracted into ethyl acetate, washed several times with water and analysed by gc (fid detector, SGE HT5 capillary column).

Reaction 2. The reaction procedure and quantities were the same as in the Reaction 1 above except that p-iodoacetanilide (27 mg, 0.105 mmol) was added to the reaction mixture. The reaction solution remained pale yellow for the first four aliquots but was dark for the remainder.

Reaction 3. The reaction procedure and quantities employed were again the same as in Reaction 1 but to this reaction was also added acetanilide (67.7 mg, 0.50 mmol). The reaction solution remained pale yellow for the first three aliquots but was dark for the remainder.

The amount of the phenylboronic acid pinacol ester formed under the various reaction conditions is shown in the table. The concentration of phenylboronic acid pinacol ester given in the table is uncorrected for gc fid response factors or for the somewhat variable amounts of the hydroxyboronpinacolate ester (identified by gc/ms) present in the solutions analysed. For Reactions 2 and 3 the peak areas were corrected for the contribution made by the additives and their reaction products to the total peak area.

TABLE 12.1

Formation of phenylboronic acid pinacol ester from p-iodobenzene and pinacolborane with and without reaction rate enhancers. Concentration is expressed as % peak area.

| Reaction Time (hr) | No additive | 0.105 mmol p-iodoacetanilide | 0.50 mmol acetanilide |
| --- | --- | --- | --- |
| 1 | 1.6 | 10 | 6.8 |
| 2 | 6.3 | 33 | 26 |
| 3 | 17 | 74 | 64 |
| 4 | 39 | 93 | 97 |
| 5 | 75 | 96 | 95 |
| 6 | 92 | 92 | 92 |
| 7 | 90 | 92 | 92 |
| 25 | 97 | 95 | 94 |

Example 13

This example demonstrates the effect of a promoter on the rate of reaction of a bromoolefin and pinacolborane.

Formation of 2-(1,2-Dimethyl-1-propenyl)-4,4,5,5-tetramethyl-1,3,2-dioxaborolane

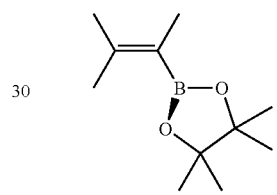

To 24.7 mg PdCl$_2$(dppf).CH$_2$Cl$_2$ in a reaction tube under nitrogen were added 4 ml dioxane, 0.43 ml (3 mmol) triethylamine, 0.23 ml (1.5 mmol) pinacolborane, 28 mg (0.1 mmol) of p-iodoacetanilide and 156 mg (1.05 mmol) 2-bromo-3-methylbut-2-ene. The reaction solution was warmed to 80° C. with stirring in an oil bath. The pale yellow solution darkened to a yellow-brown after 19 h. An aliquot of the reaction solution was removed, extracted into ethyl acetate, washed several times with water and analysed by gc (fid detector, SGE HT5 capillary column). The desired product, identified by gc/ms, had formed and was the major peak present. At longer reaction times the mixture darkened further and analysis (by gc) indicated that the reaction had gone to completion, no 2-bromo-3-methylbut-2-ene being found in the reaction solution.

Example 14

This example demonstrates the use of a Ni rather than Pd catalyst.

Formation of 5-(4,4,5,5-Tetramethyl-1,3,2-dioxaborolan-2-yl)-1,3-benzodioxole

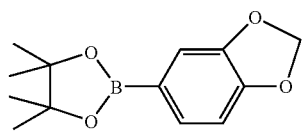

To 21.9 mg NiCl$_2$(dppf) in a reaction tube under nitrogen were added 4 ml dioxane, 0.42 ml (3 mmol) triethylamine, 0.22 ml (1.5 mmol) pinacolborane and 238 mg (0.96 mmol) 1-iodo-3,4-methylenedioxybenzene. The green coloured reaction solution was warmed to 80° C. with stirring for 6 h in an oil bath. An aliquot (ca. 0.3 ml) of the reaction solution was removed, extracted into diethyl ether and washed several times with water and analysed by gc (fid detector, SGE HT5 capillary column). Besides a little 1,3-benzodioxole, the only other product peak in the gc was that due to the desired arylboronic acid pinacol ester. NiCl$_2$ (dppf) was also shown to catalyse the formation of the desired product in acetonitrile.

Example 15

This example demonstrates the use of Pd catalysts not carrying phosphine ligands.

1. Use of Pd(10%) on Charcoal

Formation of 2-(4-Methoxyphenyl)-4,4,5,5-tetramethyl-1,3,2-dioxaborolane

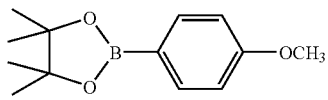

To 52 mg of Pd(10%) on charcoal and 233 mg (1.0 mmol) p-iodoanisole in a reaction tube under nitrogen were added 4 ml dioxane, 0.44 ml (3.1 mmol) triethylamine and 0.22 ml (1.5 mmol) pinacolborane. The reaction solution was warmed to 80° C. with stirring in an oil bath. An aliquot (ca. 0.3 ml) of the reaction solution was removed after 1 h and extracted into diethyl ether and washed several times with water and analysed by gc (fid detector, SGE HT5 capillary column). Besides some anisole, the only other product peak in the gc (12% of total peak area) was that due to the desired arylboronic acid pinacol ester. Analysis of a sample of the reaction solution after 2.5 h reaction time indicated that this peak had grown to 41% of the total gc peak areas.

Formation of 4,4,5,5-tetramethyl-2-(4-methylphenyl)-1,3,2-dioxaborolane

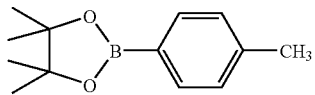

Using the same reaction conditions and quantities as in the above example with p-iodoanisole, p-iodotoluene was converted into the desired ester. After 2.5 h reaction time, the peak in the gc due to the tolylboronic acid pinacol ester was 30% of the total peak areas.

2. Use of Pd(II)acetate

Formation of 5-(4,4,5,5-Tetramethyl-1,3,2-dioxaborolan-2-yl)-1,3-benzodioxole

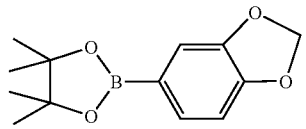

To 22 mg of Pd(II)acetate in a reaction tube under nitrogen were added 4 ml dioxane, 260 mg (1.05 mmol) 1-iodo-3,4-methylenedioxybenzene, 0.44 ml (3.1 mmol) triethylamine and 0.22 ml (1.5 mmol) pinacolborane. The solution became black on addition of the pinacolborane to the other reaction ingredients. The reaction solution was warmed to 80° C. with stirring in an oil bath. An aliquot (ca. 0.3 ml) of the reaction solution was removed after 1 h and extracted into diethyl ether and washed several times with water and analysed by gc (fid detector, SGE HT5 capillary column). Besides some 1,3-benzodioxole, the only other product peak in the gc (13% of total peak area) was that due to the desired arylboronic acid pinacol ester.

3. Use of a Palladium Catalyst with an Arsine Ligand. Reaction Using a Mixture of bis(1,2-diphenylarsino)ethane and Pd(OAc).

Formation of 5-(4,4,5,5-Tetramethyl-1,3,2-dioxaborolan-2-yl)-1,3-benzodioxole

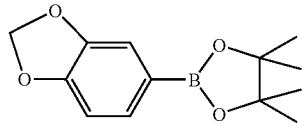

8.1 mg of Pd(OAc)$_2$ (0.036 mmol) and 16 mg (0.033 mmol) of bis(1,2-diphenylarsino)ethane were placed in a reaction tube under nitrogen together with 4 ml of dioxane and 0.45 ml of triethylamine. The tube was heated in an oil bath at 80° C. for 15.5 h and the yellow solution became brown in colour. Then added at room temperature 262 mg (1.06 mmol) of 1-iodo-3,4-methylenedioxybenzene and 0.22 ml (1.5 mmol) of pinacolborane. The reaction mixture was then warmed to 80° C. After 3 h, 45% of the total peak areas was due to the desired product. This increased to 73% after 24 h.

Example 16

One pot reaction to form an unsymmetrical biaryl.

Formation of 4-(1,3-Benzodioxol-5-yl)benzamide

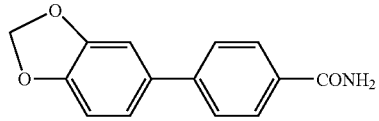

To 28 mg PdCl$_2$(dppf).CH$_2$Cl$_2$ in a reaction tube under nitrogen were added 4 ml dioxane, 0.43 ml (3 mmol) triethylamine, 0.23 ml (1.5 mmol) pinacolborane and 262 mg (1.06 mmol) 1-iodo-3,4-methylenedioxybenzene. The reaction solution was warmed to 80° C. with stirring in an oil bath for 22 h. An aliquot (0.3 ml) was removed from the reaction and extracted into ethyl acetate and washed several times with water and analysed by gc (fid detector, SGE HT5 capillary column). All the 1-iodo-3,4-methylenedioxybenzene had reacted to form the boronic acid ester together with some 1,3-benzodioxole. After addition of 8 ml methanol (which destroys the excess pinacolborane and thereby prevents the formation of symmetrical biaryl), 1.07 g Cs2CO3 and 261 mg (1.06 mmol) 4-iodobenzamide, the solution was warmed to 40° C. for 17 h. An aliquot (0.5 ml) was removed from the reaction solution and extracted into ethyl acetate and washed several times with water, and analysed by gc (fid detector, SGE HT5 capillary column). The required biaryl (identified by gc/ms) gave rise to the strongest peak in the gc trace.

Example 17

This example demonstrates that palladium catalysts can be activated by treatment with a base prior to their use in promoting the reaction of an organic halide with a dialkoxyborane. In particular, the catalytic activity of $PdCl_2(dppf)$ $.CH_2Cl_2$ can be increased significantly, especially the initial activity, by treatment, in the reaction solvent, with triethylamine prior to the addition of the pinacolborane and substrate. Besides the rate enhancement observed in the formation of the required product boronic acid ester (e.g. pinacol ester of 3,4-methylenedioxyphenylboronic acid) there is a further advantage in the prior activation of the catalyst in that the amount of bi-product formed in the reaction (viz. 1,3-benzodioxole through dehalogenation of the substrate and the pinacol ester of phenylboronic acid in which the phenyl groups are from the catalyst ligand) is significantly reduced.

Formation of 5-(4,4,5,5-Tetramethyl-1,3,2-dioxaborolan-2-yl)-1,3-benzodioxole

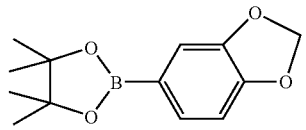

To 24.6 mg $PdCl_2(dppf).CH_2Cl_2$ in a reaction tube under nitrogen was added 4 ml dioxane and 0.42 ml (3 mmol) triethylamine. The mixture was heated at 80° C. for ca. 17 h. The red-orange suspension of $PdCl_2(dppf).CH_2Cl_2$ dissolved to give a dark red-brown solution. To this solution, at room temperature, was added 0.23 ml (1.5 mmol) pinacolborane and 253 mg (1.02 mmol) 1-iodo-3,4-methylenedioxybenzene. The reaction solution was warmed to 80° C. with stirring for 1 h in an oil bath. The solution remained a dark red-brown in colour. An aliquot (ca. 0.25 ml) of the reaction solution was removed, extracted into ethyl acetate and washed several times with water and brine solution and analysed by gc (fid detector, SGE HT5 capillary column). Apart from a small amount of 1,3-benzodioxole (5% of uncorrected gc peak area) and pinacol ester of phenylboronic acid (3%), the only other product peak in the gc (area of 92%, uncorrected) was that due to the desired arylboronic acid pinacol ester. There was no evidence of biaryl formation. The rate of reaction of 1-iodo-3,4-methylenedioxybenzene with pinacolborane at 80° C. with activated catalyst is indicated also in Table 17.1. Table 17.2 shows that side product formation can be reduced still further by carrying out the reaction at 30° C.

TABLE 17.1

Rate of product formation on reaction* of 1-iodo-3,4-methylenedioxybenzene with pinacolborane at 80° C. in which the catalyst, $PdCl_2(dppf).CH_2Cl_2$, was activated, prior to employment in the reaction, with triethylamine. The concentrations are expressed in area % (uncorrected for response factors) determined by gc analysis of aliquots of the reaction solution taken at selected reaction times.

| Reaction Time (mins) | benzodioxole | phenyl pinacol boronate | iodo-methylenedioxybenzene | methylenedioxyphenyl pinacol boronate |
|---|---|---|---|---|
| 6 | 4.4 | 0.74 | 54 | 40 |
| 10 | 4.4 | 1.0 | 40 | 55 |
| 15 | 5.2 | 2.1 | 26 | 66 |
| 20 | 5.9 | 2.9 | 16.3 | 75 |
| 25 | 5.7 | 2.9 | 9.2 | 82 |
| 30 | 6.0 | 3.2 | 3.6 | 87 |
| 35 | 5.9 | 3.4 | 1.2 | 89 |
| 40 | 5.7 | 3.4 | 0.7 | 90 |
| 50 | 5.6 | 3.4 | 0 | 91 |
| 180 | 5.7 | 3.5 | 0 | 91 |

*Used 25.5 mg of $PdCl_2(dppf).CH_2Cl_2$, 4 ml dioxane, 0.43 ml(3.0 mmol) triethylamine and warmed to 80° C. for 16 h. Then added 0.23 ml (1.5 mmol) pinacolborane and 247 mg (1.0 mmol) 1-iodo-3,4-methylenedioxybenzene at room temp. before warming the reaction to 80° C. The reaction was quenched at the selected reaction time by addition of the aliquot of reaction solution to a water/ethyl acetate mixture.

TABLE 17.2

Rate of product formation on reaction* of 1-iodo-3,4-methylenedioxybenzene with pinacolborane at 30° C. in which the catalyst, PdCl$_2$(dppf).CH$_2$Cl$_2$, was activated, prior to employment in the reaction, with triethylamine. The concentrations are expressed in area % (uncorrected for response factors) determined by gc analysis of aliquots of the reaction solution taken at selected reaction times

| Reaction time (h) | 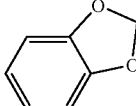 | 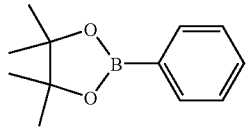 | 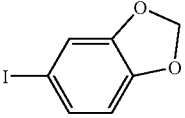 | 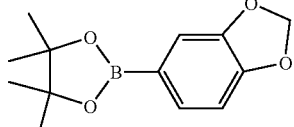 |
|---|---|---|---|---|
| 1 | 1.6 | 0 | 94 | 4.8 |
| 2 | 1.7 | 0 | 89 | 9.7 |
| 3 | 2 | 0 | 84 | 13.8 |
| 4 | 2 | 0 | 81 | 17 |
| 7 | 2.3 | 0 | 71 | 26 |
| 28 | 4 | 0.6 | 27 | 68 |
| 71.5 | 4.2 | 1.9 | 0 | 94 |

*Used 25 mg of PdCl$_2$(dppf).CH$_2$Cl$_2$, 4 ml dioxane, 0.43 ml (3.0 mmol) triethylamine and warmed to 80° C. for 16 h. Then added 0.23 ml (1.5 mmol) pinacolborane and 262 mg (1.05 mmol) 1-iodo-3,4-methylenedioxybenzene at room temp. before warming the reaction to 80° C. The reaction was quenched at the selected reaction time by addition of the aliquot of reaction solution to a water/ethyl acetate mixture.

When the catalyst PdCl$_2$(dppf).CH$_2$Cl$_2$ is treated with the amine together with the borane ester prior to use in the reaction, the initial reaction rate is enhanced, indicating that some catalyst has been activated. The overall reaction, however, is slower than that when the catalyst receives no pretreatment. Catalyst presumably unactivated by the pretreatment with triethylamine and pinacolborane appears to be more resistant to activation during the progress of the boronation reaction. This can be seen by comparison of Tables 17.3 and 17.4. In Table 17.3. the catalyst was not activated prior to use and the reaction rate over the first 1 to 2 hours is slow. In Table 17.4, the catalyst was treated with both triethylamine and pinacolborane prior to use in the reaction and the initial reaction rate is enhanced but the overall reaction is slower than that shown in Table 17.3. The prior treatment of the catalyst with triethylamine and pinacolborane does, however, improve the yield of product by reducing dehalogenation.

TABLE 17.3

Rate of product formation on reaction* of 1-iodo-3,4-methylenedioxybenzene with pinacolborane at 80° C. in which the catalyst, PdCl$_2$(dppf).CH$_2$Cl$_2$, was not activated, prior to employment in the reaction, with triethylamine. The concentrations are expressed in area % (uncorrected for response factors) determined by gc analysis of aliquots of the reaction solution taken at selected reaction times.

| Reaction Time (h) | 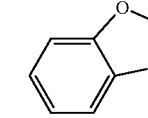 | 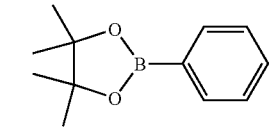 | 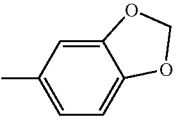 | 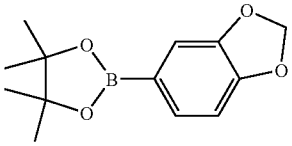 |
|---|---|---|---|---|
| 1 | 1.1 | 0.75 | 94 | 4.5 |
| 2 | 2.2 | 3.7 | 73 | 20 |
| 3 | 9.1 | 6.7 | 13 | 70 |
| 4 | 11.4 | 6.5 | 0 | 80 |
| 5 | 12.4 | 6.7 | 0 | 78 |
| 6 | 12 | 6.5 | 0 | 79 |

*Used 27 mg of PdCl$_2$(dppf).CH$_2$Cl$_2$, 4 ml dioxane, 0.43 ml (3.0 mmol) triethylamine, 0.23 ml (1.5 mmol) pinacolborane and 262 mg (1.05 mmol) 1-iodo-3,4-methylenedioxybenzene. The reaction was quenched at the selected reaction time by addition of the aliquot of reaction solution to a water/ethyl acetate mixture.

TABLE 17.4

Rate of product formation on reaction* of 1-iodo-3,4-methylenedioxybenzene with pinacolborane at 80° C. in which the catalyst, PdCl₂(dppf).CH₂Cl₂, was treated, prior to employment in the reaction, with triethylamine and pinacolborane. The concentrations are expressed in area % (uncorrected for response factors) determined by gc analysis of aliquots of the reaction solution taken at selected reaction times.

| Reaction Time (h) | 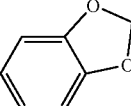 | 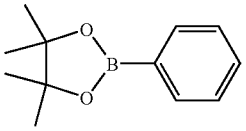 | 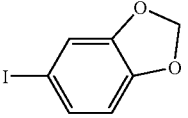 | 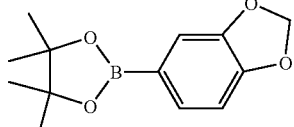 |
|---|---|---|---|---|
| 1 | 0.8 | 3.5 | 74 | 21 |
| 2 | 1.4 | 4.5 | 45 | 48 |
| 3 | 1.9 | 5.5 | 22 | 70 |
| 4 | 2.4 | 6.0 | 7.5 | 84 |
| 5 | 2.8 | 6.3 | 0 | 91 |
| 6 | 2.8 | 6.3 | 0 | 91 |

*Used 27 mg of PdCl₂(dppf).CH₂Cl₂, 4 ml dioxane, 0.43 ml (3.0 mmol) triethylamine, 0.23 ml (1.1 mmol) pinacolborane heated for ca. 17 at 80° C. Then added 262 mg (1.05 mmol) 1-iodo-3,4-methylenedioxybenzene at room temp. before warming reaction to 80° C. The reaction was quenched at the selected reaction time by addition of the aliquot of reaction solution to a water/ethyl acetate mixture.

The amount of triethylamine used to activate the catalyst may be less than that used in the above reactions. Treatment of 25.8 mg PdCl₂(dppf).CH₂Cl₂ in a reaction tube, under nitrogen, with 4 ml dioxane and 0.14 ml (1 mmol) triethylamine at 80° C. for 40 h gave a red-brown solution that still contained undissolved material, presumably PdCl₂(dppf).CH₂Cl₂. After cooling to room temp., 0.23 ml (1.5 mmol) pinacolborane and 267 mg (1.08 mmol) 1-iodo-3,4-methylenedioxybenzene were added and the reaction solution warmed to 80° C., with sting, in an oil bath. An aliquot (ca. 0.25 ml) of the reaction solution was removed at intervals, added to ethyl acetate/water which quenched the reaction and after washing the ethyl acetate solution several times with water, the solution was analysed by gc. The results, given in Table 17.5, indicate that the catalyst was activated but not as effectively as when more triethylamine was employed. The amount of dehalogenation of the substrate is considerably increased on using the smaller amount (near stoichiometric) of base and this is the more pronounced as the base becomes depleted through formation of Et₃N.HI nearer the end of the reaction.

TABLE 17.5

Rate of product formation on reaction of 1-iodo-3,4-methylenedioxybenzene with pinacolborane at 80° C. in which the catalyst, PdCl₂(dppf).CH₂Cl₂, was activated, prior to employment in the reaction, with triethylamine (1 mmol). The concentrations are expressed in area % (uncorrected for response factors) determined by gc analysis of aliquots of the reaction solution taken at selected reaction times*.

| Reaction Time (mins) | 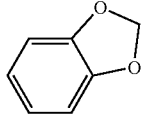 | 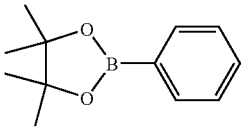 | 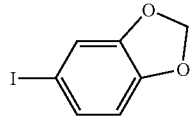 | 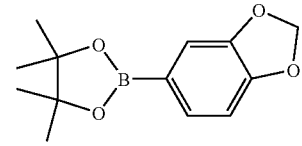 |
|---|---|---|---|---|
| 5.5 | 1.6 | 0 | 93 | 4.3 |
| 10 | 2.6 | 0 | 84 | 11 |
| 15 | 3.7 | 0 | 73 | 19 |
| 20 | 3.3 | 0 | 64 | 29 |
| 25 | 4.5 | 0 | 53 | 38 |
| 30 | 5.5 | 1.8 | 46 | 44 |
| 40 | 7.2 | 2.2 | 33 | 54 |
| 50 | 11 | 2.3 | 17 | 62 |
| 60 | 16 | 2.3 | 6.2 | 67 |
| 80 | 18 | 2.5 | 0 | 75 |
| 240 | 19 | 2.3 | 0 | 70 |

Example 18

This example demonstrates that there is an inverse relationship between the amount of base (triethylamine) used in the reaction and the extent of dehalogenation of 1-iodo-3,4-methylenedioxybenzene. It also demonstrates that the amount of pinacolborane required for the complete reaction of the aryl halide can be less than 1.5 equivalents. Unreacted pinacolborane was found at the completion of the reaction when 1.1 equivalents were used.

Formation of 5-(4,4,5,5-Tetramethyl-1,3,2-dioxaborolan-2-yl)-1,3-benzodioxole

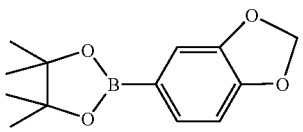

To 25.1 mg PdCl$_2$(dppf).CH$_2$Cl$_2$ in a reaction tube under nitrogen were added 4 ml dioxane, 0.42 ml (3 mmol) triethylamine, 0.16 ml (1.1 mmol) pinacolborane and 256 mg (1.03 mmol) 1-iodo-3,4-methylenedioxybenzene. The reaction solution was warmed to 80° C., with stirring, for 16 h in an oil bath. An aliquot (ca. 0.25 ml) of the reaction solution was removed, extracted into ethyl acetate and washed several times with water and brine solution and analysed by gc (fid detector, SGE HT5 capillary column). Hydrogen evolution was observed on the initial contact of the reaction sample with water, indicative that excess pinacolborane was present at the completion of the reaction even though only 1.1 equivalents had been used. Besides the 1,3-benzodioxole (10% of gc peak area) and pinacol ester of phenylboronic acid (7%), the only other product peak in the gc (area of 81%) was that due to the desired arylboronic acid pinacol ester. In a parallel reaction in which the only change was a reduction in the amount of triethylamine used, from 3.0 equivalents to 1.0 equivalents, the product distribution found was 1,3-benzodioxole (23% of gc peak area), the pinacol ester of phenylboronic acid (6%) and the desired arylboronic acid pinacol ester (peak area 69%).

Example 19

Bases Other than Triethylamine

Formation of 5-(4,4,5,5-Tetramethyl-1,3,2-dioxaborolan-2-yl)-1,3-benzodioxole

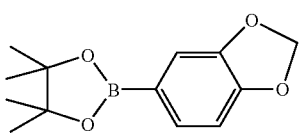

(i) Quinuclidine

To 25.7 mg PdCl$_2$(dppf).CH$_2$Cl$_2$ and 111 mg (1.0 mmol) of quinuclidine in a reaction tube under nitrogen were added 4 ml dioxane, 0.23 ml (1.5 mmol) pinacolborane and 247 mg (1.0 mmol) 1-iodo-3,4-methylenedioxybenzene. The brownish reaction solution was warmed to 80° C. with stirring for 16 h in an oil bath. Analysis of the reaction solution by gc as described above indicated that the main reaction was dehalogenation to 1,3-benzodioxole (69% of gc peak area). The formation of the pinacol ester of phenylboronic acid was small (0.7%) and the desired arylboronic acid pinacol ester peak area was 25%. Increasing the quinuclidine concentration to 3 mmol was highly detrimental to product formation. Found: 1,3-benzodioxole (98% of gc peak area); pinacol ester of 3,4-methylenedioxyphenylboronic acid (less than 2% of peak area).

(ii) N-Methylpiperidine

To 26.1 mg PdCl$_2$(dppf).CH$_2$Cl$_2$ in a reaction tube under nitrogen were added 4 ml dioxane, 0.12 ml (1.0 mmol) of N-methypiperidine, 0.16 ml (1.1 mmol) pinacolborane and 253 mg (1.02 mmol) 1-iodo-3,4-methylenedioxybenzene. The red reaction solution was warmed to 80° C. with stirring for 17 h in an oil bath. Analysis of the dark green reaction solution by gc as described above gave the reaction product distribution: 1,3-benzodioxole (16% of gc peak area); the pinacol ester of phenylboronic acid (7%) and the desired arylboronic acid pinacol ester (peak area 76%). Increasing the N-methypiperidine concentration to 3 mmol had little effect on product distribution. Found: 1,3-benzodioxole (17% of gc peak area); the pinacol ester of phenylboronic acid (8%) and the pinacol ester of 3,4-methylenedioxyphenylboronic acid (peak area 75%).

(iii) 2,6-Dimethylpiperidine (a sterically hindered secondary amine)

To 27.7 mg PdCl$_2$(dppf).CH$_2$Cl$_2$ in a reaction tube under nitrogen were added 4 ml dioxane, 0.14 ml (1.0 mmol) of 2,6-dimethylpiperidine, 0.23 ml (1.5 mmol) pinacolborane (crimson solution) and 261 mg (1.05 mmol) 1-iodo-3,4-methylenedioxybenzene. The crimson reaction solution was warmed to 80° C. with stirring in an oil bath. Analysis of the reaction solution by gc, as described above, was carried out at intervals (see Table 19.1). The reaction is fast and is complete after 4 h reaction time. The initial reaction rate with 1 mmol of 2,6-dimethylpiperidine as base exceeds that found using 3 mmol of triethylamine (see Table 17.3; catalyst not activated prior to reaction) and the final product distribution is essentially the same. This is not the case if one compares the reactions in which either 1 mmol of 2,6-dimethylpiperidine or 1 mmol of triethylamine is used as base. As noted above, dehalogenation in reactions using 1 mmol of triethylamine is considerable (23% of peak area in the gc is due to 1,3-benzodioxole) and the desired product, the pinacol ester of 3,4-methylenedioxyphenylboronic acid is only 69% of peak area.

The results are different when 3 mmol of 2,6-dimethylpiperidine is used in the reaction. The reaction rate is reduced, especially after the first 1 to 2 hours (see Table 19.2). The results suggest that in situ catalyst activation may be initially enhanced using 2,6-dimethylpiperidine but excess of this base also retards the reaction. Dehalogenation occurs predominantly during the earlier part of the reaction.

TABLE 19.1

Rate of product formation on reaction of 1-iodo-3,4-methylenedioxybenzene with pinacolborane at 80° C., catalyst PdCl₂(dppf).CH₂Cl₂, base 2,6-dimethylpiperidine (1.0 mmol). The concentrations are expressed in area % (uncorrected for response factors) determined by gc analysis of aliquots of the reaction solution taken at selected reaction times*.

| Reaction Time (h) | 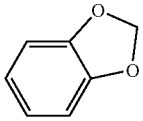 | 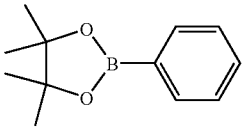 | 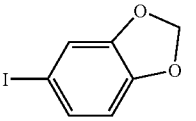 | 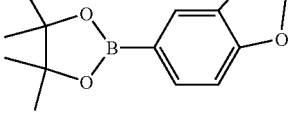 |
|---|---|---|---|---|
| 1 | 8.7 | 2 | 70 | 20 |
| 2 | 8.4 | 4.3 | 42 | 44 |
| 3 | 8.5 | 6.2 | 16 | 67 |
| 4 | 11.5 | 6.5 | 0.3 | 80 |
| 5 | 11.6 | 6.4 | 0 | 80 |

*The reaction was quenched at the selected reaction time by addition of the aliquot of reaction solution to a water/ethyl acetate mixture.

TABLE 19.2

Rate of product formation on reaction of 1-iodo-3,4-methylenedioxybenzene with pinacolborane at 80° C., catalyst PdCl₂(dppf).CH₂Cl₂, base 2,6-dimethylpiperidine (3.0 mmol). The concentrations are expressed in area % (uncorrected for response factors) determined by gc analysis of aliquots of the reaction solution taken at selected reaction times*.

| Reaction Time (h) | 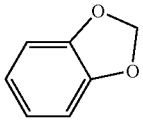 | 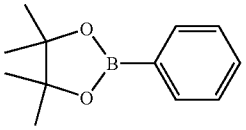 | 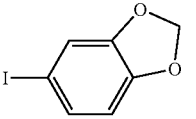 | 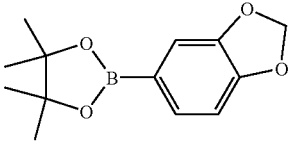 |
|---|---|---|---|---|
| 1 | 8.9 | 1.3 | 69 | 20 |
| 2 | 9.2 | 2.8 | 49 | 38 |
| 3 | 9.6 | 3.5 | 33 | 53 |
| 4 | 11 | 5.1 | 25 | 58 |
| 5 | 10 | 5.6 | 18 | 66 |
| 6 | 10 | 5.9 | 13 | 71 |
| 25.5 | 12 | 6.1 | 2.2 | 78 |

*The reaction was quenched at the selected reaction time by addition of the aliquot of reaction solution to a water/ethyl acetate mixture.

Example 20

Other Palladium Catalysts

Formation of 5-(4,4,5,5-Tetramethyl-1,3,2-dioxaborolan-2-yl)-1,3-benzodioxole

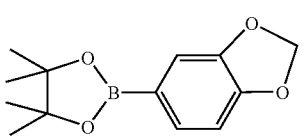

(i) PdCl₂[(PPh₂(CH₂)₅PPh₂]

To 24.7 mg PdCl₂[(PPh₂(CH₂)₅PPh₂] in a reaction tube under nitrogen was added 4 ml dioxane and 0.43 ml (3.0 mmol) of triethylamine. The mixture was heated at 80° C. to give an orange coloured solution which still contained solids, presumably PdCl₂[(PPh₂(CH₂)₅PPh₂]. To this mixture, at room temperature, were added 0.23 ml (1.5 mmol) pinacolborane (solution became brown but still contained insolubles) and 255 mg (1.03 mmol) 1-iodo-3,4-methylenedioxybenzene. The reaction solution was warmed to 80° C. with stirring in an oil bath. Analysis of the reaction solution by gc, as described above, was carried out at intervals (see Table 20.1). The reaction was complete after 5 h reaction time. The reaction solution was a bright crimson colour at the completion of the reaction and the only solids present on cooling to room temp. appeared to be the triethylamine salt. The amount of pinacol ester of phenylboronic acid formed is low with PdCl₂[(PPh₂(CH₂)₅PPh₂] as catalyst and forms only later in the reaction.

TABLE 20.1

Rate of product formation on reaction of 1-iodo-3,4-methylenedioxybenzene with pinacolborane at 80° C. The catalyst PdCl$_2$[(PPh$_2$(CH$_2$)$_5$PPh$_2$] was heated with the base triethylamine (3.0 mmol) prior to reaction. The concentrations are expressed in area % (uncorrected for response factors) determined by gc analysis of aliquots of the reaction solution taken at selected reaction times*.

| Reaction Time (mins) | 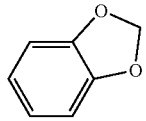 | 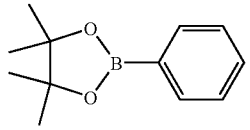 | 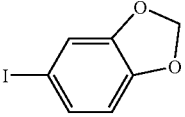 | 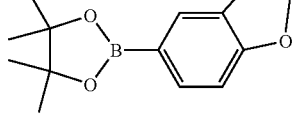 |
|---|---|---|---|---|
| 5 | 0 | 0 | 99 | 1 |
| 15 | 0 | 0 | 90 | 10 |
| 30 | 4.0 | 0 | 60 | 36 |
| 60 | 5.2 | 0 | 40 | 54 |
| 150 | 7.1 | 1.8 | 13 | 78 |
| 210 | 7.9 | 2.1 | 3.5 | 86 |
| 300 | 9.3 | 2.4 | 0 | 88 |

*The reaction was quenched at the selected reaction time by addition of the aliquot of reaction solution to a water/ethyl acetate mixture.

(ii) PdCl$_2$[(PCy$_3$)$_2$]

To 24.4 mg PdCl$_2$[(PCy$_3$)$_2$] in a reaction tube under nitrogen was added 4 ml dioxane and 0.43 ml (3.0 mmol) of triethylamine. The mixture was heated at 80° C. to give an lime-green coloured solution which still contained solids, presumably PdCl$_2$[(PCy$_3$)$_2$]. To this mixture, at room temperature, were added 0.23 ml (1.5 mmol) pinacolborane and 247 mg (1.0 mmol) 1-iodo-3,4-methylenedioxybenzene. The reaction solution was warmed to 80° C. with stirring in an oil bath. Analysis of the reaction solution by gc, as described above, was carried out at intervals (see Table 20.2). After the initial hour reaction period, the reaction rate increased sharply and the reaction was essentially complete after 3.5 hours. Solubilisation and activation of the catalyst appears to occur over the first hour of heating the reaction mixture. The reaction solution remains virtually colourless over the course of the reaction and the catalyst is all dissolved at the end of the reaction. Importantly, the absence of phenyl groups on the catalyst gives a product which is not contaminated by the pinacol ester of that particular phenylboronic acid. This eliminates the major difficulty in the purification of the product arylboronic acid ester or, in the case of "one-pot" coupling reactions, it eliminates the need to separate a biaryl mixture.

TABLE 20.2

Rate of product formation on reaction of 1-iodo-3,4-methylenedioxybenzene with pinacolborane at 80° C. The catalyst PdCl$_2$[(PCy$_3$)$_2$] was heated with the base triethylamine (3.0 mmol) prior to reaction. The concentrations are expressed in area % (uncorrected for response factors) determined by gc analysis of aliquots of the reaction solution taken at selected reaction times*.

| Reaction Time (mins) | 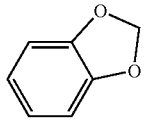 | 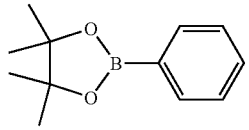 | 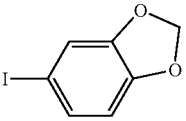 | 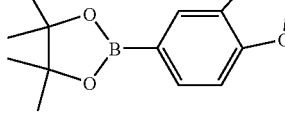 |
|---|---|---|---|---|
| 6 | 0 | 0 | 98 | 1 |
| 16 | 0 | 0 | 98 | 2 |
| 31 | 0 | 0 | 97 | 3 |
| 60 | 0 | 0 | 92 | 8.3 |
| 150 (2.5 h) | 3.9 | 0 | 29 | 67 |
| 210 (3.5 h) | 9.6 | 0 | 1.7 | 89 |
| 300 (5 h) | 11 | 0 | 0 | 89 |

*The reaction was quenched at the selected reaction time by addition of the aliquot of reaction solution to a water/ethyl acetate mixture.

(iii) PdCl$_2$[(PPh$_2$(CH$_2$)$_4$PPh$_2$)]

6.8 mg of Pd(OAc)$_2$ (0.03 mmol) and 13 mg (0.03 mmol) of bis(1,2-diphenylphosphino)ethane were placed in a reaction tube under nitrogen together with 4 ml of dioxane and 0.45 ml of triethylamine. The tube was heated in an oil bath at 80° C. for 15.5 h and the solution became reddish in colour. Then added at room temperature 267 mg (1.08 mmol) of 1-iodo-3,4-methylenedioxybenzene and 0.23 ml (1.5 mmol) of pinacolborane. The reaction mixture was then warmed to 80° C. After 3 h, the reaction was complete with 92% of the total peak areas due to the desired product.

Example 21

Larger scale (0.35M) synthesis of N-[4-(4,4,5,5-Tetramethyl-1,3,2-dioxaborolan-2-yl)phenyl]acetamide

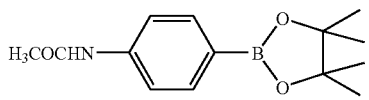

from p-iodoacetanilide in the presence of dimethyl sulfide using pinacolborane prepared from the methyl sulfide adduct of $BH_3$.

The catalyst amount in this reaction was reduced to approx. 1/35 that used in the small scale reactions. The molar ratio of catalyst:iodide:pinacolborane:$NEt_3$ is 1:1150:1500:2933. The amount of pinacolborane was 1.25 equivalents compared to the iodide. The pinacolborane was made from $BH_3.SMe_2$ by reaction with pinacol in dioxane. 50 ml of $BH_3.SMe_2$ were dissolved in 100 ml of dioxane in a 1 L Schlenk flask. To this was added dropwise 63.0 g of pinacol in 140 ml dioxane. After the addition was complete the solution was stirred at room temp. and then at 60° C. to ensure complete reaction of the $BH_3.SMe_2$. The solution contained a little white precipitate.

The catalyst was activated prior to use by heating 1500 mg of $PdCl_2[dppf].CH_2Cl_2$ with 30 ml of triethylamine in 370 ml dioxane at 80° C. from for 7.5 h. 67 ml of this dark brown solution was used in the reaction.

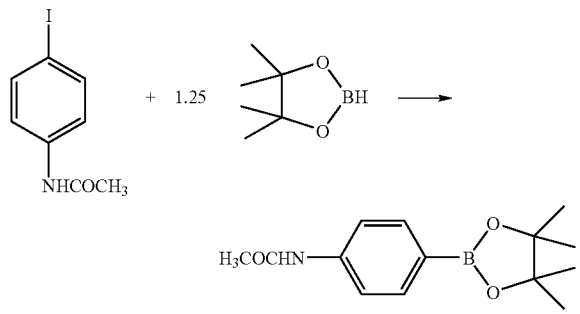

To the pinacolborane solution was added 120 ml (863 mmol) dry triethylamine, 92 g (352.5 mmol) p-iodoacetanilide and then 67 ml of the catalyst solution. The reaction solution was placed in the oil bath at 80° C. The solution became clear and pale brown in colour and after about 1 to 2 h, a precipitate of the amine.HI salt separated. After 5 h the reaction was over 90% complete. Heating was continued for several more hours after which no starting material was observed, by gc, to be in the reaction solution. The reaction product in a number of such reactions was always over 90% by gc, the only side product observed was acetanilide. No phenylboronic acid pinacol ester were seen in the gc unless very strong solutions were employed.

The crude product was isolated by removing the amine salt from the solution at room temp. The excess pinacolborane was destroyed with dry methanol. After reducing the volume of the reaction solution, the product was precipitated with petroleum ether. The dark coloured impurity in the product was removed by passing a solution of the product in toluene through a short column of Merck type 9385.1000 silica gel 60. The product was obtained as a white solid, mp>162° C. from toluene.

The presence of borane methyl sulfide complex in these reactions does not stop the reaction from progressing. It can retard rate of the reaction somewhat but indications are that it can retard, especially with certain substrate, the dehalogenation reaction to a greater extent than the boronation reaction and so lead to an increase in product yield.

Example 22

Use of Diethoxyborane in the Boronation of Aryls.

This reaction demonstrates that it is not necessary to use glycol esters of borane to carry out the boronation of aryls and that the diesters of borane with monohydric alcohols are reagents for this reaction.

Synthesis of Diethyl 1,3-benzodioxol-5-ylboronate

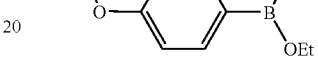

To 25.2 mg of $PdCl_2(dppf).CH_2Cl_2$ in a reaction tube under nitrogen was added 4 ml dioxane and 0.45 ml (3 mmol) triethylamine. The solution was heated at 80° C. for 18.5 h to activate the catalyst.

A solution of $HB(OEt)_2$ was made by adding 0.19 ml ethanol in 2 ml dioxane to a solution of 0.15 ml of a 10 M solution of $BH_3.SMe_2$ in 2 ml dioxane with cooling to a little above the freezing point of dioxane and then stirring overnight at room temp.

After adding 281 mg (1.13 mmol) 1-iodo-3,4-methylenedioxybenzene to the catalyst solution followed by the $HB(OEt)_2$ solution the reaction mixture was warmed to 80° C. in an oil bath.

The progress of the reaction was followed by removal of a series of samples of the reaction solution, and treating these with an ethyl acetate solution of pinacol and extracting with 10% brine solution. This work-up procedure converted the arylboron product species to its pinacol ester, a convenient molecule for gc identification. The reaction proceeds quite rapidly, the area of the gc peak of 1-iodo-3,4-methylenedioxybenzene being reduced rapidly, being about half of the total peak areas after 1 h reaction time. When tested after 23.5 h reaction time all the 1-iodo-3,4-methylenedioxybenzene had been consumed and the major peak in the gc was that of the pinacol ester of the product.

Example 23

Use of 1,3,2-dioxaborolane species, other than 4,4,5,5-tetramethyl-1,3,2-dioxaborolane, to prepare organylboronic acid esters.

1-Iodo-3,4-methylenedioxybenzene was used as substrate to demonstrate these reactions. The catalyst was activated (see below) $PdCl_2[dppf]$ and the 1,3,2-dioxaborolane species were prepared from the appropriate diol and $BH_3.SMe_2$. The organylboronic acid esters reaction products, which were obtained in good to excellent yield, were identified by gc/ms. A typical reaction is that described for the formation of the species in which the diol used was phenyl-1,2-ethanediol.

(i) Synthesis of 5-(4-phenyl-1,3,2-dioxaborolan-2-yl)-1,3-benzodioxole

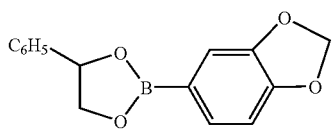

The 4-phenyl-1,3,2-dioxaborolane was first prepared by reaction of 236 mg phenyl-1,2-ethanediol (1.7 mmol) with borane dimethylsulfide adduct (0.15 ml, 1.5 mmol) in 2 ml of dioxane. A stock solution of the catalyst in dioxane was made by heating 250 mg $PdCl_2[dppf].CH_2Cl_2$ with triethylamine (4.5 ml) at 80° C. for 20 h in 40 ml dioxane. To this solution was added 2.48 g (10 mmol) of 1-iodo-3,4-methylenedioxybenzene. 4.8 ml of this reaction solution was then placed in the reaction tube containing the borane ester. The mixture was heated for 20 h at 80° C. and then an aliquot was removed, dissolved in some ethyl acetate containing a little of the diol and shaken with 10% brine solution. After drying with $MgSO_4$, the gc was measured. One major peak, of retention time 15.7 mins was found. This was shown by gc/ms to be the desired product.

Other organylboronic acid esters prepared by the same route were:

(ii) 5-(4,5-dimethyl-1,3,2-dioxaborolan-2-yl)-1,3-benzodioxole

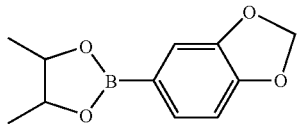

GC retention times 9.28 and 9.97 mins.

(iii) 5-(4,5-diphenyl-1,3,2-dioxaborolan-2-yl)-1,3-benzodioxole

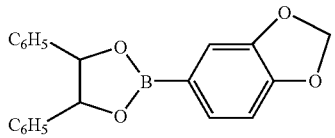

GC retention time 19.1 mins.

(iv) 5-[4-(methoxymethyl)-1,3,2-dioxaborolan-2-yl]-1,3-benzodioxole

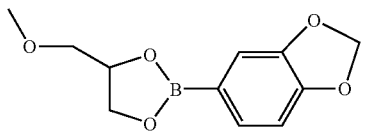

This material lost the diol readily during the water washing of the gc sample. The aliquot of the reaction solution used for the gc analysis was therefore treated with a solution of pinacol in ethyl acetate and then washed with water. The product was identified by gc/ms as the pinacol ester of the boronic acid. GC retention time 10.6 mins.

(v) 5-tetrahydro-3aH-cyclopenta[d][1,3,2]dioxaborol-2-yl-1,3-benzodioxole

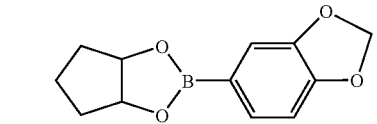

GC retention time 12.1 mins.

Example 24

The use of 1,3,2-dioxaborinane species to prepare organylboronic acid esters.

In the reactions below 1-iodo-3,4-methylenedioxybenzene was used as substrate. The reaction conditions including the activation of the catalyst and the synthesis of the borinane were the same as described in Example 23. The reaction products were identified by gc/ms.

(i) 5-(5,5-dimethyl-1,3,2-dioxaborinan-2-yl)-1,3-benzodioxole

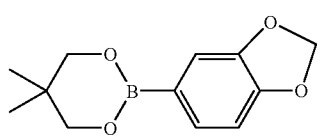

One major peak, of retention time 11.5 mins, shown to be the desired product, was found.

(ii) 5-(4,4,6-trimethyl-1,3,2-dioxaborinan-2-yl)-1,3-benzodioxole

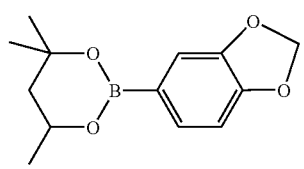

GC retention time 11.3 mins.

(iii) 5-(4,4,6,6-tetramethyl-1,3,2-dioxaborinan-2-yl)-1,3-benzodioxole

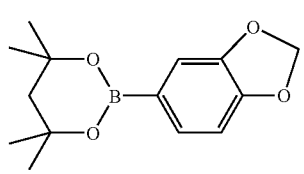

GC retention time 11.6 nuns.

Example 25

Synthesis of organylboronic acid monoesters in which the boron is also attached to a nitrogen atom.

Synthesis of 2-(1,3-benzodioxol-5-yl)-3-methyl-1,3,2-oxazaborolidine

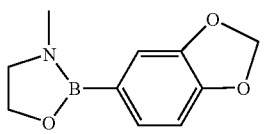

The reaction was carried out following the reactions described in Example 23 but using the aminoalcohol, 2-methylaminoethanol, instead of a diol. For the gc analysis pinacol was added to the ethyl acetate solution. One major peak of retention time 10.4 mins was found in the gc and this was identified by gc/ms as the pinacol ester of the arylboronic acid. The required compound therefore is formed in good yield but is not stable towards hydrolysis during the aqueous extraction and forms the boronic acid. In the absence of added pinacol no peaks are observed in the gc analysis.

Example 26

The formation of arylboronic acid esters with the chiral diol (1S,2S,3R,5S)-(+) pinanediol.

A stock solution of the borane (1S,2S,6R,8S)-2,9,9-trimethyl-3,5-dioxa-4-boratricyclo[6.1.1.0$^{2,6}$]decane was synthesised from the diol (1.96 g; 11.5 mmol) and 1.1 ml of BH$_3$.SMe$_2$ solution (11 mmol) in 20 ml dioxane. A stock solution of the catalyst in dioxane was made by heating 375 mg PdCl$_2$[dppf].CH$_2$Cl$_2$ with triethylamine (7 ml) at 80° C. for 24 h in 68 ml dioxane. 5 mL of this brown solution, which contains about 25 mg of the catalyst and 0.47 ml of triethylamine, was placed in a reaction tube containing the substrate (1 mmol) under an inert atmosphere. Then 1.2 ml of the borane solution was added and the reaction mixture heated to 80° C. with stirring in a closed tube. The mixture was heated for 24 h although the reaction times varied with the substrate using longer reaction times when the substrates carried deactivating substituents or when the halide was a bromide rather than iodide. An aliquot of the reaction solution was removed after 24 h reaction time and at longer times if the reaction was not complete, dissolved in some ethyl acetate and shaken with 10% brine solution. After drying with MgSO$_4$, the gc was measured. The reaction products were identified by gc/ms. The following chiral compounds were obtained by this procedure.

(i) 2-[(1S,2S,6R,8S)-2,9,9-trimethyl-3,5-dioxa-4-boratricyclo[6.1.1.0$^{2,6}$]dec-4-yl]benzonitrile

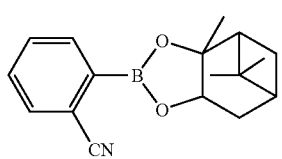

The gc of the reaction solution had only one strong peak at 15.6 mins which was shown to be due to the desired product.

(ii) (1S,2S,6R,8S)-4-(4-methoxy-2-methylphenyl)-2,9,9-trimethyl-3,5-dioxa-4-boratricyclo[6.1.1.0$^{2,6}$]decane

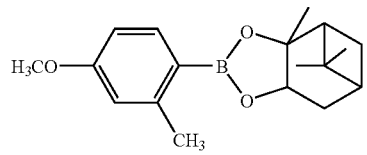

The gc of the reaction solution had only one strong peak at 15.9 mins which was shown to be due to the desired product (iii) 2,6-dimethoxy-3-[(1S,2S,6R,8S)-2,9,9-trimethyl-3,5-dioxa-4-boratricyclo[6.1.1.0$^{2,6}$]dec-4-yl]pyridine

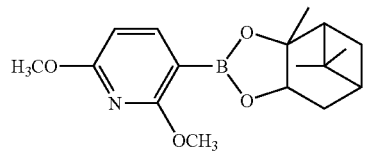

The gc of the reaction solution had only one strong peak at 15.5 mins which was shown to be due to the desired product.

(iv) (1S,2S,6R,8S)-2,9,9-trimethyl-4-(2,3,4-trimethoxyphenyl)-3,5-dioxa-4-boratricyclo[6.1.1.0$^{2,6}$]decane

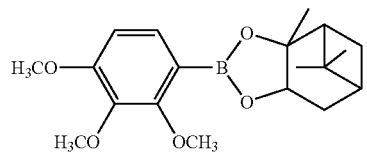

The gc of the reaction solution had only one strong peak at 17.0 mins which was shown to be due to the desired product.

(v) (1S,2S,6R,8S)-4-(2-methoxyphenyl)-2,9,9-trimethyl-3,5-dioxa-4-boratricyclo[6.1.1.0$^{2,6}$]decane

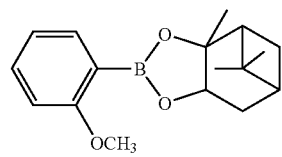

The gc of the reaction solution had only one strong peak at 14.4 mins which was shown to be due to the desired product.

(vi) (1,2S,6R,8S)-2,9,9-trimethyl-4-[2-(trifluoromethyl)phenyl]-3,5-dioxa-4-boratricyclo[6.1.1.0$^{2,6}$]decane

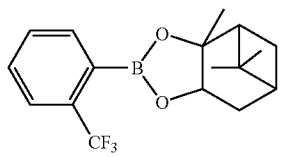

The gc of the reaction solution had only one strong peak at 12.4 mins which was shown to be due to the desired product.

(vii) (1S,2S,6R,8S)-2,9,9-trimethyl-4-(2-methylphenyl)-3,5-dioxa-4-boratricyclo[6.1.1.0$^{2,6}$]decane

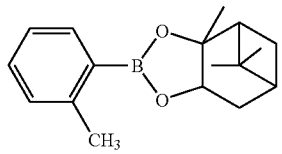

The gc of the reaction solution had only one strong peak at 13.5 mins which was shown to be due to the desired product.

Example 27

The formation of arylboronic acid esters with the chiral diol (1R,2R,3S,5R)-(−) pinanediol.

The borane (1R,2R,6S,8R)-2,9,9-trimethyl-3,5-dioxa-4-boratricyclo[6.1.1.0$^{2,6}$]decane was synthesised from the diol and BH$_3$.SMe$_2$ and reacted with aryl halides by the procedure described in Example 26. The reaction products were identified by gc/ms.

(i) 2-[(1R,2R,6S,8R)-2,9,9-trimethyl-3,5-dioxa-4-boratricyclo[6.1.1.0$^{2,6}$]dec-4-yl]benzonitrile

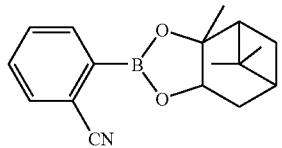

The gc of the reaction solution had only one strong peak at 15.6 mins which was shown to be due to the desired product.

(ii) (1R,2R,6S,8R)-4-(4-methoxy-2-methylphenyl)-2,9,9-trimethyl-3,5-dioxa-4-boratricyclo[6.1.1.0$^{2,6}$]decane

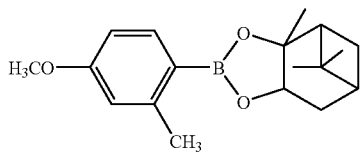

The gc of the reaction solution had only one strong peak at 15.9 mins which was shown to be due to the desired product.

(iii) 2,6-dimethoxy-3-[(1R,2R,6S,8R)-2,9,9-trimethyl-3,5-dioxa-4-boratricyclo[6.1.1.0$^{2,6}$]dec-4-yl]pyridine

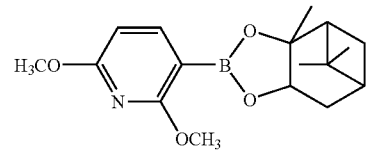

The gc of the reaction solution had only one strong peak at 15.5 mins which was shown to be due to the desired product.

(iv) (1R,2R,6S,8R)-2,9,9-trimethyl-4-(2,3,4-trimethoxyphenyl)-3,5-dioxa-4-boratricyclo[6.1.1.0$^{2,6}$]decane

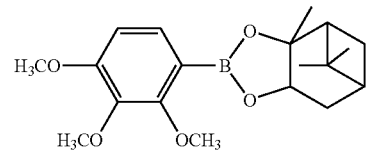

The gc of the reaction solution had only one strong peak at 17.0 mins which was shown to be due to the desired product.

(v) (1R,2R,6S,8R)-4-(2-methoxyphenyl)-2,9,9-trimethyl-3,5-dioxa-4-boratricyclo[6.1.1.0$^{2,6}$]decane

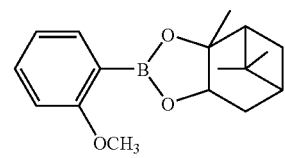

The gc of the reaction solution had only one strong peak at 14.4 mins which was shown to be due to the desired product.

(vi) (1R,2R,6S,8R)-2,9,9-trimethyl-4-[2-(trifluoromethyl)phenyl]-3,5-dioxa-4-boratricyclo[6.1.1.0$^{2,6}$]decane

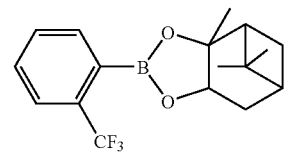

The gc of the reaction solution had only one strong peak at 12.4 mins which was shown to be due to the desired product.

(vii) (1R,2R,6S,8R)-2,9,9-trimethyl-4-(2-methylphenyl)-3,5-dioxa-4-boratricyclo[6.1.1.0$^{2,6}$]decane

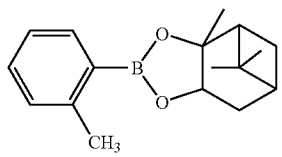

The gc of the reaction solution had only one strong peak at 13.5 mins which was shown to be due to the desired product.

Example 28

Formation of the hydroxyphenylboronic acid pinacol esters using catalyst (PdCl$_2$[dppf].CH$_2$Cl$_2$) that had been activated by heating with triethylamine in dioxane prior to use in the reactions.

Formation of 2-(4,4,5,5-tetramethyl-1,3,2-dioxaborolan-2-yl)phenol

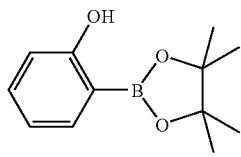

27 mg of PdCl$_2$[dppf].CH$_2$Cl$_2$ was placed in a reaction tube under nitrogen together with 4 ml dioxane and 0.45 ml triethylamine. The mixture was heated at 80° C. for 17 h to give a brownish solution. To this solution was then added 224 mg (1.02 mmol) of 2-iodophenol and 0.4 ml (2.7 mmol) pinacolborane (HB(pin)). The reaction mixture was heated with stirring to 80° C. and was followed by gc and the products identified by gc/ms. The gc solutions were prepared by washing an aliquot of the reaction solution dissolved in ethyl acetate containing some pinacol with acidified water and then with brine (twice) and dried. After 2 h reaction, the desired product peak in the gc was of area % 74. The reaction was complete after 6 h with very little phenylboronic acid pinacol ester formed.

Formation of 3-(4,4,5,5-tetramethyl-1,3,2-dioxaborolan-2-yl)phenol

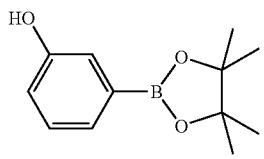

The above reaction procedure used for 2-iodophenol was followed. The reaction was faster, being complete before the first sample for gc analysis was withdrawn after 1 h 50 min reaction time. The amount of phenylboronic acid pinacol ester was higher than in the 2-iodophenol reaction (around 7%).

Formation of 4-(4,4,5,5-tetramethyl-1,3,2-dioxaborolan-2-yl)phenol

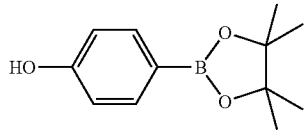

The above reaction procedure used for 2-iodophenol was followed. The reaction was also faster, being again complete before the first sample for gc analysis was withdrawn after 1 h 50 min reaction time. The amount of phenylboronic acid pinacol ester was about that found in the 3-iodophenol reaction. The reaction in which 4-bromophenol is used as substrate is slower but does go to completion. Pinacolborane prepared in situ from the dimethylsulfide adduct of borane can also be used with both the 4-bromophenol and 4-iodophenol.

Example 29

Reaction of an aryl aldehyde to give the boronic acid ester.

Formation of 3,4-dimethoxy-5-(4,4,5,5-tetramethyl-1,3,2-dioxaborolan-2-yl)benzaldehyde

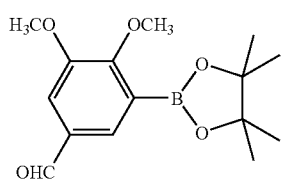

25 mg of PdCl$_2$[dppf].CH$_2$Cl$_2$ was placed in a reaction tube under nitrogen and added 4 ml dioxane and 0.45 ml triethylamine. The mixture was heated at 80° C. for 19 h to give a brownish solution. To this solution was then added 0.4 ml (2.7 mmol) pinacolborane and 393 mg (1.35 mmol) of 3-iodo-4,5-dimethoxybenzaldehyde. The reaction mixture was heated with stirring to 80° C. and was analysed by gc after 16.5 h and the products identified by gc/ms. The reaction was complete and the product distribution, as gauged by gc peak areas, was desired product 89%, dehalogenated species 7%, starting iodide 1% and phenylboronic acid pinacol ester 2%.

Example 30

Formation of the carbethoxyphenylboronic acid pinacol esters using catalyst (PdCl$_2$[dppf].CH$_2$Cl$_2$) that had been activated by heating with triethylamine in dioxane prior to use in the reactions.

Formation of ethyl 2-(4,4,5,5-tetramethyl-1,3,2-dioxaborolan-2-yl)benzoate

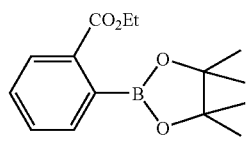

25.5 mg of PdCl$_2$[dppf].CH$_2$Cl$_2$ was placed in a reaction tube under nitrogen and added 4 ml dioxane and 0.45 ml triethylamine. The mixture was heated at 80° C. for 23 h to give a brownish solution. To this solution was then added 286 mg (1.04 mmol) of ethyl 2-iodobenzoate and 0.23 ml (1.6 mmol) pinacolborane. The reaction mixture was heated with stirring to 80° C. for 16.5 h and then analysed by gc and the products identified by gc/ms. The gc solutions were prepared by washing an aliquot of the reaction solution dissolved in ethyl acetate with water and dried. The reaction was finished, the desired product peak in the gc had an area of 84% with the only other significant peak being that due to the dehalogenation product, ethyl benzoate (14%).

Formation of ethyl 3-(4,4,5,5-tetramethyl-1,3,2-dioxaborolan-2-yl)benzoate

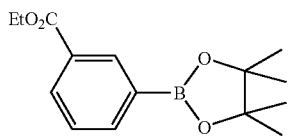

The above reaction procedure used for ethyl 2-iodobenzoate was followed. The reaction was finished, the desired product peak in the gc had an area of 79% with the only other significant peak being that due to the dehalogenation product, ethyl benzoate (16%).

Formation of ethyl 4-(4,4,5,5-tetramethyl-1,3,2-dioxaborolan-2-yl)benzoate

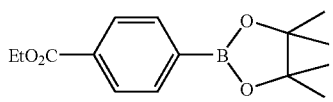

The reaction procedure used for ethyl 2-iodobenzoate was followed. After 80 mins. reaction time, the yield of product, by gc, was 44% and the reaction was complete when analysed after 24 h.

Example 31

Reaction of a phenol with a trialkyl borate prior to its reaction with an HB(OR)$_2$ type species so that less of this reagent is required to form the borate ester of the phenol. In particular, in this example two equivalents of p-iodophenol is reacted with one equivalent of triethyl borate and the product is then reacted with 2.4 equivalents of pinacolborane. If the initial reaction with triethyl borate is omitted, at least four equivalents of the borane reagent is required for this reaction to proceed to completion.

Formation of 4-(4,4,5,5-tetramethyl-1,3,2-dioxaborolan-2-yl)phenol

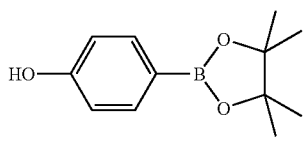

440 mg (2 mmol) of p-iodophenol were placed in a Schlenk flask with 100 ml of dry benzene and 0.17 ml of triethyl borate (1 mmol). The solution was heated for 1.5 h under an inert atmosphere (argon) at 80° C. and then the benzene and ethanol formed were distilled off the product after raising the oil bath temperature to 100° C. To the liquid in the Schlenk was then added 10 ml of activated catalyst (PdCl$_2$[dppf].CH$_2$Cl$_2$) solution, prepared as described in Example 26, followed by 0.35 ml (2.4 mmol) of pinacolborane. No frothing indicating H$_2$ evolution, which would suggest free phenol groups, was observed. The reaction solution was then heated at 80° C. for 7.5 h before removal of an aliquot for gc analysis. This sample was washed in ethyl acetate with 10% brine as described elsewhere. Only two peaks were observed in the gc with retention time longer than 2 minutes and these corresponded to phenylboronic acid pinacol ester (area approx. 7.5%) and with the desired product contributing the remaining area (92.5%).

Example 32

2-(1,2-Dimethyl-1-propenyl)-4,4,5,5-tetramethyl-1,3,2-dioxaborolane

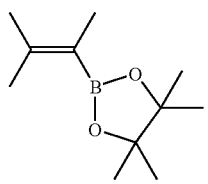

In a reaction tube under nitrogen, a mixture of PdCl$_2$(dppf)CH$_2$Cl$_2$ (22 mg; 0.027 mmol) and triethylamine (0.36 ml; 2.58 mmol) in dioxane (4 ml; dried over 4 Å sieves) was sealed and stirred at 80° C. overnight (18 h). After cooling to room temperature, 1.29M HB(pin) in dioxane (1.00 ml; 1.29 mmol) and 2-bromo-3-methyl-2-butene (131 mg; 0.879 mmol) were added and the reaction mixture was stirred at 80° C. GC analysis after 24 hours showed a new peak at 5.0 minutes which was identified by GC/MS as the desired borate compound.

Example 33

1,3-Dimethyl-5-(4,4,5,5-tetramethyl-1,3,2-dioxaborolan-2-yl)-2,4(1H,3H)-pyrimidinedione

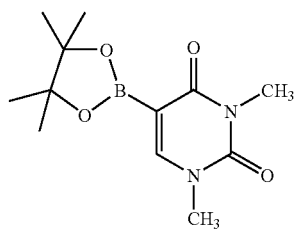

In a reaction tube under nitrogen, a mixture of PdCl$_2$(dppf)CH$_2$Cl$_2$ (22 mg; 0.027 mmol) and triethylamine (0.36 ml; 2.58 mmol) in dioxane (4 ml; dried over 4 Å sieves) was sealed and stirred at 80° C. overnight (18 hours). After cooling to room temperature, 1.29M HB(pin) in dioxane (1.00 ml; 1.29 mmol) and 5-iodo-1,3-dimethyluracil (228 mg; 0.857 mmol) were added and the reaction mixture was stirred at 80° C. GC analysis after 8 hours showed the desired borate compound at 20.3 minutes.

Example 34

2-(1,2-Dimethyl-1-propenyl)-4,4,5,5-tetramethyl-1,3,2-dioxaborolane

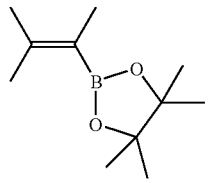

In a reaction tube under nitrogen, a mixture of PdCl$_2$(dppf)CH$_2$Cl$_2$ (21 mg; 0.026 mmol), triethylamine (0.36 ml; 2.58 mmol), 2-bromo-3-methyl-2-butene (132 mg; 0.886 mmol), 1.29M HB(pin) in dioxane (1.00 ml; 1.29 mmol) and N-methylacetamide (39 mg; 0.53 mmol) in dioxane (4 ml; dried over 4 Å sieves) was sealed and stirred at 80° C. GC analysis after 24 hours showed formation of the desired alkenylborate compound which was also identified by GC/MS.

Example 35

4,4,5,5-Tetramethyl-2-(1,2,2-triphenylvinyl)-1,3,2-dioxaborolane

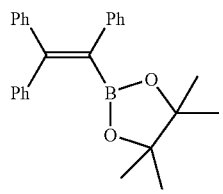

In a reaction tube under nitrogen, a mixture of PdCl$_2$(dppf)CH$_2$Cl$_2$ (21 mg; 0.026 mmol) and triethylamine (0.36 ml; 2.58 mmol) in dioxane (4 ml; dried over 4 Å sieves) was sealed and stirred at 80° C. overnight (18 h). After cooling to room temperature, 1.29M HB(pin) in dioxane (1.00 ml; 1.29 mmol) and bromotriphenylethylene (289 mg; 0.862 mmol) were added and the reaction mixture was stirred at 80° C. GC analysis after 24 hours showed a new peak at 16.9 minutes which was identified by GC/MS as the desired alkenylborate compound.

Example 36

Ethyl (Z)-3-(4,4,5,5-tetramethyl-1,3,2-dioxaborolan-2-yl)-2-propenoate

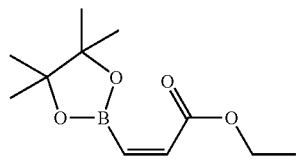

In a reaction tube under nitrogen, a mixture of PdCl$_2$(dppf)CH$_2$Cl$_2$ (22 mg; 0.027 mmol) and triethylamine (0.36 ml; 2.58 mmol) in dioxane (4 ml; dried over 4 Å sieves) was sealed and stirred at 80° C. overnight (18 h). After cooling to room temperature, 1.29M HB(pin) in dioxane (1.00 ml; 1.29 mmol) and ethyl cis-3-iodoacrylate (193 mg; 0.854 mmol) were added and the reaction mixture was stirred at 80° C. GC analysis after 24 hours showed the desired borate compound at 8.4 minutes. GC/MS found [M-Et]$^+$.

Example 37

4,4,5,5-Tetramethyl-2-phenyl-1,3,2-dioxaborolane

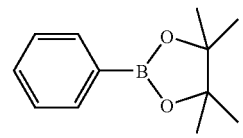

In a reaction tube under nitrogen, a mixture of PdCl$_2$(dppf)CH$_2$Cl$_2$ (23 mg; 0.028 mmol) and triethylamine (0.36 ml; 2.58 mmol) in dioxane (4 ml; dried over 4 Å sieves) was sealed and stirred at 80° C. overnight (18 h). After cooling to room temperature, 1.29M HB(pin) in dioxane (1.00 ml; 1.29 mmol) and phenyl trifluoromethanesulfonate (197 mg; 0.871 mmol) were added and the reaction mixture was stirred at 80° C. GC analysis after 4 days showed a new peak at 7.4 minutes which was identified by GC/MS as the desired phenylborate compound.

Example 38

5-(4,4,5,5-Tetramethyl-1,3,2-dioxaborolan-2-yl)-1,3-benzodioxole

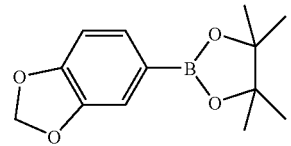

In a reaction tube under nitrogen, a mixture of PdCl$_2$(dppf)CH$_2$Cl$_2$ (22 mg; 0.027 mmol) and triethylamine (0.36 ml; 2.58 mmol) in dioxane (4 ml; dried over 4 Å sieves) was sealed and stirred at 80° C. overnight (18 h). After cooling to room temperature, HB(pin) (0.18 ml; 0.24 mmol), 1-iodo-3,4-methylenedioxybenzene (216 mg; 0.871 mmol) and N-methylacetamide (39 mg; 0.56 mmol) were added and the reaction mixture was stirred at 80° C. GC analysis after 30 minutes showed a new peak at 11.1 minutes (51%) which was identified by GC/MS as the desired arylborate compound.

Example 39

Ethyl 4-methoxy-3-(4,4,5,5-tetramethyl-1,3,2-dioxaborolan-2-yl)benzoate

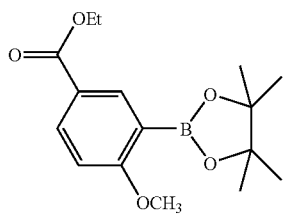

In a reaction tube under nitrogen, a mixture of PdCl$_2$(dppf)CH$_2$Cl$_2$ (24 mg; 0.029 mmol) and triethylamine (0.36 ml; 2.58 mmol) in dioxane (4 ml; dried over 4 Å sieves) was sealed and stirred at 80° C. overnight (18 h). After cooling to room temperature, HB(pin) (0.18 ml; 1.24 mmol) and ethyl 3-iodo-4-methoxybenzoate (266 mg; 0.869 mmol) were added and the reaction mixture was stirred at 80° C. GC analysis after 3 days showed a new peak at 14.6 minutes which was identified by GC/MS as the desired arylborate compound.

Example 40

4,4,5,5-Tetramethyl-2-(2-thienyl)-1,3,2-dioxaborolane

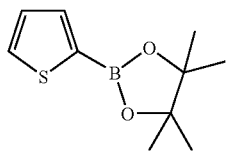

In a reaction tube under nitrogen, a mixture of PdCl$_2$(dppf)CH$_2$Cl$_2$ (21 mg; 0.026 mmol) and triethylamine (0.36 ml; 2.58 mmol) in dioxane (4 ml; dried over 4 Å sieves) was sealed and stirred at 80° C. overnight (18 h). After cooling to room temperature, HB(pin) (0.18 ml; 1.24 mmol) and 2-iodothiophene (177 mg; 0.843 mmol) were added and the reaction mixture was stirred at 80° C. GC analysis after 3 days showed a new peak at 7.4 minutes which was identified by GC/MS as the desired heterocyclic borate compound.

Example 41

5-(4,4,5,5-Tetramethyl-1,3,2-dioxaborolan-2-yl)-1,3-benzodioxole

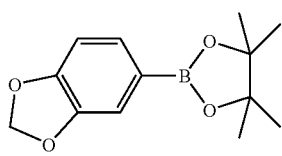

In a reaction tube under nitrogen, a mixture of PdCl$_2$(dppf)CH$_2$Cl$_2$ (23 mg; 0.028 mmol), triethylamine (0.36 ml; 2.58 mmol), HB(pin) (0.19 ml; 1.31 mmol), 1-iodo-3,4-methylenedioxybenzene (216 mg; 0.871 mmol) and N,N-dimethylacetamide (41 mg; 0.47 mmol) in dioxane (5 ml; dried over 4 Å sieves) was sealed and stirred at 80° C. GC analysis after 24 hours showed the reaction was complete and the desired arylborate compound had formed (new peak at 11.2 minutes).

Example 42

4,4,5,5-Tetramethyl-2-phenyl-1,3,2-dioxaborolane

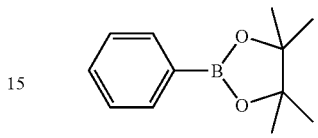

In a reaction tube under nitrogen, a mixture of PdCl$_2$(dppf)CH$_2$Cl$_2$ (22 mg; 0.027 mmol), triethylamine (0.36 ml; 2.58 mmol), HB(pin) (0.19 ml; 1.31 mmol), phenyl trifluoromethanesulfonate (192 mg; 0.849 mmol) and acetanilide (61 mg; 0.45 mmol) in dioxane (4.5 ml; dried over 4 Å sieves) was sealed and stirred at 80° C. GC analysis after 24 hours shows the reaction to be complete and having formed the desired arylborate compound (new peak at 7.5 minutes).

Example 43

4,4,5,5-Tetramethyl-2-(2,4,6-trichlorophenyl)-1,3,2-dioxaborolane

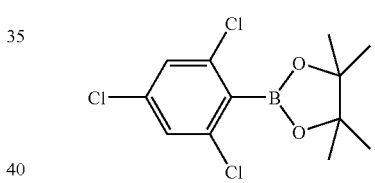

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 1-iodo-2,4,6-trichlorobenzene (267 mg; 0.869 mmol) in dioxane (2.5 ml; dried over 4 Å sieves) and the reaction mixture was stirred at 80° C. GC analysis after 18 hours showed a new peak at 12.5 minutes which was identified by GC/MS as the desired arylborate compound.

Example 44

Methyl 2-(acetylamino)-5-(4,4,5,5-tetramethyl-1,3,2-dioxaborolan-2-yl)benzoate

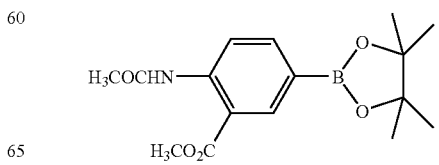

In a reaction tube under nitrogen, a mixture of PdCl₂(dppf)CH₂Cl₂ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.31 ml; 2.14 mmol) was added followed by methyl 2-acetamido-5-bromobenzoate (233 mg; 0.856 mmol) in dioxane (2.5 ml; dried over 4 Å sieves) and the reaction mixture was stirred at 80° C. GC analysis after 18 hours showed a new peak at 16.4 minutes which was identified by GC/MS as the desired arylborate compound.

Example 45

Phenyl[4-(4,4,5,5-tetramethyl-1,3,2-dioxaborolan-2-yl)phenyl]methanone

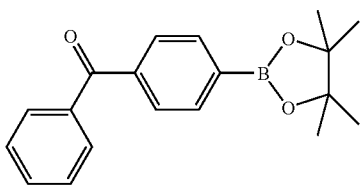

In a reaction tube under nitrogen, a mixture of PdCl₂(dppf)CH₂Cl₂ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 4-bromobenzophenone (233 mg; 0.869 mmol) in dioxane (2.5 ml; dried over 4 Å sieves) and the reaction mixture was stirred at 80° C. GC analysis after 18 hours showed a new peak at 17.0 minutes which was identified by GC/MS as the desired arylborate compound.

Example 46

4,4,5,5-Tetramethyl-2-(2,4,6-trimethoxyphenyl)-1,3,2-dioxaborolane

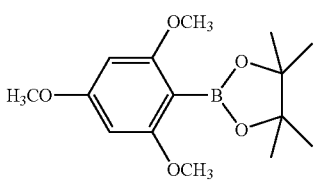

In a reaction tube under nitrogen, a mixture of PdCl₂(dppf)CH₂Cl₂ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 1-iodo-2,4,6-trimethoxybenzene (253 mg; 0.861 mmol) in dioxane (2.5 ml; dried over 4 Å sieves) and the reaction mixture was stirred at 80° C. GC analysis after 18 hours showed a single new peak at 14.2 minutes which was identified by GC/MS as the desired arylborate compound.

Example 47

2-(4-Methoxy-3-methylphenyl)-4,4,5,5-tetramethyl-1,3,2-dioxaborolane

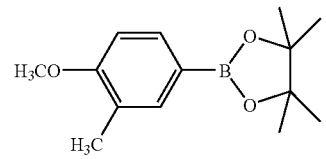

In a reaction tube under nitrogen, a mixture of PdCl₂(dppf)CH₂Cl₂ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 1-iodo-4-methoxy-3-methylbenzene (215 mg; 0.867 mmol) in dioxane (2.5 ml; dried over 4 Å sieves) and the reaction mixture was stirred at 80° C. GC analysis after 18 hours showed a single new peak at 11.4 minutes which was identified by GC/MS as the desired arylborate compound.

Example 48

2-(2,4-Dimethoxyphenyl)-4,4,5,5-tetramethyl-1,3,2-dioxaborolane

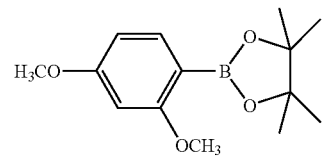

In a reaction tube under nitrogen, a mixture of PdCl₂(dppf)CH₂Cl₂ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 1-iodo-2,4-dimethoxybenzene (227 mg; 0.860 mmol) in dioxane (2.5 ml; dried over 4 Å sieves) and the reaction mixture was stirred at 80° C. GC analysis after 2 days showed a new peak at 11.0 minutes which was identified by GC/MS as the desired arylborate compound.

Example 49

2-(2-Methoxy-1-naphthyl)-4,4,5,5-tetramethyl-1,3,24-dioxaborolane

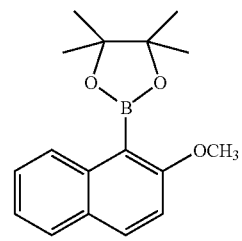

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 1-iodo-2-methoxy naphthalene (245 mg; 0.862 mmol) in dioxane (2.5 ml; dried over 4 Å sieves) and the reaction mixture was stirred at 80° C. GC analysis after 2 days showed the desired arylborate compound at 14.3 minutes.

Example 50

2-(2-Bromophenyl)-4,4,5,5-tetramethyl-1,3,2-dioxaborolane and 4,4,5,5-Tetramethyl-2-[2-(4,4,5,5-tetramethyl-1,3,2-dioxaborolan-2-yl)phenyl]-1,3,2-dioxaborolane

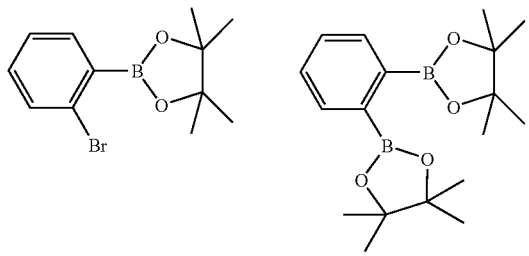

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 1-bromo-2-iodo-benzene (245 mg; 0.866 mmol) in dioxane (2.5 ml; dried over 4 Å sieves) and the reaction mixture was stirred at 80° C. GC analysis after 2 days detected the monoborate at 8.9 minutes and the diborate at 12.9 minutes.

Example 51

2-(4-Bromophenyl)-4,4,5,5-tetramethyl-1,3,2-dioxaborolane and 4,4,5,5-Tetramethyl-2-[4-(4,4,5,5-tetramethyl-1,3,2-dioxaborolan-2-yl)phenyl]-1,3,2-dioxaborolane

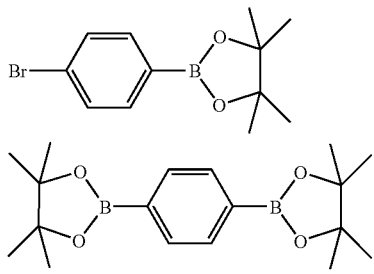

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 1-bromo-4-iodobenzene (242 mg; 0.855 mmol) in dioxane (2.5 ml; dried over 4 Å sieves) and the reaction mixture was stirred at 80° C. GC analysis after 18 hours showed the monoborate at 8.8 minutes and the diborate at 13.7 minutes.

Example 52

2-(4-Chlorophenyl)-4,4,5,5-tetramethyl-1,3,2-dioxaborolane

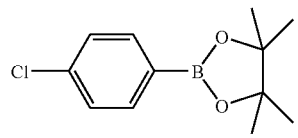

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 4-chloro-iodobenzene (209 mg; 0.876 mmol) in dioxane (2.5 ml; dried over 4 Å sieves) and the reaction mixture was stirred at 80° C. GC analysis after 18 hours showed the desired borate compound at 7.7 minutes.

Example 53

4,4,5,5-Tetramethyl-2-[4-(trifluoromethyl)phenyl]-1,3,2-dioxaborolane

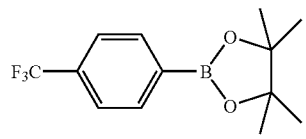

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 4-iodobenzotrifluoride (235 mg; 0.864 mmol) in dioxane (2.5 ml; dried over 4 Å sieves) and the reaction mixture was stirred at 80° C. GC analysis after 18 hours showed the desired borate compound at 5.0 minutes.

Example 54

4-(4,4,5,5-Tetramethyl-1,3,2-dioxaborolan-2-yl)-1H-pyrazole

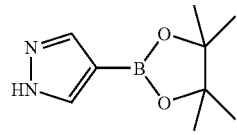

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.31 ml; 2.14 mmol) was added followed by 4-iodopyrazole (166 mg; 0.856 mmol) in dioxane (2.5 ml; dried over 4 Å sieves) and the reaction mixture was stirred at 80° C. GC analysis after 18 hours showed the desired borate compound at 7.4 minutes.

Example 55

3-(4,4,5,5-Tetramethyl-1,3,2-dioxaborolan-2-yl)benzylamine

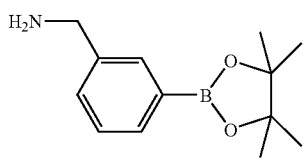

In a reaction tube under nitrogen, a mixture of $PdCl_2$ (dppf)$CH_2Cl_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.32 ml; 2.21 mmol) was added followed by 3-iodobenzylamine (201 mg; 0.862 mmol) in dioxane (2.5 ml; dried over 4 Å sieves) and the reaction mixture was stirred at 80° C. GC analysis after 18 hours showed the desired borate compound at 10.0 minutes.

Example 56

4,4,5,5-Tetramethyl-2-(3,4,5-trimethoxyphenyl)-1,3,2-dioxaborolane

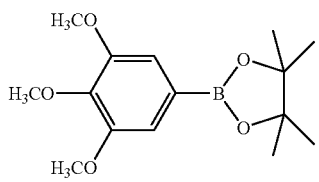

In a reaction tube under nitrogen, a mixture of $PdCl_2$ (dppf)$CH_2Cl_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 1-bromo-3,4,5-trimethoxybenzene (213 mg; 0.862 mmol) in dioxane (2.5 ml; dried over 4 Å sieves) and the reaction mixture was stirred at 80° C. GC analysis after 18 hours showed the desired borate compound at 12.0 minutes.

Example 57

4,4,5,5-Tetramethyl-2-(3-thienyl)-1,3,2-dioxaborolane

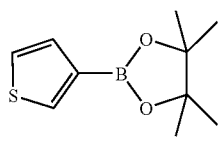

In a reaction tube under nitrogen, a mixture of $PdCl_2$ (dppf)$CH_2Cl_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 3-bromothiophene (137 mg; 0.840 mmol) in dioxane (2.5 ml; dried over 4 Å sieves) and the reaction mixture was stirred at 80° C. GC analysis after 18 hours showed the desired borate compound at 5.1 minutes.

Example 58

Methyl 4-methoxy-3-(4,4,5,5-tetramethyl-1,3,2-dioxaborolan-2-yl)benzoate

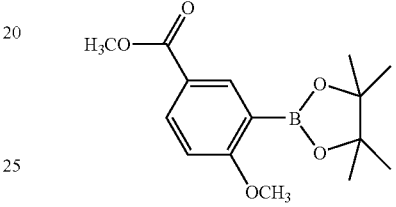

In a reaction tube under nitrogen, a mixture of $PdCl_2$ (dppf)$CH_2Cl_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by methyl 3-iodo-4-methoxybenzoate (251 mg; 0.859 mmol) in dioxane (2.5 ml; dried over 4 Å sieves) the reaction mixture was stirred at 80° C. GC analysis after 18 hours showed the desired borate compound at 13.0 minutes.

Example 59

4,4,5,5-Tetramethyl-2-(2,3,4,6-tetramethoxyphenyl)-1,3,2-dioxaborolane

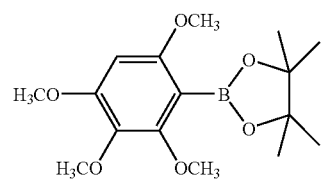

In a reaction tube under nitrogen, a mixture of $PdCl_2$ (dppf)$CH_2Cl_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.199 ml; 1.31 mmol) was added followed by methyl-2,3,4,6-tetramethoxy-iodobenzene (274 mg; 0.845 mmol) in dioxane (2.5 ml; dried over 4 Å sieves) the reaction mixture was stirred at 80° C. GC analysis after 2 days showed the desired borate compound at 13.3 minutes.

Example 60

N-[2-Methyl-4-(4,4,5,5-tetramethyl-1,3,2-dioxaborolan-2-yl)phenyl]acetamide

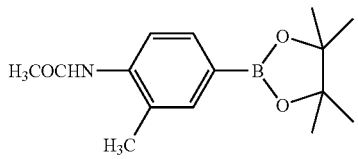

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml dried over 4 Å sieves) was sealed and stirred at 80° C. overnight (18 h). After cooling to room temperature, HB(pin) (0.19 ml; 1.31 mmol) was added followed by 4'-bromo-2'-methylacetanilide (197 mg; 0.864 mmol) in dioxane (2.5 ml; dried over 4 Å sieves) the reaction mixture was stirred at 80° C. GC analysis after 2 days showed the desired borate compound at 14.5 minutes.

Example 61

2-(6-Methoxy-2-naphthyl)-4,4,5,5-tetramethyl-1,3,2-dioxaborolane

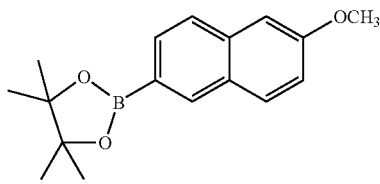

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 6-bromo-2-methoxynaphthalene (204 mg; 0.860 mmol) in dioxane (2.5 ml; dried over 4 Å sieves) the reaction mixture was stirred at 80° C. GC analysis after 2 days showed the desired borate compound at 14.6 minutes.

Example 62

2,4-Dimethoxy-5-(4,4,5,5-tetramethyl-1,3,2-dioxaborolan-2-yl)pyrimidine

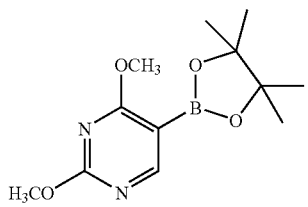

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 5-bromo-2,4-dimethoxypyrimidine (190 mg; 0.867 mmol) in dioxane (2.5 ml; dried over 4 Å sieves) the reaction mixture was stirred at 80° C. GC analysis after 2 days showed the desired borate compound at 8.9 minutes.

Example 63

2-(2-Fluoro[1,1'-biphenyl]-4-yl)-4,4,5,5-tetramethyl-1,3,2-dioxaborolane

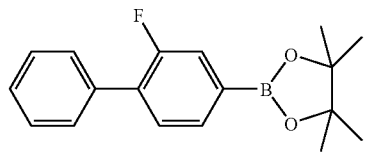

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature HB(pin) (0.19 ml; 1.31 mmol) was added followed by 4-bromo-2-fluorodiphenyl (213 mg; 0.848 mmol) in dioxane (2.5 ml; dried over 4 Å sieves) the reaction mixture was stirred at 80° C. GC analysis after 2 days showed the desired borate compound at 19.4 minutes.

Example 64

3,4-Dimethoxy-5-(4,4,5,5-tetramethyl-1,3,2-dioxaborolan-2-yl)benzaldehyde

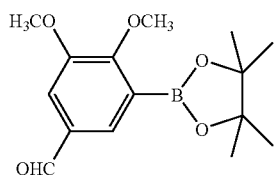

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 3-iodo-4,5-dimethoxybenzaldehyde (254 mg; 0.870 mmol) in dioxane (2.5 ml; dried over 4 Å sieves) the reaction mixture was stirred at 80° C. GC analysis after 2 days showed the desired borate compound at 13.2 minutes.

Example 65

2-(4-Methoxy-1-naphthyl)-4,4,5,5-tetramethyl-1,3,2-dioxaborolane

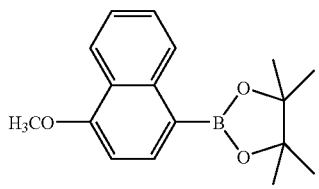

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 1-bromo-4-methoxynaphthalene (207 mg; 0.873 mmol) in dioxane (2.5 ml; dried over 4 Å sieves) the reaction mixture was stirred at 80° C. GC analysis after 2 days showed the desired borate compound at 14.7 minutes.

Example 66

4-[4-(4,4,5,5-Tetramethyl-1,3,2-dioxaborolan-2-yl)phenyl]-1,3-thiazol-2-amine

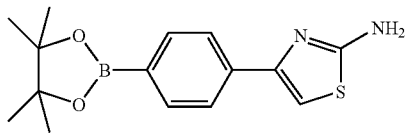

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.32 ml; 2.21 mmol) was added followed by 2-amino-4-(4-bromophenyl)thiazole (213 mg; 0.858 mmol) in dioxane (2.5 ml; dried over 4 Å sieves) the reaction mixture was stirred at 80° C. GC analysis after 2 days showed the desired borate compound at 17.5 minutes.

Example 67

4,4,5,5-Tetramethyl-2-(4-{[(E)-3-methyl-1-butenyl]oxy}phenyl)-1,3,2-dioxaborolane

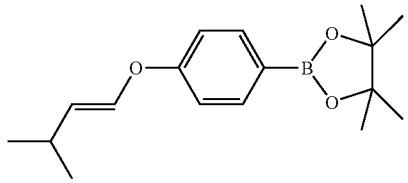

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 1-bromo-4-[(3-methylbut-2-enyl)oxy]benzene (209 mg; 0.867 mmol) in dioxane (2.5 ml; dried over 4 Å sieves) the reaction mixture was stirred at 80° C. GC analysis after 2 days showed the desired borate compound at 12.8 minutes.

Example 68

1-[4'-(4,4,5,5-Tetramethyl-1,3,2-dioxaborolan-2-yl)[1,1'-biphenyl]4-yl]-1-ethanone

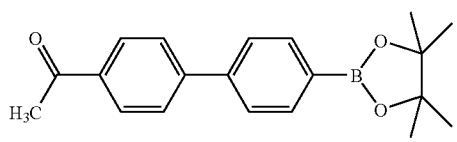

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.19 ml; 1.31 mmol) was added followed by 4-acetyl-4'-bromobiphenyl (240 mg; 0.872 mmol) in dioxane (2.5 ml; dried over 4 Å sieves) the reaction mixture was stirred at 80° C. GC analysis after 2 days showed the desired borate compound at 17.3 minutes.

Example 69

3-Bromo-6-(4,4,5,5-tetramethyl-1,3,2-dioxaborolan-2-yl)-9H-carbazole

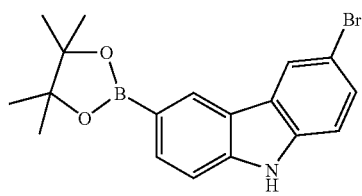

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.32 ml; 2.21 mmol) was added followed by 3,6-dibromocarbazole (281 mg; 0.865 mmol) in dioxane (2.5 ml; dried over 4 Å sieves) the reaction mixture was stirred at 80° C. GC analysis after 18 hours showed the desired borate compound at 21.3 minutes.

Example 70

6-(4,4,5,5-Tetramethyl-1,3,2-dioxaborolan-2-yl)-2-naphthol

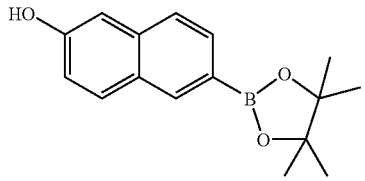

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature, HB(pin) (0.32 ml; 2.21 mmol) was added followed by 6-bromo-2-naphthol (189 mg; 0.847 mmol) in dioxane (2.5 ml; dried over 4 Å sieves) the reaction mixture was stirred at 80° C. GC analysis after 18 hours showed the desired borate compound at 16.0 minutes.

Example 71

4,4-Dimethyl-2-(4,4,5,5-tetramethyl-1,3,2-dioxaborolan-2-yl)-2-cyclohexen-1-one

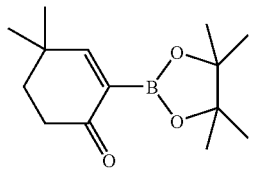

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature HB(pin) (0.19 ml; 1.31 mmol) was added followed by 4,4-dimethyl-2-iodo-2-cyclohexenone (213 mg; 0.852 mmol) in dioxane (2.5 ml; dried over 4 Å sieves) the reaction mixture was stirred at 80° C. GC analysis after 18 hours showed the desired borate compound at 9.2 minutes.

Example 72

2-(4-Methoxyphenyl)-4,4,5,5-tetramethyl-1,3,2-dioxaborolane

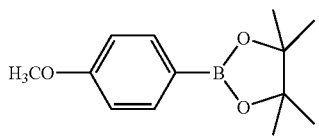

In a reaction tube under nitrogen, a mixture of PdCl$_2$(dppf)CH$_2$Cl$_2$ (21 mg; 0.026 mmol) and triethylamine (0.34 ml; 2.44 mmol) in dioxane (2.5 ml; dried over 4 Å sieves) was sealed and stirred at 80° C. overnight (18 h). After cooling to room temperature HB(pin) (0.19 ml; 1.31 mmol) was added followed by 4-methoxybenzenediazonium tetrafluoroborate (188 mg; 0.847 mmol) in dioxane (2.5 ml; dried over 4 Å sieves) the reaction mixture was stirred at 80° C. GC analysis after 18 hours showed the desired borate compound at 12.0 minutes.

Example 73

5-(4,4,5,5-Tetramethyl-1,3,2-dioxaborolan-2-yl)-1,3-benzodioxole

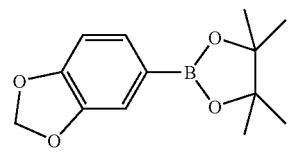

In a reaction tube under nitrogen, a mixture of PdCl$_2$(dppf)CH$_2$Cl$_2$ (24 mg; 0.029 mmol) and triethylamine (0.36 ml; 2.58 mmol) in dimethylsulphoxide (4 ml; dried over 4 Å sieves) was sealed and stirred at 80° C. for 18 hours. After cooling to room temperature HB(pin) (0.19 ml; 1.31 mmol) was added followed by 1-iodo-3,4-methylenedioxybenzene (211. mg; 0.851 mmol). The reaction mixture was stirred at 80° C. GC analysis after 18 hours showed that the desired arylborate compound had formed.

Example 74

2-methoxy-4-(4,4,5,5-tetramethyl-1,3,2-dioxaborolan-2-yl)-phenol

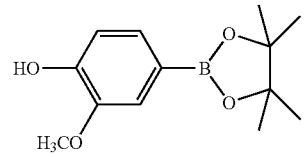

Solution 1: Pinacol (124.6 g; 1.054 mol) in dry dioxane (200 ml) was stirred under N$_2$ and allowed to equilibrate to RT.

Solution 2: Borane-methyl sulphide complex (100 ml; 10M; 1.00 mol) in dioxane (250 ml) was stirred at RT under N$_2$.

Solution 3: PdCl$_2$(dppf)CH$_2$Cl$_2$ (7.27 g; 8.90 mmol; 2 mole %) and NEt$_3$ (25.0 ml; 0.179 mol) in dry dioxane (300 ml) was stirred at 80° C., under N$_2$, overnight before cooling to room temperature.

Solution 1 was transferred under N$_2$ to a pressure-equalising dropping funnel and added to Solution 2 over 6 h. Stirred at RT overnight before heating at 40–50° C. for ~8 h. After stirring overnight at RT a white ppt had formed. NEt$_3$ (149 ml; 1.07 mol) was added followed by slow addition of 2-methoxy-4-bromophenol (91.6 g; 0.451 mol). Finally, the activated catalyst (Solution 3) was added and the resultant dark brown solution was stirred at 100° C. GC analysis after 20 hours showed the desired borate compound at 11.1 minutes (62%).

Example 75

2-methoxy-5-(4,4,5,5-tetramethyl-1,3,2-dioxaborolan-2-yl)-phenol

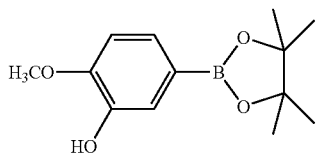

A solution of pinacol (11.29 g; 0.0955 mol) in dry dioxane (40 ml) was added dropwise, over an hour, to a solution of borane-methyl sulphide complex (9.0 ml; 10M; 0.090 mol) in dioxane (40 ml) and stirred at RT under $N_2$. To his solution was added HB(pin) (22.0 ml; 0.152 mol) and 2-methoxy-5-bromophenol (19.63 g; 0.0967 mol) in dioxane (30 ml). This solution was allowed to stir overnight at room temperature before being added, dropwise, to the activated catalyst [PdCl$_2$(dppf)CH$_2$Cl$_2$ (2.38 g; 2.91 mmol) and NEt$_3$ (40.0 ml; 0.287 mol) in dry dioxane (450 ml) heated at 80° C. and allowed to cool to RT]. The reaction mixture was heated at 100° C. GC analysis after 18 hours showed the desired borate compound at 12.0 minutes.

Example 76

2-(4,4,5,5-Tetramethyl-1,3,2-dioxaborolan-2-yl)aniline

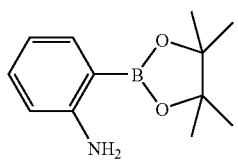

PdCl$_2$(dppf)CH$_2$Cl$_2$ (26 mg; 0.032 mmol) and NEt$_3$ (0.43 ml; 3.09 mmol) in dry dioxane (4 ml) was heated at 80° C. overnight and allowed to cool to RT. A solution of 2-bromoaniline (181 mg; 1.05 mmol) and HB(pin) (0.37 ml; 2.55 mmol) in 1.5 ml dry dioxane was stirred at RT overnight before being added to the activated catalyst above. The mixture was then heated at 80° C. GC analysis after 18 hours showed the desired borate compound at 9.8 minutes which was also identified by NMR.

Example 77

4,4,5,5-tetramethyl-2-(4-nitrophenyl)-1,3,2-dioxaborolane

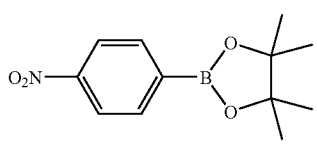

In a reaction vessel under argon, a mixture of a PdCl$_2$(dppf)CH$_2$Cl$_2$ (0.49 g; 0.602 mmol) and triethylamine (1.2 ml; 8.5 mmol) in dioxane (14.8 ml; dried over 4 Å sieves) was sealed and stirred at 80° C. overnight (18 h). After cooling to room temperature, HB(pin) (22 ml in dioxane; 1.38 M; 0.03 mol), triethylamine (8.5 ml; 0.06 mol) and 1-iodo-4-nitrobenzene (5.0 g; 0.02 mol) were added and the reaction mixture was stirred at 80° C. GC analysis after 23 h showed a peak at 11.9 mins which was identified by HNMR as the desired compound.

Example 78

2-(4,4,5,5-tetramethyl-1,3,2-dioxaborolan-2-yl)phenol

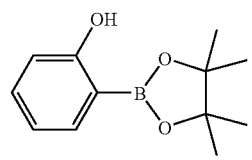

In a reaction vessel under argon, a mixture of a PdCl$_2$(dppf)CH$_2$Cl$_2$ (0.71 g; 0.85 mmol) and triethylamine (1.8 ml; 12.9 mmol) in dioxane (20.2 ml; dried over 4 Å sieves) was sealed and stirred at 80° C. overnight (18 h). After cooling to room temperature, HB(pin) (267 ml in dioxane; 1.36 M; 0.363 mol), triethylamine (47 ml; 0.34 mol) and 2-iodophenol (25.0 g; 0.114 mol) were added and the reaction mixture was stirred at 80° C. GC analysis after 30 h showed a peak at 9.2 mins which was identified by $^1$H NMR as the desired compound.

Example 79

5-(4,4,5,5-tetramethyl-1,3,2-dioxaborolan-2-yl)-1H-indole

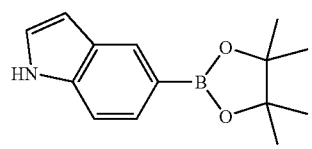

In a reaction vessel under argon, a mixture of a PdCl$_2$(dppf)CH$_2$Cl$_2$ (3.12 g; 3.8 mmol) and triethylamine (8 ml; 57.6 mmol) in dioxane (90 ml; dried over KOH) was sealed and stirred at 80° C. overnight (18 h). After cooling to room temperature, HB(pin) (205 ml in dioxane; 1.97 M; 0.404 mol), triethylamine (46 ml; 0.33 mol) and 5-bromoindole (24.8 g; 0.126 mol) were added and the reaction mixture was stirred at 80° C. GC analysis after 174 h showed a peak at 14.2 mins which was identified by $^1$H NMR as the desired compound.

Example 80

2,6-diethyl-4-(4,4,5,5-tetramethyl-1,3,2-dioxaborolan-2-yl)phenol

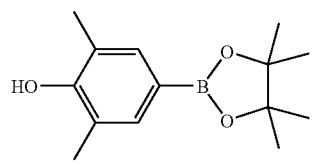

In a reaction vessel under argon, a mixture of a PdCl$_2$(dppf)CH$_2$Cl$_2$ (1.32 g; 1.62 mmol) and triethylamine (3.2 ml; 23 mmol) in dioxane (40 ml; dried over 4 Å sieves) was sealed and stirred at 80° C. overnight (18 h). After cooling to room temperature, HB(pin) (702 ml in dioxane; 1.38 M; 0.97 mol), triethylamine (135 ml; 0.97 mol) and 4-bromo-2,6-dimethylphenol (65 g; 0.323 mol) were added and the reaction mixture was stirred at 100° C. GC analysis after 14 days showed a peak at 11.6 mins which was identified by ¹H NMR as the desired compound.

Example 81

4,4,5,5-Tetramethyl-2-(2-methylphenyl-1,3,2-dioxaborolane

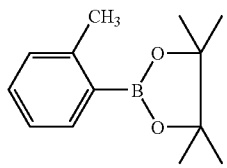

In a reaction tube under nitrogen, a mixture of PdCl$_2$(dppf)CH$_2$Cl$_2$ (22 mg; 0.027 mmol) and triethylamine (0.36 ml; 2.58 mmol) in dioxane (4 ml; dried over 4 Å sieves) was sealed and stirred at 80° C. overnight (18 h). After cooling to room temperature, HB(pin) (0.19 ml; 1.31 mmol) and 2-iodotoluene (188 mg; 0.862 mmol) were added and the reaction mixture was stirred at 80° C. GC analysis after 18 h showed a peak at 6.45 mins which was identified by GC/MS as the desired borate compound.

Example 82

4,4,5,5-Tetramethyl-2-(4-phenoxyphenyl)-1,3,2-dioxaborolane

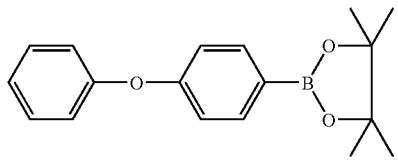

In a reaction tube under nitrogen, a mixture of PdCl$_2$(dppf)CH$_2$Cl$_2$ (22 mg; 0.027 mmol) and triethylamine (0.36 ml; 2.58 mmol) in dioxane (4 ml; dried over 4 Å sieves) was sealed and stirred at 80° C. overnight (18 h). After cooling to room temperature, HB(pin) (0.19 ml; 1.31 mmol) and 4-bromodiphenyl ether (216 mg; 0.865 mmol) were added and the reaction mixture was stirred at 80° C. GC analysis after 18 h showed a peak at 13.84 mins which was identified by GC/MS as the desired compound.

Example 83

N-[2-Fluoro-4-(4,4,5,5-tetramethyl-1,3,2-dioxaborolan-2-yl)phenyl]acetamide

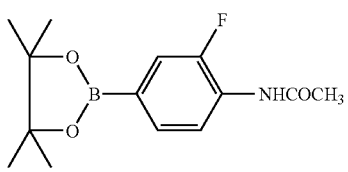

In a reaction tube under nitrogen, a mixture of PdCl$_2$(dppf)CH$_2$C$_2$ (22 mg; 0.027 mmol) and triethylamine (0.36 ml; 2.58 mmol) in dioxane (4 ml; dried over 4 Å sieves) was sealed and stirred at 80° C. overnight (18 h). After cooling to room temperature, HB(pin) (0.19 ml; 1.31 mmol) and 4-bromo-2-fluoroacetanilide (199.8 mg; 0.861 mmol) were added and the reaction mixture was stirred at 80° C. GC analysis after 52 h showed a peak at 12.64 mins which was identified by GC/MS as the desired compound.

Example 84

Ethyl 2-[4-(4,4,5,5-tetramethyl-1,3,2-dioxaborolan-2-yl)phenoxy]acetate

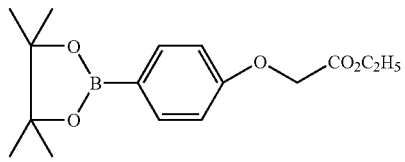

In a reaction tube under nitrogen, a mixture of PdCl$_2$(dppf)CH$_2$Cl$_2$ (22 mg; 0.027 mmol) and triethylamine (0.36 ml; 2.58 mmol) in dioxane (4 ml; dried over 4 Å sieves) was sealed and stirred at 80° C. overnight (18 h). After cooling to room temperature, HB(pin) (0.19 ml; 1.31 mmol) and ethyl-2-(4-bromophenoxy)acetate (223 mg; 0.861 mmol) were added and the reaction mixture was stirred at 80° C. GC analysis after 52 h showed a peak at 13.35 mins which was identified by GC/MS as the desired compound.

Example 85

2-(4-Bromophenyl)-4,4,5,5-tetramethyl-1,3,2-dioxaborolane

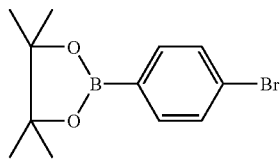

In a reaction tube under nitrogen, a mixture of PdCl$_2$(dppf)CH$_2$Cl$_2$ (22 mg; 0.027 mmol) and triethylamine (0.36 ml; 2.58 mmol) in dioxane (4 ml; dried over 4 Å sieves) was sealed and stirred at 80° C. overnight (18 h). After cooling to room temperature, HB(pin) (0.19 ml; 1.31 mmol) and 1-bromo-4-iodobenzene (244 mg; 0.862 mmol) were added and the reaction mixture was stirred at room temperature.

GC analysis after 66 h showed a peak at 8.63 mins which was identified by GC/MS as the desired compound.

Example 86

5-(4,4,5,5-Tetramethyl-1,3,2-dioxaborolan-2-yl)-1,3-benzodioxole

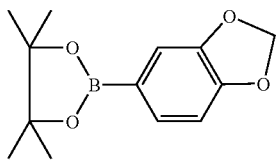

In a reaction tube under nitrogen, a mixture of PdCl$_2$(dppf)CH$_2$Cl$_2$ (22 mg; 0.027 mmol) and triethylamine (0.36 ml; 2.58 mmol) in distilled 1,2-dichloroethane (4 ml) was sealed and stirred at 80° C. overnight (18 h). After cooling to room temperature, HB(pin) (0.19 ml; 1.31 mmol) and 1-iodo-3,4-methylenedioxybenzene (215 mg; 0.867 mmol) were added and the reaction mixture was stirred at 40° C.

GC analysis after 1.25 h showed a peak at 9.54 mins (7.2%) which was identified by GC/MS as the desired compound.

Example 87

5-(4,4,5,5-Tetramethyl-1,3,2-dioxaborolan-2-yl)-1,3-benzodioxole

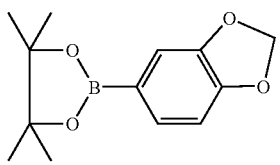

In a reaction tube under nitrogen, a mixture of PdCl$_2$(dppf)CH$_2$Cl$_2$ (22 mg; 0.027 mmol) and triethylamine (0.36 ml; 2.58 mmol) in distilled dimethoxyethane (4 ml) was sealed and stirred at 80° C. overnight (18 h). After cooling to room temperature, HB(pin) (0.19 ml; 1.31 mmol) and 1-iodo-3,4-methylenedioxybenzene (216 mg; 0.870 mmol) were added and the reaction mixture was stirred at 40° C.

GC analysis after 1.25 h showed a peak at 9.61 mins (57.8%) which was identified by GC/MS as the desired compound.

Example 88

5-(4,4,5,5-Tetramethyl-1,3,2-dioxaborolan-2-yl)-1,3-benzodioxole

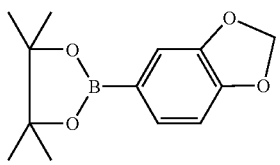

In a reaction tube under nitrogen, a mixture of PdCl$_2$(dppf)CH$_2$Cl$_2$ (22 mg; 0.027 mmol) and triethylamine (0.36 ml; 2.58 mmol) in toluene (4 ml; dried over 4 Å sieves) was sealed and stirred at 80° C. overnight (18 h). After cooling to room temperature, HB(pin) (0.19 ml; 1.31 mmol) and 1-iodo-3,4-methylenedioxybenzene (214 mg; 0.863 mmol) were added and the reaction mixture was stirred at 40° C.

GC analysis after 1.25 h showed a peak at 9.59 mins (39.5%) which was identified by GC/MS as the desired compound.

Example 89

5-(4,4,5,5-Tetramethyl-1,3,2-dioxaborolan-2-yl)-1,3-benzodioxole

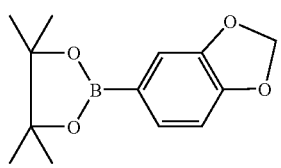

In a reaction tube under nitrogen, a mixture of PdCl$_2$(dppf)CH$_2$Cl$_2$ (22 mg; 0.027 mmol) and triethylamine (0.36 ml; 2.58 mmol) in dioxane (4 ml; dried over 4 Å sieves) was sealed and stirred at 80° C. overnight (18 h). After cooling to room temperature, HB(pin) (0.19 ml; 1.31 mmol) and 1-iodo-3,4-methylenedioxybenzene (214 mg; 0.863 mmol) were added and the reaction mixture was stirred at 40° C.

GC analysis after 1.25 h showed a peak at 9.53 mins (46.1%) which was identified by GC/MS as the desired compound.

Example 90

3-(4,4,5,5-Tetramethyl-1,3,2-dioxaborolan-2-yl)aniline

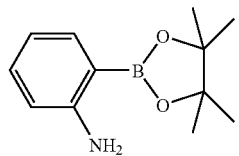

The experimental procedure described in Example 76 was repeated using 3-bromoaniline. The product was identified by GC and NMR methods.

Example 91

Synthesis of an arylboronic acid ester possessing an active hydrogen and the coupling of this species with a second aryl halide in the one pot to form an asymmetric biaryl.

Formation of N-[4-(1,3-benzodioxol-5-yl)phenyl]acetamide

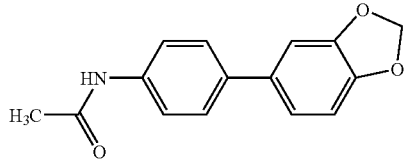

4-iodoacetanilide (262 mg; 1 mmol) were reacted at 80° C. with 0.25 ml (1.8 mmol) of pinacolborane in a dioxane solution (5 ml) containing 25 mg PdCl$_2$[dppf].CH$_2$Cl$_2$ and 0.45 ml triethylamine. The catalyst had been activated by heating at 80° C. for 24 h in dioxane with the triethylamine. GC of the reaction solution showed that all the 4-iodoacetanilide had reacted to give the required boronic acid ester together with some acetanilide and phenylboronic acid pinacol ester. After cooling to room temperature, 2 ml of ethanol were added to the reaction vessel to destroy the excess pinacolborane. After the liberation of hydrogen had ceased, 450 mg of K$_2$CO$_3$ and 281 mg (1 mmol) of 1-iodo-3,4-methylenedioxybenzene were added and the reaction heated to 80° C. for 18.5 h. GC analysis on an aliquot of the reaction solution showed no arylboronic acid ester and a strong peak for the biaryl product at 17.7 mins.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The invention claimed is:

1. A process for the synthesis of an alkene or aryl borate which comprises reacting:
   (i) an olefinic compound having a halogen or halogen-like substituent in a vinylic substitution position, or
   (ii) an aromatic ring compound having a halogen or halogen-like substituent in a ring substitution position, said aromatic ring compound also having at least one substituent selected from the group consisting of hydroxy, amino, amino, acetyleno, carboxy (including carboxylato), carboximidyl, sulfo, sulfinyl, sulfinimidyl, sulfinohydroximyl, sulfonimidyl, sulfondiimidyl, sulfonohydroximyl, sultamyl, phosphinyl, phosphinimidyl, phosphonyl, dihydroxyphosphanyl, hydroxyphosphanyl, phosphono (including phosphonato), hydrohydroxyphosphoryl, allophanyl, guanidino, hydantoyl, ureido, and ureylene,
   with a disubstituted monohydroborane, in the presence of a Group 8–11 metal catalyst and a suitable base, such that a borane residue is introduced at the substitution position.

2. A process according to claim 1 wherein the disubstituted monohydroborane is generated by reaction of a borane with an appropriate alcohol or amine, and used without isolation.

3. A process according to claim 2 wherein disubstituted monohydroborane is generated in situ.

4. A process according to claim 2 wherein the borane is a polyhydroborane.

5. A process according to claim 4 wherein the polyhydroborane is selected from 30 sulphide and ether adducts of BH$_3$.

6. A process according to claim 5 wherein the polyhydroborane is selected from BH$_3$.S(CH$_3$)$_2$, BH$_3$.THF and BH$_3$.1,4-oxathiane.

7. A process for covalently coupling organic compounds which comprises:
   (A) preparing an alkene or aryl borate by reacting
      (i) an olefinic compound having a halogen or halogen-like substituent in a vinylic coupling position, or
      (ii) an aromatic ring compound having a halogen or halogen-like substituent in a ring coupling position, said aromatic ring compound also having at least one substituent which is selected from the group consisting of hydroxy, amino, imino, acetyleno, carboxy (including carboxylato), carboximidyl, sulfo, sulfinyl, sulfinimidyl, sulfinohydroximyl, sulfonimidyl, sulfondiimidyl, sulfonohydroximyl, sultamyl, phosphinyl, phosphinimidyl, phosphonyl, dihydroxyphosphanyl, hydroxyphosphanyl, phosphono (including phosphonato), hydrohydroxyphosphoryl, allophanyl, guanidino, hydantoyl, ureido, and ureylene,
      with a disubstituted monohydroborane, in the presence of a Group 8–11 metal catalyst and a suitable base, such that borane residue is introduced at said coupling position; and
   (B) reacting the alkene or aryl borate with an organic compound having a halogen or halogen-like substituent at a coupling position in the presence of a Group 8–11 metal catalyst and a suitable base, whereby the olefinic or aromatic ring compound is coupled to the organic compound via a direct bond between the respective coupling positions.

8. A process according to claim 7 wherein the disubstituted monohydroborane is generated by reaction of a borane with an appropriate alcohol or amine.

9. A process according to claim 8 wherein the borane is a polyhydroborane.

10. A process according to claim 7 conducted in a single pot.

11. A process according to claim 10 wherein after preparation of the alkene or aryl borate, excess disubstituted monohydroborane is decomposed by adding a suitable proton donor compound.

12. A process according to claim 11 wherein the proton donor compound is selected from water, alcohols, acids and mixtures thereof.

13. A process according to claim 7 for the preparation of symmetrical coupled products wherein said disubstituted monohydroborane is contacted with two equivalents of said olefinic or aromatic ring compound to form an alkene or aryl borate, which borate reacts with the remaining olefinic or aromatic compound to form a symmetrical coupled product.

14. A process according to claim 10 wherein a second base is added after the formation of the alkene or aryl borate to catalyse or promote the coupling reaction.

15. A process according to claim 7 wherein the organic compound having a halogen or halogen-like substituent at a coupling position is different from the olefinic or aromatic ring compound such that the coupled product is unsymmetrical.

16. A process according to claim 1 wherein the olefinic compound (i) is a compound of formula I

I $$\begin{array}{c} R^2 \\ \diagdown \\ R^3 \end{array} C = C \begin{array}{c} R^1 \\ \diagup \\ X \end{array}$$

II $$-B \begin{array}{c} X \\ \diagdown \\ X \end{array} R'$$

where $R^1$, $R^2$ and $R^3$ are each independently selected from hydrogen, alkyl, alkenyl, alkynyl, aryl, heteroaryl, acyl, arylalkyl and heteroarylalkyl (each of which may be optionally substituted), cyano, isocyano, formyl, carboxyl, nitro, halo, alkoxy, alkenoxy, aryloxy, benzyloxy, haloalkoxy, haloalkenyloxy, haloaryloxy, nitroalkyl, nitroalkenyl, nitroalkynyl, arylamino, diarylamino, dibenzylamino, alkenylacyl, alkynylacyl, arylacyl, acylamino, diacylamino, acyloxy, alkylsulphonyloxy, arylsulphenyloxy, heterocycloxy, arylsulphenyl, carboalkoxy, carboaryloxy, alkylthio, benzylthio, acylthio, sulphonamide, sulfanyl, sulfo, carboxy (including carboxylato), carbamoyl, carboximidyl, sulfinyl, sulfinimidyl, sulfinohydroximyl, sulfonimidyl, sulfondiimidyl, sulfonohydroximyl, sulfamyl, phosphorous containing groups (including phosphinyl, phosphinimidyl, phosphonyl, dihydroxyphosphanyl, hydroxyphosphanyl, phosphone (including phosphonato) and hydrohydroxyphosphoryl), alkoxysilyl, silyl, alkylsilyl, alkylalkoxysilyl, phenoxysilyl, alkylphenoxysilyl, alkoxyphenoxy silyl and arylphenoxy silyl, and X is a halogen or halogen-like substituent.

17. A process according to claim 7 wherein the alkene or aryl borate is isolated prior to reaction with the organic compound.

18. A process according to claim 1 wherein the olefinic compound having a halogen-like substituent in a vinylic substitution position is prepared from a compound having a carbonyl group with a β-hydrogen.

19. A process for the synthesis of an alkene or aryl borate which comprises reacting:
(i) an olefinic compound having a halogen or halogen-like substituent in a vinylic substitution position, or
(ii) an aromatic ring compound having a halogen or halogen-like substituent in a ring substitution position,
with a disubstituted monohydroborane, in the presence of a Group 8–11 metal catalyst, a suitable base and a promoter such that a borane residue is introduced at the substitution position.

20. A process according to claim 19 wherein the promoter is an amide.

21. A process according to claim 20 wherein the promoter is selected from p-iodoacetanilide, acetanilide, acetamide and N-methyl acetamide.

22. A process according to claims 1 wherein the Group 8–11 metal catalyst is activated with base(s) before the disubstituted monohydroborane is contacted with the catalyst.

23. A process according to claim 22 wherein said activation is achieved by heating the catalyst with the base.

24. A process according to claim 22 wherein the base(s) includes an organic amine.

25. A process according to claim 1 wherein the monohydroborane is a compound of formula:

$(RX)_2B-H$ where each X is independently selected from O, S and NR" where R" is H, optionally substituted alkyl or optionally substituted aryl and each R is independently selected from optionally substituted alkyl and optionally substituted aryl or where $-B(XR)_2$ represents a cyclic group of formula II where R' is optionally substituted alkylene, arylene or other divalent group comprising linked aliphatic or aromatic moieties and X is as defined above.

26. A process according to claim 25 wherein the disubstituted monohydroborane is a dialkoxy hydroborane.

27. A process according to claim 23 wherein the dialkoxymonohydroborane is selected from the group consisting of 4,4-dimethyl-1,3,2-dioxaborinane, 4,4,6-trimethyl-1,3,2-dioxaborinane, 4,4,6,6-tetramethyl-1,3,2-dioxaborinane, 4,4-dimethyl-1,3,2-dioxaborolane, 4,4,5-trimethyl-1,3,2dioxaborolane, 4,4,5,5-tetramethyl-1,3,2-dioxaborolane, 4-phenyl-1,3,2-dioxaborinane, n-propanediolborane (1,3,2-dioxaborinane), 5,5-dimethyl-1,3,2-dioxaborinane, (4R,5R)-4,5-bis(1-methoxy-1-methylethyl)-1,3,2-dioxaborolane, (4S,5S)-4,5-bis(1-methoxy-1-methylethyl)-1,3,2-dioxaborolane, dinaphtho[2,1-d:1,2-f][1,3,2]dioxaborepine, (4R,5R)-3,4-dimethyl-5-phenyl-1,3,2-oxazaborolidine, (4S,5S)-3,4-dimethyl-5-phenyl-1,3,2-oxazaborolidine, (4R,5R)-3-isopropyl-4-methyl-5-phenyl-1,3,2-oxazaborolidine, (4S,5S)-3-isopropyl-4-methyl-5-phenyl-1,3,2-oxazaborolidine, (4R,5R)-4,5-dimethyl-1,3,2-dioxaborolane, (4S,5S)-4,5-dimethyl-1,3,2-dioxaborolane, (4R,5R)-4,5-diphenyl-1,3,2-dioxaborolane, (4S,5S)-4,5-diphenyl-1,3,2-dioxaborolane, (4S)-4-(methoxymethyl)-1,3,2-dioxaborolane, (4R)-4-(methoxymethyl)-1,3,2-dioxaborolane, tetrahydro-3aH-cyclopenta[d][1,3,2]dioxaborole, 3-methyl-1,3,2-oxazaborolidine, (6R)-4,4,6-trimethyl-1,3,2-dioxaborinane, (6S)-4,4,6-trimethyl-1,3,2-dioxaborinane, hexahydro-1,3,2-benzodioxaborole, (4R,5R)-4,5-bis(methoxymethyl)-1,3,2-dioxaborolane, (4S,5S)-4,5-bis(methoxymethyl)-1,3,2-dioxaborolane, (4R,5R)-4,5-dicyclohexyl-1,3,2-dioxaborolane (4S,5S)-4,5-dicyclohexyl-1,3,2-dioxaborolane, (5R)-4,4-dimethyl-5-phenyl-1,3,2-dioxaborolane, (5S)-4,4-dimethyl-5-phenyl-1,3,2-dioxaborolane, (4R)-4-phenyl-1,3-dioxa-2-boraspiro[4,4]nonane, (4S)-4-phenyl-1,3-dioxa-2-boraspiro[4,4]nonane, (4S,5S)-4,5-bis(1-methoxycyclopentyl)-1,3,2-dioxaborolane, (4R,5R)-4,5-bis(1-methoxycyclopentyl)-1,3,2-dioxaborolane, diisopropyl (4S,5S)-1,3,2-dioxaborolane-4,5-dicarboxylate, diisopropyl (4R,5R)-1,3,2-dioxaborolane-4,5-dicarboxylate, (1R,2S,6S,7S)-1,10,10-trimethyl-6-phenyl-3,5-dioxa-4-boratricyclo[5,2,1,0$^{2,6}$]decane, (1S,2R,6R,7R)-1,10,10-trimethyl-6-phenyl-3,5-dioxa-4-boratricyclo[5,2,1,0$^{2,6}$]decane, (3aR)-3a-methyl-3,3-di(2-naphthyl)tetrahydro-3H-pyrrolo[1,2-c][1,3,2]oxazaborole, (3aS)-3a-methyl-3,3-di(2-naphthyl)tetrahydro-3H-pyrrolo[1,2-c][1,3,2] oxazaborole, (3aR)-3,3-di(2-naphthyl)tetrahydro-3H-pyrrolo[1,2-c][1,3,2]oxazaborole, (3aS)-3,3-di(2-naphthyl)tetrahydro-3H-pyrrolo[1,2-c][1,3,2]oxazaborole, (4S,5S)-4,5-bis[(4R)-2,2-dimethyl-1,3-dioxolan-4-yl]-1,3,2-dioxaborolane, (4R,5R)-4,5-bis[(4S)-2,2-dimethyl-1,3-dioxolan-4-yl]-1,3,2-dioxaborolane, (2R)-2-{(4S,5S)-5-[(2R)-1,4-dioxaspiro[4,5]dec-2-yl]-1,3,2-dioxaborolan-4-yl}-1,4-dioxaspiro[4,5]decane, (2S)-2-{(4R,5R)-5-[(2S)-1,4-dioxaspiro[4,5]dec-2-yl]-1,3,2-dioxaborolan-4-yl}-1,4-dioxaspiro[4,5]decane, (4S,5S)-N$^4$,N$^4$,N$^5$,N$^5$-tetramethyl-1,3,2-dioxaborolane-4,5-dicarboxamide, (4R,5R)-N$^4$,N$^4$,N$^5$,N$^5$-tetramethyl-1,3,2-dioxaborolane-4,5-dicarboxamide, (1R,2R,6S,8R)-2,9,9-trimethyl-3,5-dioxa-4-boratricyclo[6, 1,1,0²,⁶]decane and (1S,2S,6R,8S)-2,9,9-trimethyl-3,5-di-oxa-4-boratricyclo[6,1,1,0²,⁶]decane.

28. A process according to claim 1 wherein the Group 8–11 metal catalyst comprises Ni, Pt or Pd.

29. A process according to claim 28 wherein the catalyst is a palladium catalyst.

30. A process according to claim 29 wherein the palladium catalyst is a palladium complex.

31. A process according to claim 30 wherein the palladium complex is selected from $Pd_3(dba)_3$, $PdCl_2$, $Pd(OAc)_2$, $PdCl_2(dppf)CH_2Cl_2$, $Pd(PPh_3)_4$ and related catalysts which are complexes of phosphine ligands, phosphite ligands, or other suitable ligands containing P and/or N atoms for coordinating the platinum atoms.

32. A process according to claim 30 wherein the palladium complex is tethered on a solid support.

33. A process according to claim 29 wherein the palladium catalyst is selected from palladium black, palladium or carbon, palladium clusters, palladium clusters containing other metals and palladium in porous glass.

34. A process according to claim 28 wherein the Group 8–11 metal catalyst is a platinum catalyst.

35. A process according to claim 28 wherein the Group 8–11 metal catalyst is nickel catalyst.

36. A process according to claim 7 wherein the suitable base for coupling step B is selected from the group consisting of aryl and alkyl carboxylates, fluorides, hydroxides and carbonates of Li, Na, K, Rb, Cs, ammonium, alkylammonium, Mg, Ca and Ba; phosphates, and arylphosphates of Li, Na, K, Rb and Cs; phosphate esters of Li, Na, K, Rb and Cs, phenoxides of Li, Na, K, Rb and Cs; alkoxides of Li, Na, K, Rb and Cs; and thallium hydroxide.

37. A process of claim 7 wherein the suitable base for the coupling step is selected from caesium carbonate, potassium carbonate, potassium phosphate and alkali metal hydroxides.

38. A process of claim 7 wherein one of said olefinic or aromatic compound, and said organic compound, is a polymer.

39. A process of claim 7 wherein either the olefinic compound or aromatic ring, or the organic compound, is chemically linked to a solid polymer support.

40. A process for the synthesis of an alkene or aryl borate which comprises reacting
   (i) an olefinic compound having a halogen or halogen-like substituent in a vinylic substitution position, or
   (ii) an aromatic ring compound having a halogen or halogen-like substituent in a ring substitution position,
   with a disubstituted monohydroborane, in the presence of a Group 8–11 metal catalyst and a suitable base such that a borane residue is introduced at the substitution position,
   wherein the Group 8–11 metal catalyst is activated by treatment with an organic amine prior to contacting of the disubstituted monohydroborane with the catalyst.

41. A process according to claim 40 wherein the treatment with the organic amine is conducted by heating the catalyst with the organic amine.

* * * * *